US012790642B2

(12) United States Patent
Bick et al.

(10) Patent No.: US 12,790,642 B2
(45) Date of Patent: Nov. 10, 2026

(54) SCALABLE MULTIPLEX DETECTION OF SOMATIC MUTATIONS

(71) Applicant: VANDERBILT UNIVERSITY, Nashville, TN (US)

(72) Inventors: Alexander G. Bick, Nashville, TN (US); Angela Jones, Nashville, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 486 days.

(21) Appl. No.: 18/361,068

(22) Filed: Jul. 28, 2023

(65) Prior Publication Data

US 2024/0043917 A1 Feb. 8, 2024

Related U.S. Application Data

(60) Provisional application No. 63/369,808, filed on Jul. 29, 2022.

(51) Int. Cl.
*C12Q 1/6855* (2018.01)
*C12Q 1/6874* (2018.01)

(52) U.S. Cl.
CPC ......... *C12Q 1/6855* (2013.01); *C12Q 1/6874* (2013.01)

(58) Field of Classification Search
None
See application file for complete search history.

(56) References Cited

PUBLICATIONS

Vollbrecht et al., "Targeting Cancer Related Genes by Multiplex PCR Followed by High Throughput Parallel Sequencing," Int. J. Genomic Med. 2014, 2:115. (Year: 2014).*
Abplanalp, Wesley Tyler, et al., "Association of Clonal Hematopoiesis of Indeterminate Potential With Inflammatory Gene Expression in Patients With Severe Degenerative Aortic Valve Stenosis or Chronic Postischemic Heart Failure," JAMA Cardiol., vol. 5, No. 10 (2020), pp. 1170-1175.
Bick, Alexander G., et al., "Genetic Interleukin 6 Signaling Deficiency Attenuates cardiovascular Risk in Clonal Hematopoiesis," Circulation, vol. 141 (2020), pp. 124-131.
Bick, Alexander, G., et al., "Inherited causes of clonal haematopoiesis in 97,691 whole genomes," Nature, vol. 586 (2020), pp. 763-786.
(Continued)

*Primary Examiner* — Kaijiang Zhang
(74) *Attorney, Agent, or Firm* — Thomas | Horstemeyer, LLP

(57) ABSTRACT

Disclosed herein is a scalable multiplex method for amplifying a plurality of target DNA regions collectively 1 kb to 100 kb in size in a plurality of samples. Also disclosed herein is a scalable multiplex method for identifying a subject with increased risk of developing a cardiometabolic disease or a hematological cancer that involves amplifying and sequencing target DNA regions corresponding to the genes DNMT3A, TET2, ASXL1, JAK2, GNAS, GNB, CBL, TP53, PPM1D, SF3B1, SRSF2, PIGA, BCOR, BCORL1, DNMT3A, and ASXL1 from a plurality of DNA samples according to the method disclosed herein, and identifying from said sequencing one or more mutations in one or more of the genes, wherein presence of said mutation(s) indicates an increased risk of developing a cardiometabolic disease and/or a hematological cancer.

10 Claims, 9 Drawing Sheets

Specification includes a Sequence Listing.

(56) References Cited

PUBLICATIONS

Busque, Lambert, et al., "Nanrandom X-Inactivation Patterns in Normal Females: Lyonization Ratios Vary With Age," Blood, vol. 88, No. 1 (1996), pp. 59-65.
Fey, Martin F., et al., "Clonality and X-Inactivation Patterns in Hematopoietic Cell Populations Detected by the Highly Informative M27B DNA Probe," Blood, vol. 83, No. 4 (1994), pp. 931-938.
Fuster, Jose J., et al., "Clonal hematopoiesis associated with TET2 deficiency accelerates atherosclerosis development in mice," Science, vol. 355 (2017), pp. 842-847.
Gale, Rosemary E., et al., "Acquired skewing of X-chromosome inactivation patterns in myeloid cells of the elderly suggests stochastic clonal loss with age," British Journal of Haematology, vol. 98 (1997), pp. 512-519.
Genovese, Giulio, et al., "CLonal Hematopoiesis and Blood-Cancer Risk Inferred from Blood DNA Sequence," The New England Journal of Medicine, vol. 317 (2014), pp. 2477-2487.
Greider, Carol W., "Telomeres and senescence: The history, the experiment, the future," Current Biology, vol. 8 (1998), pp. R178-R181.
Honigberg, Michael C., et al., "Premature Menopauswe, Clonal Hematopoiesis, and Coronary Artery Disease in Postmenopausal Women," Circulation, vol. 143 (2021), pp. 410-423.
Haiswal, Siddhartha, et al., "Clonal hematopoiesis in human aging and disease," Science, vol. 366 (2019), (8 pgs).
Jaiswal, Siddhartha, et al., "Age-Related Clonal Hematopoiesis Associated with Adverse Outcomes," The New England Journal of Medicine, vol. 371 (2014), pp. 2488-2498.
Jaiswal, S., et al., "Clonal Hematopoiesis and Risk of Atherosclerotic Cardiovascular Disease," The New England Journal of Medicine, vol. 377 (2017), pp. 111-121.
Khetarpal, Sumeet A., et al., "Clonal Hematopoiesis of Indeterminate Potential Reshapes Age-Related CVD," The Journal of the American College of Cardiology, vol. 74, No. 4 (2019), pp. 579-586.
Lander, Eric S., et al., "Genetic Dissection of Complex Traits," Science, vol. 265 (1994), pp. 2037-2048.
Lawrence, Michael S., et al., "Discovery and saturation analysis of cancer genes across 21 tumour types," Nature, vol. 505 (2014) (9 pgs).
Lee-Six, Henry, et al., "Population dynamics of normal human blood inferred from somatic mutations," Nature, vol. 561 (2018), pp. 473-490.
Loh, Po-Ru, et al., "Insights in to clonal haematopoiesis from 8,342 mosaic chromosomal alterations," Nature, vol. 559 (2018), pp. 350-371.
Loh, Po-Ru, et al., "Monogenic and polygenic inheritance become instruments for clonal selection," Nature, vol. 584 (2020), pp. 136-158.
Natarajan, Pradeep, et al., "Clonal Hematopoiesis," Cir. Genom. Precis. Med., vol. 11 (2018) (12 pgs).
Osorio, Fernando G., et al., "Somatic Mutations Reveal Lineage Relationships and Age-Related Mutagenesis in Human Hematopoiesis," Cell Reports, vol. 25 (2018), pp. 2308-2316.
Steensma, David P., et al, "Clonal hematopoiesis of indeterminate potential and its distinction from myelodyslastic syndromes," Blood, vol. 126 (2015), pp. 9-16.
Terao, Chikashi, et al., "Chromosomal alterations among age-related haematopoietic clones in Japan," Nature, vol. 584 (2020), pp. 130-150.
Wallace, Douglas C., "A mitochondrial bioenergetic etiology of disease," The Journal of Clinical Investigation, vol. 123, No. 4 (2013), pp. 1405-1412.
Watson, Caroline J., et al., "The evolutionary dynamics and fitness landscape of clonal hematopoiesis," Science, vol. 367 (2020), pp. 1449-1454.
Welch, John S., et al., "The Origin and Evolution of Mutations in Acute Myeloid Leukemia," Cell, vol. 150 (2012), pp. 264-278.
Xie, Mingchao, et al., "Age-related mutations associated with clonal hematopoietic expansion and malignacies," Nature Medicine, vol. 20, No. 12 (2014), pp. 1472-1478.
Young, Andrew L., et al., "Clonal haematopoiesis harbouring AML-associated mutations is ubiquitous in healthy adults," Nature Communications, vol. 10 (2016) (7 pgs).
Young, Andrew L., et al., "Clonal hematopoiesis and risk of acute myeloid leukemia," Haematologica, vol. 104 (2019), pp. 2410-2417.
Zekavat, Seyedeh M., et al., "Hematopoietic mosaic chromosomal alterations and risk for infection among 767,891 individuals without blood cancer," MedRxiv (2020) (41 pgs.).
Harlow, Ed., et al., "Antibodies—A Laboratory Manual," Spring Harbor Laboratory publications, Chapter 9 (1988) (6 pages).

* cited by examiner

SCALABLE MULTIPLEX DETECTION OF SOMATIC MUTATIONS

CROSS-REFERENCE TO RELATED APPLICATIONS

This application claims benefit of U.S. Provisional Application No. 63/369,808, filed Jul. 29, 2022, which is hereby incorporated herein by reference in its entirety.

STATEMENT REGARDING FEDERALLY SPONSORED RESEARCH OR DEVELOPMENT

This invention was made with Government Support under Grant No. OD029586 awarded by the National Institutes of Health. The Government has certain rights in the invention.

SEQUENCE LISTING

This application contains a sequence listing filed in ST.26 format entitled "222230-1160 Sequence Listing" created on Jul. 24, 2023, and having 149,127 bytes.

The content of the sequence listing is incorporated herein in its entirety.

BACKGROUND

Although germline genome sequences are set at conception, genomes are in fact changing throughout life, even in the absence of malignancy. For example, leukocyte telomeres shorten, somatic mutations arise in replicating cellular populations long before malignancy occurs, and mitochondria heteroplasmy evolves. These changes that occur in our germline DNA with aging and diverse lifetime exposures are referred to herein as a "dynamic genome".

Until recently, analyzing dynamic changes to the germline DNA was a fundamental division between cancer genomics and the rest of human disease genetics. Within cancer genomics there has long been an emphasis on the mutations that arise within the cancer tumor in comparison to the normal tissue. Yet in much of the remainder of human disease genetics the focus has been on the germline genome and associating naturally arising variation between individuals who are affected by a condition and those who are not. A fundamental tenant of such human genetic association analyses is that the germline genome fixed at conception and does not change. Over the past five years, there is increasing appreciation within the nonmalignant disease genomics community that this fixed notion of DNA sequence is perhaps more flexible then has been postulated—especially when analyzing DNA derived from blood.

Aging is associated with the accumulation of somatic mutations across cells. Similar to other stem cells, hematopoietic stem cells (HSCs) accumulate mutations leading to increasing genetic diversity across an individual's lifetime. Individual HSCs are estimated to acquire 200 mutations per decade genome-wide, with 1 mutation per decade occurring within an exonic region. While the vast majority of such mutations do not have substantive impacts on cellular fitness, occasionally one such mutation may promote vitality and proliferation termed clonal hematopoiesis (CH).

CH has long been hypothesized as a key precursor in a sequential model of leukemogenesis. Age-related HSC clonal abnormalities in asymptomatic individuals was first recognized three decades ago through the analyses of non-random X-inactivation patterns derived from peripheral leukocytes of women. Population-based next-generation sequencing over the last decade has shown that CH is surprisingly common with approximately 1 in 10 asymptomatic adults older than 70 years affected. Using whole exome sequences of blood DNA originally aimed to discover rare germline disruptive coding alleles contributing to risk for common complex diseases, investigators employed methods to detect acquired mutations. 'Clonal hematopoiesis of indeterminate potential' (CHIP) is the presence of a hematologic malignancy driver mutation (typically in DNMT3A, TET2, ASXL1, JAK2) with high variant allele frequency in blood (i.e., >2%) indicative of clonality. While CHIP is a strong risk factor for hematologic malignancy, risk is not absolute with ~0.5%/year progression from CHIP to hematologic malignancy.

A more surprising finding related to CHIP is that its implications for coronary artery disease may be a more important than hematologic malignancy. In several datasets, CHIP is associated with a 1.6-1.9-fold risk for coronary artery disease (CAD), and thus larger absolute risk increase for CAD compared to hematologic malignancy. Among asymptomatic individuals, individuals with CHIP have a greater burden of subclinical coronary atherosclerosis compared to those without. Consistent with the human observations, irradiated mice transplanted with Tet2−/− bone marrow versus transplanted with wild type bone marrow have a greater burden of supravalvular and descending aortic atherosclerosis. Both humans and mice with CHIP mutations in hematopoietic stem cells have greater concentrations of circulating inflammatory cytokines. Inhibition of the NLRP3 inflammasome mitigates atherosclerosis to a greater degree in irradiated mice transplanted with Tet2−/− bone marrow versus transplanted with wild type bone marrow. Similarly, genetic deficiency of IL6-receptor, in the NLRP3 pathway, through the presence of a common IL6R missense mutation in humans is associated with a greater reduction in cardiovascular disease risk among those with CHIP versus without. These data imply that for patients with CHIP, a tailored anti-inflammatory approach may be highly effective at addressing CHIP-associated cardiovascular disease risk. The increasingly robust therapeutic hypothesis is ripe for testing in placebo-controlled clinical trials.

Additional forms of CH have also been detected from the analysis of blood DNA. Larger chromosomal rearrangements, often term mosaic chromosomal alterations (mCAs) or clonal somatic copy number alterations, have been identified from large-scale blood DNA-derived genome-wide genotyping. While CHIP is strongly associated with myeloid malignancies, mCAs are strongly associated with lymphoid malignancies. Unlike CHIP, mCAs are not associated with CAD. Additionally, mCAs may represent more widespread immunologic dysfunction as they predict diverse incident cancers and infections.

Currently to detect CHIP requires either a whole genome/whole exome sequence or a selective amplification of DNA followed by sequencing (e.g. the Illumina TruSight Oncology test). Current approaches that accomplish this range cost about $250 to $1000. A more efficient assay to detect CHIP is therefore needed.

SUMMARY

Disclosed herein is a scalable multiplex method for amplifying a plurality of target DNA regions collectively 1 kb to 100 kb in size in a plurality of samples. In some embodiments the method involves pooling a plurality of samples containing input DNA; performing mechanical or enzymatic DNA fragmentation, end repair, and dA-tailing of the input DNA to produce dA-tailed DNA fragments; ligating universal adapters to the dA-tailed DNA fragments to generate a DNA library; normalizing the DNA library; and hybridization capturing dA-tailed DNA fragments in the DNA target regions from the normalized barcoded-DNA library.

In some embodiments, normalizing the DNA library involves PCR amplifying the DNA library using normalase unique dual index (UDI) primers, enzymatic selection of library fractions using Normalase I, bead purification to purify and select for target region size, pooling the library fractions, and enzymatic normalization of the pooled library fractions with Normalase II.

In some embodiments, hybridization capturing dA-tailed DNA fragments in the DNA target regions from the normalized barcoded-DNA library involves hybridization capture of the dA-tailed DNA fragments with capture probes, washing and amplification of the captured dA-tailed DNA fragments using primers specific for the universal adapter, and quantification of the amplified DNA.

In some embodiments, the method further involve sequencing the amplified DNA.

Also disclosed herein is a scalable multiplex method for identifying a subject with increased risk of developing a cardiometabolic disease or a hematological cancer that involves amplifying and sequencing target DNA regions corresponding to the genes DNMT3A, TET2, ASXL1, JAK2, GNAS, GNB, CBL, TP53, PPM1D, SF3B1, SRSF2, PIGA, BCOR, BCORL1, DNMT3A, and ASXL1 from a plurality of DNA samples according to the method disclosed herein, and identifying from said sequencing one or more mutations in one or more of the genes, wherein presence of said mutation(s) indicates an increased risk of developing a cardiometabolic disease and/or a hematological cancer.

In some embodiments, the cardiometabolic disease is atherosclerosis, coronary heart disease (CHD) or ischemic stroke (IS). In some embodiments, the hematological cancer is a leukemia, a lymphoma, a myeloma or a blood syndrome. In some embodiments, the leukemia is acute myeloid leukemia (AML) or chronic myelogenous leukemia (CML). In some embodiments, the blood syndrome is myelodysplastic syndrome (MDS).

In some embodiments, the DNA samples are obtained from one more cells in blood samples comprising hematopoietic stem cells (HSCs), committed myeloid progenitor cells having long term self-renewal capacity, or mature lymphoid cells having long term self-renewal capacity.

In some embodiments, the subject exhibits one or more risk factors of being a smoker, having a high level of total cholesterol or having high level of high-density lipoprotein (HDL).

In some embodiments, the one or more mutations are frameshift mutations, nonsense mutations, missense mutations or splice-site variant mutations.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
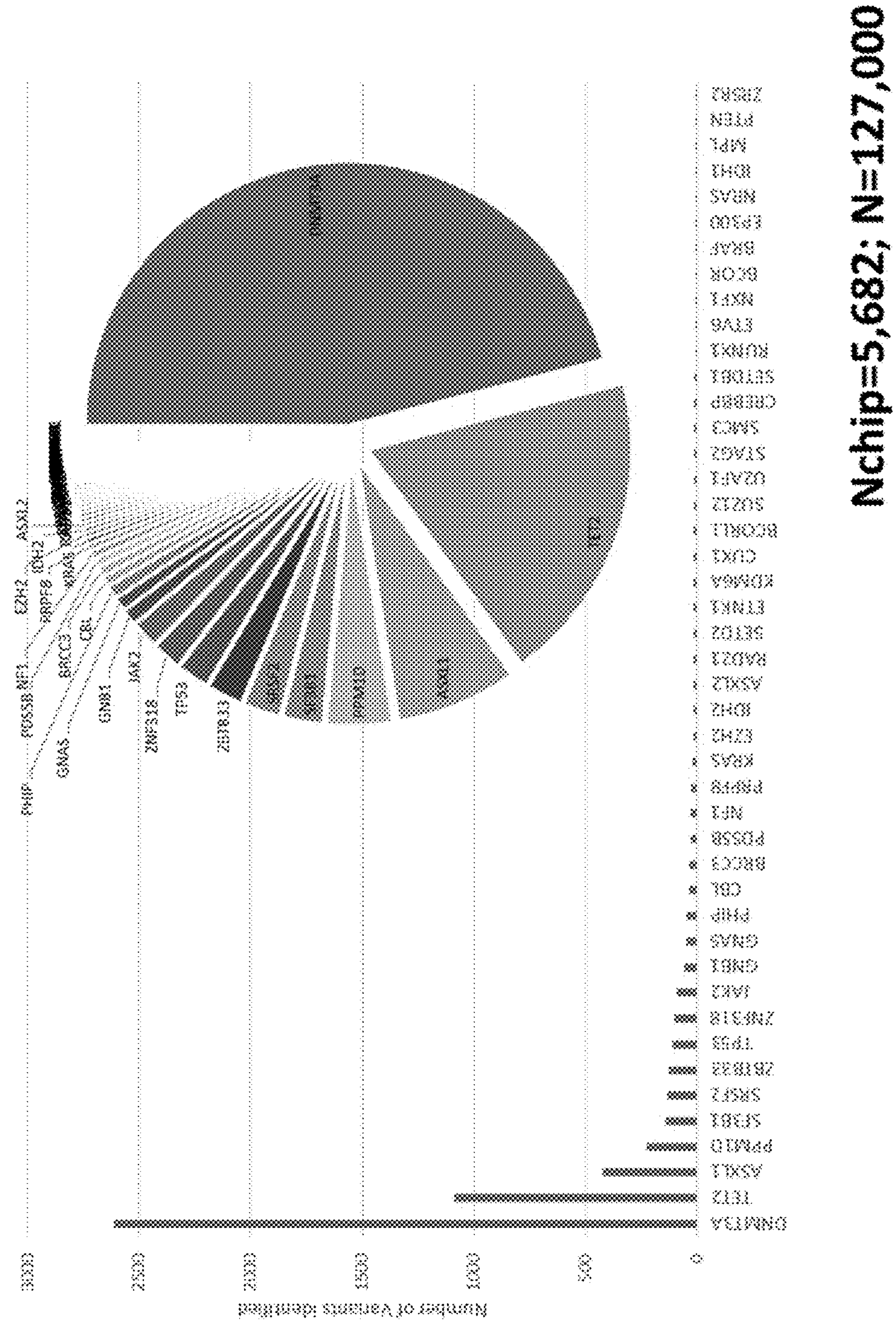
FIG. 1 shows distribution of gene mutations in patients with CHIP.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, biology, and the like, which are within the skill of the art.

The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in °C, and pressure is at or near atmospheric. Standard temperature and pressure are defined as 20 °C and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise.

DNA Library Preparation

Disclosed herein is a scalable multiplex method for amplifying a plurality of target DNA regions collectively 1 kb to 100 kb in size in a plurality of samples. This method involves pooling a plurality of samples containing input DNA; performing mechanical or enzymatic DNA fragmentation, end repair, and dA-tailing of the input DNA to produce dA-tailed DNA fragments; ligating universal adapters to the dA-tailed DNA fragments to generate a DNA library; normalizing the DNA library; and hybridization capturing dA-tailed DNA fragments in the DNA target regions from the normalized barcoded-DNA library.

The first step involves enzymatic fragmentation of dsDNA, end-repair and dA-tailing, all performed in a single reaction. The fragmentation profile achieved is dependent on both temperature and time. The second step is ligation of the truncated P5 and P7 adapters. The final indexing PCR step facilitates the completion of fully adapted indexed libraries. One protocol to accomplish this that enables equal representation of a plurality of DNA samples in the DNA library is described below.

The Swift® 2S Turbo DNA Library Kits are available in two sizes with reagents (10% excess volume) for the preparation of either 24 or 96 libraries. The method can involve use of a compatible Swift® indexing kit; Magnetic beads for clean-up steps, e.g., SPRIselect™beads (Beckman Coulter, Cat. No. B23317/B23318/B23319); Magnetic rack for clean-up steps, e.g., Invitrogen DynaMag™ or Agencourt® SPRIPlate™; Library quantification kit; Qubit® or other fluorometric-based assays for determining DNA concentration; Microfuge; Programmable thermocycler; PCR tubes; low retention microfuge tubes; Aerosol-resistant, low retention pipettes and tips; 200-proof/absolute ethanol (molecular biology-grade); Nuclease-free water (molecular biology-grade); and PCR reagents (including DNA polymerase) for hybridization capture of choice.

Pre-set the thermocycler according to the program in the order listed below. A heated lid set at 70 °C is preferred for this step. Use the recommendations below to determine the optimal reaction time required to generate the desired fragment size. Reaction times may need to be optimized for individual samples. Prior to mixing, start the program to allow cycler lid to reach 70 °C and temperature block to reach 4 °C Thermocycler Conditions, lid kept at 70 °C: Hold at 4 °C; 32 °C for the desired fragmentation time; 65 °C for about 30 minutes; Hold at 4 °C—proceed to the Ligation step. Add Enzymatic Prep Master Mix to DNA. Mix by vortex, spin down the sample tube in a microfuge, and place in the chilled thermocycler and advance the program to the 32 °C step.

Pre-set the thermocycler program for about 20 minutes at 20 °C with lid heating OFF or set at 40 °C Add pre-mixed Ligation Master Mix to the same tubes in which Enzymatic Prep was performed. Mix by low-to-moderate vortexing.

Place the samples in the thermocycler, programmed at 20 °C for about 20 minutes with lid heating OFF or set at 40 °C Purify the Ligation reaction using a magnetic rack, SPRI bead suspension, and freshly prepared 80% ethanol. At the end of the clean-up, re-suspend the beads in Low EDTA TE buffer. Place the sample tubes on a magnetic rack and wait about 2 minutes. Carefully transfer the supernatant to a clean tube without carrying any beads.

Pre-set the thermocycler with heated lid (105 °C) with a program such as the following: step 1 (98 °C, 30 sec); step 2 (98 °C, 10 sec); step 3 (60° C., 30 sec); step 4 (68° C., 60 sec); go to step 2 for 8 cycles; step 5 (68 °C, 5 min); then hold at 4° C.

Add 1 μl Swift Normalase Unique Dual Index Primer, 5 μl of the pre-mixed Indexing PCR Master Mix to the corresponding eluted sample. Mix by vortexing. Spin down the sample plate and run it in the indexing PCR pre-programmed thermocycler. Samples can be stored in thermocycler overnight at 4 °C.

Mix the sample with beads by moderate vortexing. Pulse spin the samples in a tabletop microcentrifuge. Do not centrifuge to excess, as marked by the beads pelleting at the bottom. If this occurs, re-mix your samples and spin again with less force/shorter duration. Incubate the samples for 5 minutes at room temperature. Place the sample on a magnetic rack until the solution clears and a pellet is formed (approximately 2 minutes). Remove and discard the supernatant without disturbing the pellet (less than 5 μl may be left behind).

Add freshly prepared 80% ethanol solution to the sample while it is still on the magnetic rack. Use care not to disturb the pellet. Incubate for about 30 seconds and then carefully remove the ethanol solution. Repeat step for a second wash with the 80% ethanol solution. Gently spin the samples in a tabletop microfuge and place back on the magnetic rack. Remove any residual ethanol solution from the bottom of the tube using a smaller pipette tip.

Remove samples from magnetic rack. Add Low EDTA TE buffer and re-suspend the pellet. Mix well by pipetting up and down until homogenous. Place the sample tubes on a magnetic rack and wait about 2 minutes. Carefully transfer the sample to a new PCR tube without carry over of any beads.

Pre-set a thermocycler program for 15 minutes at 30 °C with open lid or lid heating OFF. Add Normalase I mix to the DNA library and incubate at 30 °C for about 15 minutes. Pool 5 uL of each sample into one reaction tube.

Pre-set a thermocycler program for 15 minutes at 37 °C with open lid or lid heating OFF. Add Normalase II Master Mix, mix well by vortexing, and spin down the library pools in a microfuge. Place the library pools in the thermocycler and incubate at 37 °C for about 15 min. Following the Normalase II reaction, place the library pools in the thermocycler and incubate at 95 °C less than 2 minutes, add Reagent E1.

Perform the following bead purification steps twice: Mix the sample with beads by moderate vortexing. Pulse spin the samples in a tabletop microcentrifuge. Incubate the samples for 5 minutes at room temperature. Place the sample on a magnetic rack until the solution clears and a pellet is formed (approximately 2 minutes). Remove and discard the supernatant without disturbing the pellet (less than 5 μl may be left behind). Add freshly prepared 80% ethanol solution to the sample while it is still on the magnetic rack. Use care not to disturb the pellet. Incubate for about 30 seconds and then carefully remove the ethanol solution. Repeat step for a second wash with the 80% ethanol solution. Gently spin the samples in a tabletop microfuge and place back on the magnetic rack. Remove any residual ethanol solution from the bottom of the tube using a smaller pipette tip. Remove samples from magnetic rack. Add Low EDTA TE buffer and re-suspend the pellet. Mix well by pipetting up and down until homogenous. Place the sample tubes on a magnetic rack and wait about 2 minutes. Carefully transfer the sample to a new PCR tube without carry over of any beads.

In some embodiments, the DNA library is then hybridization captured using custom capture probes. The following is an example protocol.

Heat the tube containing the Indexed Library Pool (dA-tailed DNA fragments) and blockers at 95 °C for about 5 minutes in a thermal cycler with the lid at 105 °C Cool the Indexed Library Pool and blockers to room temperature on the benchtop (no longer than 5 minutes). Add the custom capture probes to the tube containing the resuspended Indexed Library Pool and blockers. Add Twist® Hybridization Enhancer to each hybridization reaction. Mix thoroughly by gentle pipetting, making sure to not generate bubbles. Seal the pool wells with strip caps. Seal the plate. Pulse-spin to ensure all solution is at the bottom of the tube(s). Incubate the hybridization reaction at 70 °C for about 16 hours in a thermal cycler with the lid at 85 °C.

For each hybridization reaction, preheat Wash Buffer 2 to 48 °C in the dry bath. Equilibrate Streptavidin Binding Beads and DNA Purification Beads to room temperature for at least 30 minutes prior to use. Pre-heat a heat block to 48 °C. Thaw KAPA HiFi HotStart ReadyMix and Amplification Primers on ice. Once reagents are thawed, mix by pulse-vortexing for 2 seconds.

Vortex the pre-equilibrated Streptavidin Binding Beads until mixed. Add Streptavidin Binding Beads to a microcentrifuge tube. Prepare one tube for each hybridization reaction. Add Binding Buffer to the tube(s) and mix by pipetting. Place the tube(s) on a magnetic stand for about 1 minute, then remove and discard the clear supernatant. Make sure to not disturb the bead pellet. Remove the tube from the magnetic stand. Repeat the wash two more times for a total of three washes. After removing the clear supernatant from the third wash, add a final Binding Buffer and resuspend the beads by vortexing until homogenized.

After an about 16-hour hybridization is complete, open the thermal cycler lid and quickly transfer the volume of each hybridization reaction including Twist® Hybridization Enhancer into a corresponding tube of washed Streptavidin Binding Beads.

Mix the tube(s) of hybridization reaction with the Streptavidin Binding Beads for about 30 minutes at room temperature on a shaker, rocker, or rotator at a speed sufficient to keep the solution mixed.

Remove the tube(s) containing the hybridization reaction with Streptavidin Binding Beads from the mixer and pulse-spin to ensure all solution is at the bottom of the tube(s). Place the tube(s) on a magnetic stand for about 1 minute. Remove and discard the clear supernatant including the Twist® Hybridization Enhancer. Do not disturb the bead pellet Remove the tube(s) from the magnetic stand and add room temperature Wash Buffer 1. Mix by pipetting, then pulse-spin to ensure all solution is at the bottom of the tube(s). Transfer the entire volume into a new microcentrifuge tube, one per hybridization reaction. Place the tube(s) on a magnetic stand for about 1 minute. Remove and discard the clear supernatant. Make sure to not disturb bead pellet.

Remove the tube(s) from the magnetic stand and add 48 °C. Wash Buffer 2. Mix by pipetting, then pulse-spin to ensure all solution is at the bottom of the tube(s). Incubate the tube(s) for about 5 minutes at 48 °C in a heat block. Place the tube(s) on a magnetic stand for 1 minute. Remove and discard the clear supernatant. Make sure to not disturb bead pellet. Repeat the wash two more times, for a total of three washes.

After the final wash, remove all traces of supernatant using a pipet. Proceed immediately to the next step. Do not allow the beads to dry. Add water, remove from magnet, and thoroughly mix by pipetting.

Add the PCR master mix to wells of a plate for each sample. Pipet mix the sample and master mix together, avoiding creating bubbles. Seal the plate, pulse spin, transfer to the pre-heated thermal cycler and resume the PCR program. When the thermal cycler program is complete, remove the tube(s) from the block and proceed to purification.

Pulse-spin the PCR Plate. Add homogenized DNA Purification Beads. Mix gently by pipetting. Incubate at room temperature for about 5 minutes. Place the sample on the magnetic stand and wait until the liquid is clear (about 2-5 minutes). Remove and discard of the supernatant. Wash 2 times as follows: add freshly prepared 80% EtOH to each sample; incubate on the magnetic stand for about 30 seconds; remove and discard all the supernatant from each sample. Briefly centrifuge the plate or tube and place back on the magnetic stand. Remove residual EtOH from each sample using a pipette. Air-dry the samples on the magnetic stand until dry. Add Qiagen EB to each well or tube. Remove the plate or tube from the magnetic stand. Mix gently by pipetting. Incubate at room temperature for about 2 minutes. Place the plate or tube on the magnetic stand and wait until the liquid is clear (about 2-5 minutes). Transfer 18 supernatant to the corresponding well of a new plate or tube.

Method for Identifying a Subject with Increased Risk of Developing a Cardiometabolic Disease or a Hematological Cancer Clonal hematopoiesis of indeterminate potential, or CHIP, is a common aging-related phenomenon in which hematopoietic stem cells (HSCs) or other early blood cell progenitors contribute to the formation of a genetically distinct subpopulation of blood cells. As the name suggests, this subpopulation in the blood is characterized by a shared unique mutation in the cells' DNA; it is thought that this subpopulation is "clonally" derived from a single founding cell and is therefore made of genetic "clones" of the founder.

Clonal hematopoiesis by itself is not considered to be a hematologic cancer; nevertheless, evidence is mounting that this condition may adversely affect human health. It has been proposed to label the group of individuals who have clonal hematopoiesis defined by a mutation in a malignancy-associated gene but without evidence of disease (such as cytopenia, dysplasia or immature "blast" cells in the bone marrow) as having CHIP. A clonal involvement (sometimes referred to simply as the size of a "clone") of 2% of the blood has been tentatively proposed as a cutoff, though there is discussion that a lower floor that is more inclusive could also be appropriate. This cutoff may ultimately depend on whether clones must reach a certain size before influencing health. The level at which a clone begins to have a potential clinical impact is an open question, though there is already data to suggest larger clones have a larger effect on health.

The presence of clonal hematopoiesis/CHIP has been shown to increase blood cancer risk and is correlated with an increased risk of mortality overall. This is true both of clonal hematopoiesis with known candidate drivers as well as in cases without such drivers.

One area of health that CHIP has been definitively shown to influence is the risk of progression to blood cancer. In a given year, a tiny fraction of the general population will develop a hematologic cancer such as myelodysplastic syndrome (MDS) or AML; it is estimated that just 3 to 4 people per 100,000 will get MDS in a given year, and 4 people per 100,000 will develop AML. With CHIP, the risk of acquiring a hematologic malignancy like MDS or AML is increased more than 10-fold. Despite this increased risk, people with CHIP are still at low overall risk for developing a blood cancer, with only about 0.5-1.0% transformation per year.

A second area of health that may be affected by CHIP is the risk for heart attack and stroke. A strong association between CHIP and heart attack/ischemic stroke has been identified in multiple human genetic datasets, where CHIP was a stronger predictor of heart attack/stroke than if a patient 1) was a smoker, 2) had hypertension, 3) had high cholesterol, or 4) was overweight. In this study, which shows correlation but not causation, people with CHIP were 2.3 times more likely to suffer a heart attack, or 4.4 times as likely if the variant allele frequency in their blood was greater than 0.10, than matched controls without CHIP. It has also been found that there is an increased risk of cardiovascular mortality in patients who exhibit CHIP and receive self-derived stem cell transplantation. The idea of CHIP having a causal role in human heart attacks/strokes has been given support by a 2017 study that showed impairment of the Tet2 CHIP gene in mice causally led to accelerated atherosclerosis, and this finding in mice has been independently validated. The possibility of somatic mutations in the blood contributing not only to cancer risk but also to heart attack and stroke has generated much discussion in top-level scientific publications and a large multi-cohort study published in 2017 appears to confirm the causal link between CHIP and cardiovascular disease in humans.

In addition to its effects on those who would otherwise be considered healthy, CHIP may have implications in certain disease contexts. It has been shown that patients with CHIP who receive autologous stem cell transplantation (ASCT) as part of their treatment for lymphoma have worse outcomes than patients without CHIP. The poorer prognosis for these patients is due to both an increase in subsequent therapy-related myeloid neoplasms and increased risk for cardiovascular mortality.

There are currently no therapies for slowing or targeting CHIP mutations. Together with the fact that progression from CHIP to outright hematologic malignancy remains infrequent, medical experts have argued against preemptive screening for CHIP but suggest routine follow-up for incidental CHIP findings.

Therefore, in some embodiments, the disclosed scalable multiplex method for amplifying a plurality of target DNA regions is used to capture and sequence the regions listed in Table 1 for the purposes of identifying a subject with increased risk of developing a cardiometabolic disease or a hematological cancer.

TABLE 1

Targeted Capture regions (human reference genome 19 coordinates) for identifying a subject with increased risk of developing a cardiometabolic disease or a hematological cancer

| chr | hg19_start | hg19_end | length | gene |
|---|---|---|---|---|
| 1 | 1737908 | 1737982 | 74 | GNB1 |
| 1 | 1747189 | 1747306 | 117 | GNB1 |
| 1 | 43,814,928 | 43,815,034 | 106 | MPL |
| 1 | 115,256,420 | 115,256,599 | 179 | NRAS |
| 1 | 115,258,668 | 115,258,783 | 115 | NRAS |
| 1 | 154426961 | 154426981 | 20 | IL-6R SNP |
| 2 | 25457142 | 25457294 | 152 | DNMT3A |
| 2 | 25458570 | 25458699 | 129 | DNMT3A |
| 2 | 25459799 | 25459879 | 80 | DNMT3A |
| 2 | 25461993 | 25462089 | 96 | DNMT3A |
| 2 | 25462353 | 25462387 | 34 | DNMT3A |
| 2 | 25463165 | 25463324 | 159 | DNMT3A |
| 2 | 25463503 | 25463604 | 101 | DNMT3A |
| 2 | 25464425 | 25464581 | 156 | DNMT3A |
| 2 | 25466761 | 25466856 | 95 | DNMT3A |
| 2 | 25467018 | 25467212 | 194 | DNMT3A |
| 2 | 25467403 | 25467526 | 123 | DNMT3A |
| 2 | 25468116 | 25468206 | 90 | DNMT3A |
| 2 | 25468883 | 25468938 | 55 | DNMT3A |
| 2 | 25469023 | 25469183 | 160 | DNMT3A |
| 2 | 25469483 | 25469650 | 167 | DNMT3A |
| 2 | 25469914 | 25470032 | 118 | DNMT3A |
| 2 | 25470454 | 25470623 | 169 | DNMT3A |
| 2 | 25470900 | 25471126 | 226 | DNMT3A |
| 2 | 25472520 | 25472598 | 78 | DNMT3A |
| 2 | 25474775 | 25474968 | 193 | DNMT3A |
| 2 | 25475057 | 25475071 | 14 | DNMT3A |
| 2 | 25497804 | 25497961 | 157 | DNMT3A |
| 2 | 25498363 | 25498417 | 54 | DNMT3A |
| 2 | 25505251 | 25505585 | 334 | DNMT3A |
| 2 | 25523002 | 25523117 | 115 | DNMT3A |
| 2 | 25536776 | 25536858 | 82 | DNMT3A |
| 2 | 25,972,558 | 25,973,289 | 731 | ASXL2 |
| 2 | 25,976,401 | 25,976,509 | 108 | ASXL2 |
| 2 | 198264773 | 198264895 | 122 | SF3B1 |
| 2 | 198264970 | 198265163 | 193 | SF3B1 |
| 2 | 198265433 | 198265665 | 232 | SF3B1 |
| 2 | 198266118 | 198266254 | 136 | SF3B1 |
| 2 | 198266460 | 198266617 | 157 | SF3B1 |
| 2 | 198266703 | 198266859 | 156 | SF3B1 |
| 2 | 198267274 | 198267555 | 281 | SF3B1 |
| 2 | 198267667 | 198267764 | 97 | SF3B1 |
| 2 | 198268303 | 198268493 | 190 | SF3B1 |
| 2 | 198269794 | 198269906 | 112 | SF3B1 |
| 2 | 198269993 | 198270201 | 208 | SF3B1 |
| 2 | 198272716 | 198272848 | 132 | SF3B1 |
| 2 | 198273087 | 198273310 | 223 | SF3B1 |
| 2 | 198274488 | 198274736 | 248 | SF3B1 |
| 2 | 198281459 | 198281640 | 181 | SF3B1 |
| 2 | 209,108,248 | 209,108,325 | 77 | IDH1 - hotspot |
| 2 | 209113082 | 209113145 | 63 | IDH1 - hotspot |
| 4 | 55593383 | 55593490 | 107 | KIT |
| 4 | 55593581 | 55593708 | 127 | KIT |
| 4 | 55593988 | 55594093 | 105 | KIT |
| 4 | 55594176 | 55594287 | 111 | KIT |
| 4 | 55595500 | 55595651 | 151 | KIT |
| 4 | 55597493 | 55597585 | 92 | KIT |
| 4 | 55598036 | 55598164 | 128 | KIT |

TABLE 1-continued

Targeted Capture regions (human reference genome 19 coordinates) for identifying a subject with increased risk of developing a cardiometabolic disease or a hematological cancer

| chr | hg19_start | hg19_end | length | gene |
|---|---|---|---|---|
| 4 | 55599235 | 55599358 | 123 | KIT |
| 4 | 55602663 | 55602775 | 112 | KIT |
| 4 | 106155048 | 106158602 | 3554 | TET2 |
| 4 | 106162490 | 106162595 | 105 | TET2 |
| 4 | 106163985 | 106164089 | 104 | TET2 |
| 4 | 106164721 | 106164940 | 219 | TET2 |
| 4 | 106180770 | 106180931 | 161 | TET2 |
| 4 | 106182910 | 106183010 | 100 | TET2 |
| 4 | 106190761 | 106190909 | 148 | TET2 |
| 4 | 106193715 | 106194080 | 365 | TET2 |
| 4 | 106196199 | 106197681 | 1482 | TET2 |
| 6 | 43299507 | 43299595 | 88 | ZNF318 |
| 6 | 43304890 | 43308245 | 3355 | ZNF318 |
| 6 | 43308522 | 43308651 | 129 | ZNF318 |
| 6 | 43309844 | 43309954 | 110 | ZNF318 |
| 6 | 43310408 | 43310622 | 214 | ZNF318 |
| 6 | 43316056 | 43316368 | 312 | ZNF318 |
| 6 | 43320109 | 43320219 | 110 | ZNF318 |
| 6 | 43322396 | 43323888 | 1492 | ZNF318 |
| 6 | 43324858 | 43325508 | 650 | ZNF318 |
| 6 | 43333024 | 43333183 | 159 | ZNF318 |
| 6 | 43336699 | 43337108 | 409 | ZNF318 |
| 9 | 5073683 | 5073800 | 117 | JAK2 - hotspot |
| 11 | 119148870 | 119149012 | 142 | CBL |
| 11 | 119149214 | 119149428 | 214 | CBL |
| 12 | 22,824,199 | 22,824,293 | 94 | ETNK1 |
| 12 | 25,378,546 | 25,378,706 | 160 | KRAS |
| 12 | 25,380,154 | 25,380,358 | 204 | KRAS |
| 12 | 25,398,204 | 25,398,318 | 114 | KRAS |
| 15 | 90631887 | 90631990 | 103 | IDH2 - hotspot |
| 17 | 7572921 | 7573013 | 92 | TP53 |
| 17 | 7573921 | 7574038 | 117 | TP53 |
| 17 | 7576531 | 7576589 | 58 | TP53 |
| 17 | 7576619 | 7576662 | 43 | TP53 |
| 17 | 7576847 | 7576931 | 84 | TP53 |
| 17 | 7577013 | 7577160 | 147 | TP53 |
| 17 | 7577493 | 7577613 | 120 | TP53 |
| 17 | 7578132 | 7578294 | 162 | TP53 |
| 17 | 7578365 | 7578561 | 196 | TP53 |
| 17 | 7579306 | 7579595 | 289 | TP53 |
| 17 | 7579694 | 7579726 | 32 | TP53 |
| 17 | 7579833 | 7579945 | 112 | TP53 |
| 17 | 58733954 | 58734207 | 253 | PPM1D |
| 17 | 58740350 | 58740918 | 568 | PPM1D |
| 17 | 74732867 | 74733065 | 198 | SRSF2 - hotspot |
| 18 | 42,531,868 | 42,531,967 | 99 | SETBP1 |
| 20 | 30946573 | 30946640 | 67 | ASXL1 |
| 20 | 30947544 | 30947599 | 55 | ASXL1 |
| 20 | 30954181 | 30954275 | 94 | ASXL1 |
| 20 | 30956809 | 30956931 | 122 | ASXL1 |
| 20 | 31015925 | 31016056 | 131 | ASXL1 |
| 20 | 31016122 | 31016230 | 108 | ASXL1 |
| 20 | 31017135 | 31017239 | 104 | ASXL1 |
| 20 | 31017698 | 31017861 | 163 | ASXL1 |
| 20 | 31019118 | 31019292 | 174 | ASXL1 |
| 20 | 31019380 | 31019487 | 107 | ASXL1 |
| 20 | 31020677 | 31020793 | 116 | ASXL1 |
| 20 | 31021081 | 31021725 | 644 | ASXL1 |
| 20 | 31022229 | 31025146 | 2917 | ASXL1 |
| 20 | 57484399 | 57484483 | 84 | GNAS |
| 20 | 57484570 | 57484639 | 69 | GNAS |
| 20 | 57484733 | 57484864 | 131 | GNAS |
| 20 | 57485000 | 57485141 | 141 | GNAS |
| 20 | 57485383 | 57485461 | 78 | GNAS |
| 20 | 57485732 | 57485889 | 157 | GNAS |
| 21 | 44513206 | 44513364 | 158 | U2AF1 |
| 21 | 44514571 | 44514678 | 107 | U2AF1 |
| 21 | 44514759 | 44514903 | 144 | U2AF1 |
| 21 | 44515542 | 44515651 | 109 | U2AF1 |
| 21 | 44515798 | 44515858 | 60 | U2AF1 |
| 21 | 44520557 | 44520634 | 77 | U2AF1 |
| 21 | 44521384 | 44521547 | 163 | U2AF1 |
| 21 | 44524419 | 44524517 | 98 | U2AF1 |
| 21 | 44527555 | 44527609 | 54 | U2AF1 |

TABLE 1-continued

Targeted Capture regions (human reference genome 19 coordinates) for identifying a subject with increased risk of developing a cardiometabolic disease or a hematological cancer

| chr | hg19_start | hg19_end | length | gene |
|---|---|---|---|---|
| X | 119387265 | 119389294 | 2029 | ZBTB33 |
| X | 154299802 | 154299925 | 123 | BRCC3 |
| X | 154300601 | 154300618 | 17 | BRCC3 |
| X | 154301651 | 154301706 | 55 | BRCC3 |
| X | 154305444 | 154305564 | 120 | BRCC3 |
| X | 154306890 | 154306978 | 88 | BRCC3 |
| X | 154317537 | 154317626 | 89 | BRCC3 |
| X | 154319058 | 154319114 | 56 | BRCC3 |
| X | 154327589 | 154327664 | 75 | BRCC3 |
| X | 154344331 | 154344463 | 132 | BRCC3 |
| X | 154344985 | 154345029 | 44 | BRCC3 |

In some embodiments, the disclosed method involves the use of the capture probes listed in Table 2.

Therefore, in some embodiments, the capture probe has the nucleic acid sequence: TCCTCCAGTCCC-TACCTTGTTGGTGGTGTAGCTGTCCCAGATGA-TAAGTTTACCATC CTGCGAGGCACTGACGAGAAGCCTGGAGGGACA-GACA (SEQ ID NO:1, >chr1:1737899-1737992), or a fragment thereof at least 8, 10, 12, 14, 16, 18, or 20 nucleotides in length.

Therefore, in some embodiments, the capture probe has the nucleic acid sequence:

```
                  (SEQ ID NO: 2; >chr1: 1747180-1747316)
CATGCCCACGCCTACCTGGAGTCTGTGCCCCAGTGCATGG

CGTAGATCTTGGCCAGGTGCCCCCGCAGTGTCCTCCTCGT

GCGCATTTGGATTCTTCCCACTGGGTCGATGTTGTTTGTG

ATCTTGAAAATAAAAAC.
```

Therefore, in some embodiments, the capture probe has the nucleic acid sequence: TTTTTAACCTAGTGCAAGAT-TCTTCTTCAGTACCACTGCC (SEQ ID NO:3; >chr1: 154426952-154426991), or a fragment thereof at least 8, 10, 12, 14, 16, 18, or 20 nucleotides in length.

Therefore, in some embodiments, the capture probe has the nucleic acid sequence: TTGCCCCCATGTCCCTTA-CACACACGCAAAATACTCCTTCAGCG-GAGCGAAGAGGT GGCGGATGACTGGCACGCTC-CATGACCGGCCCAGCAGTCTCTGCCTCGCCAAGC GGCTCATGTTGGAGACGTCAGTATAGTGGACTGG-GAAACCAAATACCCTGGGGGA GAAAAGG (SEQ ID NO:4; >chr2:25457133-25457304), or a fragment thereof at least 8, 10, 12, 14, 16, 18, or 20 nucleotides in length.

Therefore, in some embodiments, the capture probe has the nucleic acid sequence: GCACAACCCGGGTACCTTTCCATTTCAGTGCAC-CATAAGATGTCCTCTTTCTCATTC ATGAAGACAG-GAAAATGCTGGTCTTTGCCCTGCTTTATG-GAGTTTGACCTCGTAGTA ATGGTCCTCACTTTGCTGAACTAGATGAAGAGGAG (SEQ ID NO:5; >chr2:25458561-25458709), or a fragment thereof at least 8, 10, 12, 14, 16, 18, or 20 nucleotides in length.

Therefore, in some embodiments, the capture probe has the nucleic acid sequence: GACGCTG-GAGCTGACCTTGGCTATCCTGCCATGCTCCA-GACACTCCTGCAGCTCC AGCTTATCATTCACAGTG-GATGCCAACGGCCTAGGAGGCAGAAGA (SEQ ID NO:6; >chr2:25459790-25459889), or a fragment thereof at least 8, 10, 12, 14, 16, 18, or 20 nucleotides in length.

Therefore, in some embodiments, the capture probe has the nucleic acid sequence: GGAGCTTTCAC-CAACCTGTTCATACCGGGAAGGT-TACCCCAGAAGTAGCGGGCCC TGTGTGCAGCTGACACTTCTTTGGCATCAATCAT-CACAGGGTTGGACTACAAAACA GGAGA (SEQ ID NO:7; >chr2:25461984-25462099), or a fragment thereof at least 8, 10, 12, 14, 16, 18, or 20 nucleotides in length.

Therefore, in some embodiments, the capture probe has the nucleic acid sequence: GTGGCCACTAGCC-CACTAGTACAGGTGGCTATTTGTACCTAAAAT-GAGGCCAA (SEQ ID NO:8; >chr2:25462344-25462397), or a fragment thereof at least 8, 10, 12, 14, 16, 18, or 20 nucleotides in length.

Therefore, in some embodiments, the capture probe has the nucleic acid sequence: GGTTGCTGGC-TATACCTCGAGAAATCGCGAGATGTCCCTCTTGT-CACTAACGCCCA TGGCCACCACATTCT-CAAAGAGCCAGAAGAAGGGGCGATCATCTCCCTC-CTTGGG CCGCGCATCATGCAG-GAGGCGGTAGAACT-CAAAGAAGAGCCGGCCAGTGCCCTCT GAGAGGTCGGAAG (SEQ ID NO:9; >chr2:25463156-25463334), or a fragment thereof at least 8, 10, 12, 14, 16, 18, or 20 nucleotides in length.

Therefore, in some embodiments, the capture probe has the nucleic acid sequence: CAGGATGGTACC-TACCGTAGAGGCCCTTGCGAGCAGGGTTGAC-GATGGAGAGGTC ATTGCAGGGACTGCCCCCAAT-CACCAGATCGAATGGGCCCCACTCCTGGATCTGG GAGGATAAAGG (SEQ ID NO:10; >chr2:25463494-25463614), or a fragment thereof at least 8, 10, 12, 14, 16, 18, or 20 nucleotides in length.

Therefore, in some embodiments, the capture probe has the nucleic acid sequence: ACAGCATGGACATA-CATGCTTCTGTGTGACGCTGCGGACGTCCCCGAC-GTACATGA TCTTCCCCTGGTGCCGCACCATGCC-CACCGTGATGGAGTCCTCACACACCTCCGA GGCAATGTAGCGGTCCACCTGAATGCC-CAAGTCCTTCAGCACCAGGAGCCCTGCA CCAGCCAGCA (SEQ ID NO:11; >chr2:25464416-25464591), or a fragment thereof at least 8, 10, 12, 14, 16, 18, or 20 nucleotides in length.

Therefore, in some embodiments, the capture probe has the nucleic acid sequence: GCCTGCACCCCT-CACCTGTAGCGATTCCATCAAAGAGA-GACAGCACCCGGATGGG CTTCCTCTTCTCAGCTGGGACAGGTGGGTAAA-CCTTTGGAGGGTCCTAAGCAGTGA GCAC (SEQ ID NO:12; >chr2:25466752-25466866), or a fragment thereof at least 8, 10, 12, 14, 16, 18, or 20 nucleotides in length.

Therefore, in some embodiments, the capture probe has the nucleic acid sequence: AGGCCCAGCACTCACAAAT-TCCTGGTCGTGGTTATTAGCGAAGAACATCTG-GAGCC GGGAGGGCCAGTCCT-CTCGCCGCCGCAGCAGCCCGTAGGTACCCTTGT-GCCCGC ACATGTAGCAGTTCCAGGGGTCTTCCT-TAATGGCTGCCTGGGCAGCCCCCGGCCC CAC-CAAGAGGTCCACACACTCCACGCAAAAGCACCTG-GAAGGAGACCCA (SEQ ID NO:13; >chr2:25467009-25467222), or a fragment thereof at least 8, 10, 12, 14, 16, 18, or 20 nucleotides in length.

Therefore, in some embodiments, the capture probe has the nucleic acid sequence: CCACAACAGCCT-CACCTGCAGCAGTTGTTGTTTCCGCACAT-GAGCACCTCACGGCC CCCACAGCA-GATGGTGCAGTAGGACTGGTAGCCGTCGTCGTC-GTACTGGTACGCA CACTCCAGAAAGCAGTTCTA-GACAGCAGCGGG (SEQ ID NO:14; >chr2:25467394-25467536), or a fragment thereof at least 8, 10, 12, 14, 16, 18, or 20 nucleotides in length.

Therefore, in some embodiments, the capture probe has the nucleic acid sequence: TGGGTGTGCTCC-TACCTTGCAGTTTTGGCACATTCCTC-CAACGAAGAGGGGGTGTT CCAGGGTAACATT-GAGGCTCCCACAGGAGATGCAGATGTCTGGAA-AGCAGAGGG (SEQ ID NO:15; >chr2:25468107-25468216), or a fragment thereof at least 8, 10, 12, 14, 16, 18, or 20 nucleotides in length.

Therefore, in some embodiments, the capture probe has the nucleic acid sequence: AGGCAACAAACTTACCCT-CAATGTTCCGGCACTTCTGCCGCACCTCGTA-CACCAGC CGCTCTGCAAGGGGAGGAG (SEQ ID NO:16; >chr2:25468874-25468948), or a fragment thereof at least 8, 10, 12, 14, 16, 18, or 20 nucleotides in length.

Therefore, in some embodiments, the capture probe has the nucleic acid sequence: AAGCAGGCCAAC-TACCTCTTGTGCGCTCAT-CAATAATCTCCTTGACCTTGGGCTTCT CCGCTGTGCTCTTCCGGGGCTTTTTGGCTGGTG-GAGGTGGTGCGTAGGCAGCTGC CTCAGGTTC-CACCCACATGTCCGTGTACACTTCTTTGTAGGGAT-TCTTCTCTTCTGG AGGAGGAAAGC (SEQ ID NO:17; >chr2:25469014-25469193), or a fragment thereof at least 8, 10, 12, 14, 16, 18, or 20 nucleotides in length.

Therefore, in some embodiments, the capture probe has the nucleic acid sequence: GGTGCCCTCATT-TACCTTCTGGTGGCTCCAGGCCCT-TAGGGCCAGAAGGCTGGAA GCCCCCCAGGGCC-CATTCAATCATGGGCTTGTTCTGCACCTCCACG-GCCTTGGCA GTGTCACTCT-CATCGCTGTCGTGGCACACCGG-GAACAGCTTCCCCGCGCGGCTGC TGGCCACCTG-GAGGGTGACACG (SEQ ID NO:18; >chr2:25469474-25469660), or a fragment thereof at least 8, 10, 12, 14, 16, 18, or 20 nucleotides in length.

Therefore, in some embodiments, the capture probe has the nucleic acid sequence: AGCAGGGACACT-CACCTGCAGGACCTCGTAGATGGCTTTGCGGTA-CATGGGCTGC TTGTTGTACGTGGCCTGGTG-GAACGCACTGCAAAACGAGCTCAGCGGCATCAGCT TCTCAACACACACCTGGGGGGACAAGCC (SEQ ID NO:19; >chr2:25469905-25470042), or a fragment thereof at least 8, 10, 12, 14, 16, 18, or 20 nucleotides in length.

Therefore, in some embodiments, the capture probe has the nucleic acid sequence: AACCCCACAACTTACCACT-GAGAATTTGCCGTCTCCGAACCA-CATGACCCAGCGGG TGCCTTCAGCTGCTCGGCTCCGGCCCGTCATCCAC-CAAGACACAATGCGGCCTGG CCACCAG-GAGAAGCCCCGCAGTTTCCCCCACACCAGCTCCC-CAATGCCAAAGCCC CGGCCGTCCTGGAGCCCCAAGGA (SEQ ID NO:20; >chr2:25470445-25470633), or a fragment thereof at least 8, 10, 12, 14, 16, 18, or 20 nucleotides in length.

Therefore, in some embodiments, the capture probe has the nucleic acid sequence:

```
(SEQ ID NO: 21; >chr2: 25470891-25471136)
GAAGAAGCCGCTCACCTCGTACTCTGGCTCGTCATCGCCT

GCTTTGGTGGCATTCTTGTCCCCAGCATCGGACCCCACGG
```

-continued

```
GCTCAGGCGTGGTAGCCACAGTGGGGGATGCGGGGTCAGT

GGGCTGCTGCACAGCAGGAGGGCTGGCCTCCTCCACCTTC

TGAGACTCCCCGGGCCCCTGGTTTTCTTCCACAGCATTCA

TTCCTGCAATGACCTTGGCTTTCTTCTCAGCCTGGGGAAA

CAAAAA,
```

or a fragment thereof at least 8, 10, 12, 14, 16, 18, or 20 nucleotides in length.

Therefore, in some embodiments, the capture probe has the nucleic acid sequence: CCTCCATCCTTTCACCGTAT-CACACTCGTCTTTCAGGCTACGATCCACGCGCC-CATT CCTTCTCACAACCCGCTCCAGGATCCCTA-CAAAGGAGAATG (SEQ ID NO:22; >chr2:25472511-25472608), or a fragment thereof at least 8, 10, 12, 14, 16, 18, or 20 nucleotides in length.

Therefore, in some embodiments, the capture probe has the nucleic acid sequence: CCAGCCTGCAGTTAC-CACTGCCCGGGCTCCCGGCCGGCTGCTCTTCCTG-TCCCCC GAGGGCGCCAGGTGCCACTG-GAGCCCTCGAGGAGTGGGGCCTTGGGGCTCGTGG GCAGGAAGGCGGCGGGCCAGCACTAAGTCAG-CATCTCCAGAACTCGGGCCAGGC CGGGACGCCGCGGCTGCTGCGGGCCGGGGAGG-CATACTTCACTCTTTTCA (SEQ ID NO:23; >chr2:25474766-25474978), or a fragment thereof at least 8, 10, 12, 14, 16, 18, or 20 nucleotides in length.

Therefore, in some embodiments, the capture probe has the nucleic acid sequence: CGTCCAGGAACCTACCCAT-AAGGCCAGGTGCAGC (SEQ ID NO:24; >chr2:25475048-25475081), or a fragment thereof at least 8, 10, 12, 14, 16, 18, or 20 nucleotides in length.

Therefore, in some embodiments, the capture probe has the nucleic acid sequence: CAGAAGGCGCCT-CACCTCCCTTTTCCAGCGTGCCAGC-CACTCGTCCCGCTTGCGC TTGCT-GATGTAGTAGGGGTCCCCCGCCTGGAAGGTGAG-CCTCGGCATGGGCCGCT GACG-GAGGCTGGACTCCCAGCCCAAGC-CACCCCGCAGCCGGCCCCGGGAGCCCT AGGACAGAGAGAC (SEQ ID NO:25; >chr2:25497795-25497971), or a fragment thereof at least 8, 10, 12, 14, 16, 18, or 20 nucleotides in length.

Therefore, in some embodiments, the capture probe has the nucleic acid sequence: GGGTGGAACACTTGCCTC-CATTTTCATGGATTC-GATGTTGGTCTCCTTCTGTTCTTT GCCTGTG-GAGAGGGAAG (SEQ ID NO:26; >chr2:25498354-25498427), or a fragment thereof at least 8, 10, 12, 14, 16, 18, or 20 nucleotides in length.

Therefore, in some embodiments, the capture probe has the nucleic acid sequence: CCAAGTCCCTGACTCTCAGGGTATGCTGGTGG-GCCCAGAAGAGGCTGCCCCTGGT GCTGAGGACT-CACCCGCTTCTGCAGGGGCTCCTCGGCCCTC-CTTGGGGGTGCAG CAGCCATTTTCCACTGCTCTT-GAGGCTTCAGGCAGGGTCTCAGCTGCACCCTCTCC CTCTGCTGGGGCCCCGCCCTTCTGCCCCCCAGC-AGGGCTCCCCTCCTCTGGCTGG GGCT-CACTCCGCTTCTCCAAGTCCCCAT-TGGGTAATAGCTCTGAGGCGCCTGAGTC CTGGGC-CATGGATGGGGACTTGGAGATCACCGCAGGG-TCCTTTGGCGTGTCACCG CTTTC-CACCTGCAAATGTAAGAA (SEQ ID NO:26; >chr2:25505242-25505595), or a fragment thereof at least 8, 10, 12, 14, 16, 18, or 20 nucleotides in length.

Therefore, in some embodiments, the capture probe has the nucleic acid sequence: GGATGTGACACT-CACCGGGGGGTGCTTGCGCTTCCTCCCAGGCC-GCCCCACCTTC CGTGCCGTGGTGCTGGGCTCTTGGCGCTCCTCC-TTGCCACGCGGCTCCTCCTGCT CCTCTCCGTCCTGCAGGCACAGACA (SEQ ID NO:27; >chr2:25522993-25523127), or a fragment thereof at least 8, 10, 12, 14, 16, 18, or 20 nucleotides in length.

Therefore, in some embodiments, the capture probe has the nucleic acid sequence: GAGCCCGCTGCT-CACCTTTCGGTCCTCCTCCCGCTCCGCAGCAGA-GCTGCTGGTG TCCCCGGGGCCGCTGGAGGG-CATGGCGGGCATCTGGGCGCCGGGAGG (SEQ ID NO:28; >chr2:25536767-25536868), or a fragment thereof at least 8, 10, 12, 14, 16, 18, or 20 nucleotides in length.

Therefore, in some embodiments, the capture probe has the nucleic acid sequence: CAGCAAATTCCATACC-TATGACATTTACAATGGCCTTCAGTGCTC-CAAGAATGCTGC CCAATACTTCAGGGTACTCTT-CACCCAAATACTCATACAATACAACACCCAAGTGTC CCATCAATTTTTCCTATAATAAAACAAA (SEQ ID NO:29; >chr2:198264764-198264905), or a fragment thereof at least 8, 10, 12, 14, 16, 18, or 20 nucleotides in length.

Therefore, in some embodiments, the capture probe has the nucleic acid sequence: GATGCAAAAGTT-TACCTCTTGACAAGTCTT-CATGACAACAGCAGTTCGAGAAATCAA GTCAGCTGCCTGTTGCCTAACTTTAGCAGATTTGTT-ATTTAAACGCCACAAAACTGT ACCACAGATCT-GAGGCAAGTATGGTTTGACTCGTTTGCCAAGAG-CATTAACCACTG TGCCAAAGCCGTTCAACATTACT-GAGTCCTAAAAAATAAATTT (SEQ ID NO:30; >chr2:198264961-198265173), or a fragment thereof at least 8, 10, 12, 14, 16, 18, or 20 nucleotides in length.

Therefore, in some embodiments, the capture probe has the nucleic acid sequence: AATAGTTTTCAT-TACCTCTGTAGTCTGTTCTTGGAAAGCAT-AAAGAATACCATCAATC AGTTGTTCTTCAAGTTTAT-GATCAATATCTGCTGCTCCCAAATTACCCATAAT-TTTCT CAATTGTCTCCATCACCAT-TTTTCTGTACTGTTCGGCTTCATCTTTCAGATCATC-CAC AATCCTGGATATAATTTCTGCTGCACC-TACTTTGTTTGCCAACTCCACAGTAGTATC AACTAACTAAAAAGAACAGAA (SEQ ID NO:31; >chr2:198265424-198265675), or a fragment thereof at least 8, 10, 12, 14, 16, 18, or 20 nucleotides in length.

Therefore, in some embodiments, the capture probe has the nucleic acid sequence: ACAATAAAAGCT-TACCTGTCGGTAATTTCTTCTATCCAAAGC-CATCCTGTGCTGCCA GAAGTGTTTAAAAAAGG-GAGGAAGAATCTCTGTTTTAATGTAGTTTGCTT-CTACACC ATCTGTCCCACAACACTGTTTTAC-CACCTAAAAGGTTAAGAA (SEQ ID NO:32; >chr2:198266109-198266264), or a fragment thereof at least 8, 10, 12, 14, 16, 18, or 20 nucleotides in length.

Therefore, in some embodiments, the capture probe has the nucleic acid sequence: ATCTGGAATAAT-TACCTTCAGCACAATTTTTTTCATTTCCTCATCAG-GAGACTGGAAT TCTCGAATAAGGATTAACAT-CACTTCTCTAGTATAGTAGTTGGCATATTCTGC-ATCCA TAAGAGGAATAAGATACCCAATAGCCTT-CAAGAAAGCAGCCAAACCCTATTTTTAAA TAAA (SEQ ID NO:33; >chr2:198266451-198266627), or a fragment thereof at least 8, 10, 12, 14, 16, 18, or 20 nucleotides in length.

Therefore, in some embodiments, the capture probe has the nucleic acid sequence: AATTGGTGGATT-TACCTTTCCTCTGTGTTGGCGGATACCCTTCCAT-AAAGGCTTTAA CACAGAATCAAAAGATTCGATAC-CATAAGGAGTTGCTGCTTCAGCCAAGGCAGCAA TGGCCAAAGCACT-GATGGTCCGAACTTTCTGCTGCTCATCCACAA-GACCTACAAAA CCAAACA (SEQ ID NO:34; >chr2:198266694-198266869), or a fragment thereof at least 8, 10, 12, 14, 16, 18, or 20 nucleotides in length.

Therefore, in some embodiments, the capture probe has the nucleic acid sequence: TACATTACAACTTAC-CATGTTCAATGATTTCAACTAAACTTCTAA-GATGTGGCAAGAT GGCACAGCCCATAAGAATAGC-TATCTGTTGTACAATCTTAATACCAGTGTGTCTCGC TTGCCAGGACTTCTTGCTTTTGCACACAGCTTT-TAAGAAGGGCAATAAAGAAGGAAT GCCCAGGGCAGAGGCTA-CAACAGCAAAAGCTCTAGCTGTTGTGTTACGGA-CATACT CATCCATGTTATCTATATCAGGTCT-CATGGTAGAGATCATAGTAGCCAGACCAGCAG CCTAAAATGTAAACAA (SEQ ID NO:35; >chr2:198267265-198267565), or a fragment thereof at least 8, 10, 12, 14, 16, 18, or 20 nucleotides in length.

Therefore, in some embodiments, the capture probe has the nucleic acid sequence: ATTAAATGTAAATACCTTTGCCAAATTAGAAAT-GATCTCTCGGCCTTCCACTCTAGCA TAGTAATCTT-CATCAATCAATAGCGGTTCAATGACCACGAG-GATCTGAAAAAGAGAA AA (SEQ ID NO:36; >chr2:198267658-198267774), or a fragment thereof at least 8, 10, 12, 14, 16, 18, or 20 nucleotides in length.

Therefore, in some embodiments, the capture probe has the nucleic acid sequence: TTAAGGAGAACAAACCT-TATGCACATATGGACGAACTAAGTCAT-CAAGTTTGTACAG TATCCTATCAATAACTTT-CACAAGTAAATGACGCTCTTGATCCTCAAGTG-TAGGAGA CATCAGCAGAGGAAGAATCTGAT-TAAACAAAGGACCAGCTCCAAATTCACGAGCTT TATCAGTAATCTGACGCAATGCAGCCTGG-GAAAAAGAGCA (SEQ ID NO:37; >chr2:198268294-198268503), or a fragment thereof at least 8, 10, 12, 14, 16, 18, or 20 nucleotides in length.

Therefore, in some embodiments, the capture probe has the nucleic acid sequence: CAAACTGGGACT-TACCTTTCTCATTGGTGGTGTTCCATTCTTAATTTT-TAAAAGCAAC TTCATTAT-TTTTCTCTCTTTTTGCTCTTCTGGACTAAGTGTTGAT-TCATCAACATCAAC CTATAGTAAAAAGAA (SEQ ID NO:38; >chr2:198269785-198269916), or a fragment thereof at least 8, 10, 12, 14, 16, 18, or 20 nucleotides in length.

Therefore, in some embodiments, the capture probe has the nucleic acid sequence: GCTAGTATCACTTAC-CAATAGTTTATCAAAGTATTGAATATCATCAGGTTT-TAAAAAT GGAAGATTTCCAGATGGCTGGTCAT-TAACACTTTTCATAGTTCGATCTTCAGTTTGC ATGTGGAAACCAGTCATACCACCCAAAGGTGTTG-GAGTAGCTGTCAGCTTTCGAGC TGGAGTTCGAATAGGAACATAACCAGCTGGAG-GAGGAAGTACCTAATAAAAGTTAT A (SEQ ID NO:39; >chr2:198269984-198270211), or a fragment thereof at least 8, 10, 12, 14, 16, 18, or 20 nucleotides in length.

Therefore, in some embodiments, the capture probe has the nucleic acid sequence: AATTTGATGTACTACCT-TATATCCTTCTGGGAACATAGCATCTAATTCCT-CATCAGAA AGTGGGCGATTTCTCTCATCAAT-TTCTCTTTCCCACCGCCAAGCCTGAAGCTGTTCA GGAGTCATACTCATTATGTGACCTAC-CAAGAAAAGCA (SEQ ID N0:40; >chr2:198272707-198272858), or a fragment thereof at least 8, 10, 12, 14, 16, 18, or 20 nucleotides in length.

Therefore, in some embodiments, the capture probe has the nucleic acid sequence: ATGAGACAGTTCTACCTG-GAGTAGGGGTAGCCATGTTCATGGCTGGTGTGC-CAATT GGTGTCTTTCCAGGGGTCAGAACTG-GAGTGCTTCCACCCATCTGACTAGCTGGTGT TTCATCCCACCGTGATTTTCTTTTACTGGCTCCAG-GAGTCGGTGTTTCACCAATAGA ATCTCCACCTC-GATCTGTTCGAGGAGTCTCAGCCCATCCACTTC-CATGCCCAGGAG TATCTTTAAAAAGAAAGA (SEQ ID NO:41; >chr2:198273078-198273320), or a fragment thereof at least 8, 10, 12, 14, 16, 18, or 20 nucleotides in length.

Therefore, in some embodiments, the capture probe has the nucleic acid sequence: CTC-CACTAGAAGTACCTCTCTCTGTTTTGGGGGTTT-CATCCCATCTGTTTTTACGAG CACTG-GAAGTTGCGCCTCCATGGCCTGGTGTCGCATGG-CCTGGTGTATCACCTCG TCCAG-GAGTAGCAGCTCCCGCTGGTGTGTGGCTAGGTGT-AGGATCCCATATTTTTG AGCCTGGGGTTGCTCCAG-GAGTCTCGCTTCCCTTTGCACGACCTGGTGTCT-CATCC CATCTTAAGGAAG-GAGTATGCCCAGGGGTCTTAAAAAAGCAAAA (SEQ ID NO:42; >chr2:198274479-198274746), or a fragment thereof at least 8, 10, 12, 14, 16, 18, or 20 nucleotides in length.

Therefore, in some embodiments, the capture probe has the nucleic acid sequence: ACAAAAAGAAAT-TACCTCTGCCTGATCCCAACTTGATAGTTTTTTGG-GAGTGGCACC AGGAGTCTGATCAGCTGTTT-GATCCCAACGCCGTTTTCGTTTTGATGGAGGCTGGG ACGCTGCTGCTCCATTGACGACTTT-TAGTTCTCCAGCTTTAGCTTTTTCTGCTAGCT GTTGCCTAATTTCTCGCTGAAAAAAACAGTG (SEQ ID NO:43; >chr2:198281450-198281650), or a fragment thereof at least 8, 10, 12, 14, 16, 18, or 20 nucleotides in length.

Therefore, in some embodiments, the capture probe has the nucleic acid sequence: TTATTGCCAACATGACT-TACTTGATCCCCATAAGCATGACGACCTATGATGA-TAGGT TTTACCCATCCACTCACAAGCCGGGG (SEQ ID NO:44; >chr2:209113073-209113155), or a fragment thereof at least 8, 10, 12, 14, 16, 18, or 20 nucleotides in length.

Therefore, in some embodiments, the capture probe has the nucleic acid sequence: TCCATTGTAGAGCAAATC-CATCCCCACACCCTGTTCACTCCTTTGCTGAT-TGGTTTC GTAATCGTAGCTGGCATGATGTGCATTAT-TGTGATGATTCTGACCTACAAATATTTA CAGGTAACCATTT (SEQ ID NO:45; >chr4:55593374-55593500), or a fragment thereof at least 8, 10, 12, 14, 16, 18, or 20 nucleotides in length.

Therefore, in some embodiments, the capture probe has the nucleic acid sequence: CTCCCCACAGAAACC-CATGTATGAAGTACAGTGGAAGGTTGTTGAG-GAGATAAATG GAAACAATTATGTTTACATAGACC-CAACACAACTTCCTTATGATCACAAATGGGAGT TTCCCAGAAACAGGCTGAGTTTTGGTCAGTATGA (SEQ ID NO:46; >chr4:55593572-55593718), or a fragment thereof at least 8, 10, 12, 14, 16, 18, or 20 nucleotides in length.

Therefore, in some embodiments, the capture probe has the nucleic acid sequence: CTTCCTACAGG- GAAAACCCTGGGTGCTGGAGCTTTCGG- GAAGGTTGTTGAGGCAA CTGCTTATGGCTTAAT- TAAGTCAGATGCGGCCATGACTGTCGCTGTAAAG- ATGCTC AAGCGTAAGTTCCT (SEQ ID NO:47; >chr4: 55593979-55594103), or a fragment thereof at least 8, 10, 12, 14, 16, 18, or 20 nucleotides in length.

Therefore, in some embodiments, the capture probe has the nucleic acid sequence: CCAATTTTAGCGAGTGCC- CATTTGACAGAACGGGAAGCCCTCATGTCTGAACT- CAAAGTCCTGAGTTACCTTGGTAATCACATGAATAT- TGTGAATCTACTTGGAGCCTGCAC CATTGGAGGTAAAGCCGT (SEQ ID NO:48; >chr4: 55594167-55594297), or a fragment thereof at least 8, 10, 12, 14, 16, 18, or 20 nucleotides in length.

Therefore, in some embodiments, the capture probe has the nucleic acid sequence: GTGCTTTTAGGGCC- CACCCTGGTCATTACAGAATATTGTTGCTATGGT- GATCTTTTG AATTTTTTGAGAAGAAAACGTGATT- CATTTATTTGTTCAAAGCAGGAAGATCATGCA GAAGCTGCACTTTATAAGAATCTTCTGCATT- CAAAGGAGTCTTCCTGGTAAGACTGA (SEQ ID NO:49; >chr4:55595491-55595661), or a fragment thereof at least 8, 10, 12, 14, 16, 18, or 20 nucleotides in length.

Therefore, in some embodiments, the capture probe has the nucleic acid sequence: TCTCTCCCAGCAGCGA- TAGTACTAATGAGTACATGGACATGAAACCTG- GAGTTTCTT ATGTTGTCCCAAC- CAAGGCCGACAAAAGGAGATCTGTGAGAATAGG- TGAGTACCT (SEQ ID NO:50; >chr4:55597484- 55597595), or a fragment thereof at least 8, 10, 12, 14, 16, 18, or 20 nucleotides in length.

Therefore, in some embodiments, the capture probe has the nucleic acid sequence: TTCCTCACAGGCTCATACAT- AGAAAGAGATGTGACTCCCGCCATCATGGAG- GATGA CGAGTTGGCCCTAGACTTAGAAGACTTGCT- GAGCTTTTCTTACCAGGTGGCAAAGG GCATGGCTTTCCTCGCCTC- CAAGAATGTAAGTGGGA (SEQ ID NO:51; >chr4: 55598027-55598174), or a fragment thereof at least 8, 10, 12, 14, 16, 18, or 20 nucleotides in length.

Therefore, in some embodiments, the capture probe has the nucleic acid sequence: AACCTAATAGTGTATT- CACAGAGACTTGGCAGCCAGAAATATCCTCCT- TACTCATGG TCGGATCACAAAGATTTGTGAT- TTTGGTCTAGCCAGAGACATCAAGAATGATTCTAA TTATGTGGTTAAAGGAAACGTGAGTACCC (SEQ ID NO:52; >chr4:55599226-55599368), or a fragment thereof at least 8, 10, 12, 14, 16, 18, or 20 nucleotides in length.

Therefore, in some embodiments, the capture probe has the nucleic acid sequence: TCTATTACAGGCTCGAC- TACCTGTGAAGTGGATGGCACCTGAAAGCATTTT- CAACT GTGTATACACGTTT- GAAAGTGACGTCTGGTCCTATGGGATTTTTCTTTGG- GAGCTGT TCTCTTTAGGTAAAATGAT (SEQ ID NO:53; >chr4:55602654-55602785), or a fragment thereof at least 8, 10, 12, 14, 16, 18, or 20 nucleotides in length.

Therefore, in some embodiments, the capture probe has the nucleic acid sequence: TTCCATGCTCTTTAGAATT- CAACTAGAGGGCAGCCTTGTG- GATGGCCCCGAAGCAA GCCTGATGGAACAGGA- TAGAACCAACCATGTTGAGGGCAACAGACTAAGTC- CATTC CTGATACCATCACCTCCCATTTGCCA- GACAGAACCTCTGGCTACAAAGCTCCAGAA TGGAAGCCCACTGCCTGAGAGAGCT- CATCCAGAAGTAAATGGAGACACCAAGTGG CACTCTTTCAAAAGTTATTATGGAATACCCTGTAT- GAAGGGAAGCCAGAATAGTCGT GTGAGTCCTGACTTTACACAAGAAAGTAGAGGGT- ATTCCAAGTGTTTGCAAAATGG AGGAATAAAACGCACAGTTAGT- GAACCTTCTCTCTCTGGGCTCCTTCAGATCAAGAA ATTGAAACAAGACCAAAAGGCTAATGGAGAAA- GACGTAACTTCGGGGTAAGCCAAG AAAGAAATCCAGGTGAAAGCAGTCAAC- CAAATGTCTCCGATTTGAGTGATAAGAAA GAATCTGTGAGTTCTGTAGCCCAAGAAAATGCAGT- TAAAGATTTCACCAGTTTTTCA ACACAT- AACTGCAGTGGGCCTGAAAATCCAGAGCTTCA- GATTCTGAATGAGCAGGA GGGGAAAAGTGCTAATTACCATGACAAGAACAT- TGTATTACTTAAAAACAAGGCAGT GCTAATGCCTAATGGTGCTA- CAGTTTCTGCCTCTTCCGTGGAACACACA- CATGGTG AACTCCTGGAAAAAACACTGTCTCAAT- ATTATCCAGATTGTGTTTCCATTGCGGTGC AGAAAACCACATCTCACATAAATGCCAT- TAACAGTCAGGCTACTAATGAGTTGTCCT GTGAGATCACTCACCCATCGCATACCTCAGGGCA- GATCAATTCCGCACAGACCTCT AACTCT- GAGCTGCCTCCAAAGCCAGCTGCAGTGGTGAGT- GAGGCCTGTGATGCTG ATGATGCTGA- TAATGCCAGTAAACTAGCTGCAATGCTAAATACC- TGTTCCTTTCAGA AACCAGAACAACTA- CAACAACAAAAATCAGTTTTTGAGATATGCC- CATCTCCTGCAG AAAATAACATCCAGGGAAC- CACAAAGCTAGCGTCTGGTGAAGAATTCTGTTC- AGGT TCCAGCAGCAAT- TTGCAAGCTCCTGGTGGCAGCTCTGAACGGTATT- TAAAACAAAA TGAAATGAATGGTGCTTACTT- CAAGCAAAGCTCAGTGTTCACTAAGGATTCCTTTTC TGCCACTACCACACCACCACCACCATCACAAT- TGCTTCTTTCTCCCCCTCCTCCTCT TCCACAGGTTCCTCAGCTTCCTTCAGAAGGAAA- AAGCACTCTGAATGGTGGAGTTT TAGAAGAACAC- CACCACTACCCCAACCAAAGTAACACAACACTTT- TAAGGGAAGTG AAAATAGAGGGTAAACCT- GAGGCACCACCTTCCCAGAGTCCTAATCCATCT- ACACA TGTATGCAGCCCTTCTCCGATGCTTTCT- GAAAGGCCTCAGAATAATTGTGTGAACAG GAATGACATACA- GACTGCAGGGACAATGACTGTTCCATTGTGTTCT- GAGAAAACAA GACCAATGTCAGAACACCT- CAAGCATAACCCACCAATTTTTGGTAGCAGTGG- AGAG CTACAGGACAACTGCCAGCAGTTGAT- GAGAAACAAAGAGCAAGAGATTCTGAAGGG TCGA- GACAAGGAGCAAACACGAGATCTTGTGCCCC- CAACACAGCACTATCTGAAAC CAGGATGGATT- GAATTGAAGGCCCCTCGTTTTCACCAAGCGGA- ATCCCATCTAAAA CGTAATGAGGCATCACTGCCAT- CAATTCTTCAGTATCAACCCAATCTCTCCAATCAA ATGACCTCCAAACAATACACTGGAAATTCCAA- CATGCCTGGGGGGCTCCCAAGGCA AGCTTA- CACCCAGAAAACAACACAGCTGGAGCACAAGT- CACAAATGTACCAAGTTG AAATGAATCAAGGGCAGTCCCAAGGTA- CAGTGGACCAACATCTCCAGTTCCAAAAA CCCT- CACACCAGGTGCACTTCTCCAAAACAGACCATT-TACCAAAAGCTCATGTGCA GTCACTGTGTGGCACTAGATTTCATTTT-CAACAAAGAGCAGATTCCCAAACTGAAAA ACT-TATGTCCCCAGTGTTGAAACAGCACTTGAAT-CAACAGGCTTCAGAGACTGAGC CATTTTCAAACTCACACCTTTTGCAACATAAGCCT-CATAAACAGGCAGCACAAACAC AAC-CATCCCAGAGTTCACATCTCCCT-CAAAACCAGCAACAGCAGCAAAAATTACAAA TAAAGAATAAAGAGGAAATACTCCAGACTTTTCCT-CACCCCCAAAGCAACAATGATC AGCAAAGAGAAGGATCATTCTTTGGCCA-GACTAAAGTGGAAGAATGTTTTCATGGT GAAAATCAGTATTCAAAATCAAGCGAGTTCGA-GACTCATAATGTCCAAATGGGACTG GAGGAAGTA-CAGAATATAAATCGTAGAAATTCCCCTTATAGTCA-GACCATGAAATCA AGTGCATGCAAAATACAGGTTTCTTGTT-CAAACAATACACACCTAGTTTCAGAGAAT AAAGAACAGACTACACATCCTGAACTTTTTGCAG-GAAACAAGACCCAAAACTTGCAT CACATGCAATAT-TTTCCAAATAATGTGATCCCAAAGCAAGATCTTCTT-CACAGGTGC TTTCAAGAACAGGAGCAGAAGT-CACAACAAGCTTCAGTTCTACAGGGATATAAAAAT AGAAACCAAGATATGTCTGGT-CAACAAGCTGCGCAACTTGCTCAGCAAAGGTACTT GATACATAAC-CATGCAAATGTTTTTCCTGTGCCTGACCAGGGAG-GAAGTCACACTC AGACCCCTCCCCAGAAGGACACT-CAAAAGCATGCTGCTCTAAGGTGGCATCTCTTA CAGAAGCAAGAACAGCAGCAAACACAGCAACCC-CAAACTGAGTCTTGCCATAGTCA GATGCACAGGC-CAATTAAGGTGGAACCTGGATGCAAGCCA-CATGCCTGTATGCACA CAGCACCACCAGAAAACAAAACATG-GAAAAAGGTAACTAAGCAAGAGAATCCACCT GCAAGCTGTGATAATGTGCAGCAAAAGAGCATCAT-TGAGACCATGGAGCAGCATCT GAAGCAGTTT-CACGCCAAGTCGTTATTTGACCATAAGGCTCT-TACTCTCAAATCACA GAAGCAAGTAAAAGTTGAAATGTCAGGGCCAGT-CACAGTTTTGACTAGACAAACCA CTGCTGCAGAACTTGATAGCCACACCCCAGCTT-TAGAGCAGCAAACAACTTCTTCA GAAAAGACAC-CAACCAAAAGAACAGCTGCTTCTGTTCTCAATAAT-TTTATAGAGTCA CCTTCCAAATTACTAGATACTCCTATAAAAAATTT-ATTGGATACACCTGTCAAGACTC AATATGATTTCC-CATCTTGCA-GATGTGTAGGTAAGTGCCAGAAATGTACTGAGA-CAC ATGGCGTTTATCCAGAATTAGCAAATT-TATCTTCAGATATGGGATTTTCCTTCTTTTT TTAAATCTTGAGTCTGGCA (SEQ ID NO:54; >chr4: 106155039-106158612), or a fragment thereof at least 8, 10, 12, 14, 16, 18, or 20 nucleotides in length.

Therefore, in some embodiments, the capture probe has the nucleic acid sequence: CTATTATCT-CAACAGAGCAAATTATTGAAAAAGAT-GAAGGTCCTTTTTATACCCATCT AGGAGCAGGTCCTAATGTGGCAGCTATT-AGAGAAATCATGGAAGAAAGGTAATTAA CGCAAAGGCAC (SEQ ID NO:55; >chr4:106162481-106162605), or a fragment thereof at least 8, 10, 12, 14, 16, 18, or 20 nucleotides in length.

Therefore, in some embodiments, the capture probe has the nucleic acid sequence: GTGGGTTTCTT-TAAGGTTTGGACAGAAGGGTAAAGCTATTAGGATT-GAAAGAGTCAT CTATACTGGTAAAGAAGGCAAAAGTTCTCAGG-GATGTCCTATTGCTAAGTGGGTAA GTGTGACTTGA (SEQ ID NO:56; >chr4:106163976-106164099), or a fragment thereof at least 8, 10, 12, 14, 16, 18, or 20 nucleotides in length.

Therefore, in some embodiments, the capture probe has the nucleic acid sequence: TGGTGATC-CACGCAGGTGGTTCGCAGAAGCAGCAGT-GAAGAGAAGCTACTGTGTT TGGTGCGG-GAGCGAGCTGGCCACACCTGTGAGGCTGCAGTGAT-TGTGATTCTCAT CCTGGTGTGG-GAAGGAATCCCGCTGTCTCTGGCTGACAAACTC-TACTCGGAGCTTA CCGAGACGCTGAG-GAAATACGGCACGCTCACCAATCGCCGGTGTGC-CTTGAATGA AGAGTAAGTGAAGCCCAG (SEQ ID NO:57; >chr4:106164712-106164950), or a fragment thereof at least 8, 10, 12, 14, 16, 18, or 20 nucleotides in length.

Therefore, in some embodiments, the capture probe has the nucleic acid sequence: CTTTTGATTTTTCAG-GAGAACTTGCGCCTGTCAGGGGCTG-GATCCAGAAACCTGTG GTGCCTCCTTCTCTTTTGGTTGTTCATGGAG-CATGTACTACAATGGATGTAAGTTTG CCAGAAGCAAGATCCCAAGGAAGTT-TAAGCTGCTTGGGGATGACCCAAAAGAGGTT TGTTTACTTCCT (SEQ ID NO:58; >chr4:106180761-106180941), or a fragment thereof at least 8, 10, 12, 14, 16, 18, or 20 nucleotides in length.

Therefore, in some embodiments, the capture probe has the nucleic acid sequence: ATTCACTTTATACAG-GAAGAGAAACTGGAGTCTCAT-TTGCAAAACCTGTCCACTCTT ATGGCACCAA-CATATAAGAAACTTGCACCTGATGCATATAATAAT-CAGGTAAGTTTA AATAAT (SEQ ID NO:59; >chr4: 106182901-106183020), or a fragment thereof at least 8, 10, 12, 14, 16, 18, or 20 nucleotides in length.

Therefore, in some embodiments, the capture probe has the nucleic acid sequence: ACTTTTATTTTTCAGATT-GAATAT-GAACACAGAGCACCAGAGTGCCGTCTGGGTCTG AAGGAAGGCCGTCCATTCTCAGGGGTCACTG-CATGTTTGGACTTCTGTGCTCATGC CCACAGA-GACTTGCACAACATGCAGAATGGCAGCACAT-TGGTAAGTTGGGCTGAG (SEQ ID NO:60; >chr4: 106190752-106190919), or a fragment thereof at least 8, 10, 12, 14, 16, 18, or 20 nucleotides in length.

Therefore, in some embodiments, the capture probe has the nucleic acid sequence: TTACTTCCC-TACCAGGTATGCACTCTCACTAGAGAA-GACAATCGAGAATTTGGAGG AAAACCTGAGGAT-GAGCAGCTTCACGTTCTGCCTTTATACAAAGTCT-CTGACGTGG ATGAGTTTGGGAGTGTG-GAAGCTCAGGAGGAGAAAAAACGGAGTGGTGC-CATTCA GGTACT-GAGTTCTTTTCGGCGAAAAGTCAGGATGTTAG-CAGAGCCAGTCAAGACTT GCCGACAAAGGAAACTAGAAGC-CAAGAAAGCTGCAGCTGAAAAGCTTTCCTCCCTG GAGAACAGCTCAAATAAAAAT-GAAAAGGAAAAGTCAGCCCCATCACGTA-CAAAACA AACT- GAAAACGCAAGCCAGGCTAAACAGTTGGCAGGTAAATTTAATGTAA (SEQ ID NO:61; >chr4: 106193706-106194090), or a fragment thereof at least 8, 10, 12, 14, 16, 18, or 20 nucleotides in length.

Therefore, in some embodiments, the capture probe has the nucleic acid sequence: TTACCCTGTCCACAGAACTTTTGCGACTTTCAGGACCAGTCATGCAGCAGTCCCAG CAGCCCCAGCCTCTACAGAAGCAGCCACCACAGCCCCAGCAGCAGCAGAGACCCC AGCAGCAGCAGCCACATCACCCTCAGACAGAGTCTGTCAACTCTTATTCTGCTTCT GGATCCACCAATCCATACATGAGACGGCCCAATCCAGTTAGTCCTTATCCAAACTCT TCACACACTTCAGATATCTATGGAAGCACCAGCCCTATGAACTTCTATTCCACCTCA TCTCAAGCTGCAGGTTCATATTTGAATTCTTCTAATCCCATGAACCCTTACCCTGGG CTTTTGAATCAGAATACCCAATATCCATCATATCAATGCAATGGAAACCTATCAGTG GACAACTGCTCCCCATATCTGGGTTCCTATTCTCCCCAGTCTCAGCCGATGGATCT GTATAGGTATCCAAGCCAAGACCCTCTGTCTAAGCTCAGTCTACCACCCATCCATA CACTTTACCAGCCAAGGTTTGGAAATAGCCAGAGTTTTACATCTAAATACTTAGGTT ATGGAAACCAAAATATGCAGGGAGATGGTTTCAGCAGTTGTACCATTAGACCAAAT GTACATCATGTAGGGAAATTGCCTCCTTATCCCACTCATGAGATGGATGGCCACTT CATGGGAGCCACCTCTAGATTACCACCCAATCTGAGCAATCCAAACATGGACTATA AAAATGGTGAACATCATTCACCTTCTCACATAATCCATAACTACAGTGCAGCTCCGG GCATGTTCAACAGCTCTCTTCATGCCCTGCATCTCCAAAACAAGGAGAATGACATG CTTTCCCACACAGCTAATGGGTTATCAAAGATGCTTCCAGCTCTTAACCATGATAGA ACTGCTTGTGTCCAAGGAGGCTTACACAAATTAAGTGATGCTAATGGTCAGGAAAA GCAGCCATTGGCACTAGTCCAGGGTGTGGCTTCTGGTGCAGAGGACAACGATGAG GTCTGGTCAGACAGCGAGCAGAGCTTTCTGGATCCTGACATTGGGGGAGTGGCCG TGGCTCCAACTCATGGGTCAATTCTCATTGAGTGTGCAAAGCGTGAGCTGCATGCC ACAACCCCTTTAAAGAATCCCAATAGGAATCACCCCACCAGGATCTCCCTCGTCTTT TACCAGCATAAGAGCATGAATGAGCCAAAACATGGCTTGGCTCTTTGGGAAGCCAA AATGGCTGAAAAAGCCCGTGAGAAAGAGGAAGAGTGTGAAAAGTATGGCCCAGAC TATGTGCCTCAGAAATCCCATGGCAAAAAAGTGAAACGGGAGCCTGCTGAGCCACA TGAAACTTCAGAGCCCACTTACCTGCGTTTCATCAAGTCTCTTGCCGAAAGGACCAT GTCCGTGACCACAGACTCCACAGTAACTACATCTCCATATGCCTTCACTCGGGTCA CAGGGCCTTACAACAGATATATATGATATCACCCCCTTTTG (SEQ ID NO:62; >chr4:106196190-106197691), or a fragment thereof at least 8, 10, 12, 14, 16, 18, or 20 nucleotides in length.

Therefore, in some embodiments, the capture probe has the nucleic acid sequence: TGGCCTCTGTGGTTTCTATCCCTGCCTTTCTGGGGGCAGAAATGTCTGCTGCAGTC CTTCCTTTTGGAAATCTGAAGACTTTTGGAATTGCCCCTGAAAAGAAAGGAA (SEQ ID NO:63; >chr6:43299498-43299605), or a fragment thereof at least 8, 10, 12, 14, 16, 18, or 20 nucleotides in length.

Therefore, in some embodiments, the capture probe has the nucleic acid sequence: TCTAGGTATTTATTCTTAGTTGTGAACACTGGATTCTGTGTGGTCCTGGATGGCACC AACTGTAGTTTCCTGTTCAGGCATTCCCTGAGGGACCATATTGTCTTCAATTACCTG CTCCCTTGGAGGGGACCTTGACACTGGAGCTTTAACCAAATTCAGAGGGTCGCCAC TGTCATCATCTACTTGCAGAATTGCCACCTCTGTGGTGGATGCATTCGATATTTCTA GCTGTAATGGCCCCAACTCCAGGGAACTACATTTAGAAGGGTCACCTGGCTCAGAG AGTGGAGAACACAGTTTATCTTTTTGAACTCCAGAGGTCCGTGTGACAAAGTCAACA AGGTCTGGAAGGCAAGGAGATGGCCCAAGGCCTGCAGAATTAATTGTTTTTAATTC CAATCCGAGTGACTCTTGTTTGTCTAATTGGGAAGATTCTTTTACTTCCTCAGGCAT CATTCCTCCTGCTAACAGGTCAAGGGCCTGGTGTGTTCCCTCTAGGCCCCCCAAGC CACGGTCAACATTTTCTGTAAGTCCAGTTTTCAAAATGTTAGGAGAAGGGATCCTAA CACTCCTGGGATTAGGTGAGTTTCGTTCACCCTCTGTCTCAAAGTCAAGCACCAAG GTTTTGGGAGAATCTAACGGAAACCCAGAAAAAGATGGGATTGGTTCGAAGTCAGC GGGATCGGAGGAATTACACCCTATAGGTGATACAGAATTTTCTTCACACACTTTCTG ACACAAGACAGTTGGGGATCTATGTGCTGGGCTTACCCGAGTAGTGCAGAAATCAA CAGGCATATCCCCCAGATTCCCCAGGGCAGTAAGCTCCTCTACCTTTAAGTCTGTA GCTTCAAAGTCTTCTAGGGCCTTGCTTTCTATTGTCACTGTTAACTCTGGATGGACA TCTTGTAGCTCCAGTGCTTCTGTTTTTGGTTTCTCTGGGCTCTCCCAGGTCTCTGGC CTCTTCTTGTTTTCATCCCAAACAGCCAACTCATAGATCTTTTTAACTTGAAAGTCTT TTGATCTTTCTCTCTTGAGTTTGAGACTTCTGTACCTAGAAGTTCTAGAAGCTGATTC TGGAGCTGAATTCTCTAGCCCCTCCTCACTAACAACTGAAACTCCTTGCTCTTGTGG ACTACCTGTTAAACACATAGCTGATCTGGCTGGGGAATGAAGCAGCAACTCTGGGG CAGAAATTTTCACAGGTGTATCTTGTGGGTTGAGTAAAGACCTAGCTTCTGATAAAA ATGAGTCTAATTTTGCCTTTGTGAAAGAGCAAGCCTGTGGACTCAATTTGATCACTA CTTTACTTGGAGTTTCACTTCCTGTCATCAATTTATTGGACTGTTCAGCCTCTTTGTC AATCATTAGCAAGTTGGGCTGTTTTACTTCTCCCTCCCACATGTATCTGTTTCCATG GTTCAAATTAGAATCATCTATGCTGTGGGGTCCAATGCTGGTACTTACTCCCTCATC AACTATCCCCTCAGACAGCTCCTTTACCCTTTCTTTTAGTTCAGTGTTTGTCTCTATC TCACTTTCTCTACAATCCTCAGATTTACGGAGCTCTTGGCTTTCCTTATCCTGGTTAA CAGATTCTCTGAGGTGGATTTCTACCAACTTCTGAGATTCTTTGCACTGTATATCTAA CAGTTGAGGAGGTGGTTCTACACCAGGTGGTCCTGGCTCTCCCAGGTCAAGCTCA CTCTTCTCTGGAGATATATCCCTACTAGTGTCACTCTGGAAGGAACTAGAGGTCCAT ATGGCCAAAGTGTCTGTCTTTGGGGTAATTGTTTCATAAGGCCTGCTTTGGCACAAC CTTGTCAGAGGCTGTAGGAAGCCAT-AGGTGCTGCCTGTGCTTTTTGGGCCTACATG TTC-TACAACTGACCATTTCCCTAGGGC-CACCAGAGTTTTTGCAATGGGCTTTTCAGA GTTGCTAACTATAGGAGCAGCGACCAAACCCT-CATCTTGATGCAACTCCTCTTGGG ATGCACTGCTGTT-CAAAGGAGAAGTAGAAGAGGTGTCT-GAACTTTTGGTTCTAGAG AGGTTGCTATTTTCCC-CATTGGCCAATGGACCACCACTTAGCTTAGTCTC-AGGGGC CCCCTTAGTCTCAGGGGCCCCCTTTC-CACCACTACTATAGAATATGTCATACAGGT CCTTAG-CATTGGCTGTGGCTAAGCATGAAT-TTCGCTTCTCTAATTTTTTGGCTTGTT CACTGAACACACTTGAGAGGGGTGGTG-GAGGACGTACTAACACAGAGAACAGGGT CTGGTCTCGGTCACTCTCACTCACCCCAG-GAGCTGTCTCATCAGAAGGAATGGCAG CTGGCTGTGCTGAGGCCATGATGGCTA-CAGGCAACACTGGGTTCAAAATGTTAGGA CCCACGAAGCCAGGGCTGAGAGTCTGAGATA-CAACTGGGTTTGATTTTACTGGAGC CAAGATAG-CATTTGCTTGAGCAGCAGACGGGGCAGCTGGAT-GAGGTATAACGGGG GGTGGTGGAGGTGGTGGAGGTGGGGGTGGTG-GAGGAGGTGGTAGTATTTGTTCA GGTAAAT-GAGATGGCTCACTCTTTTCAGCCAACAC-CACTTTTTCCTCTGGAGACCCCT TTTAGAATCACCTCTTCCCCTCCAAATGCTTTG-GAGATGATGTCTGGAGGTAAGAG GAGATCAGCT-GAAGACTCTTTAACCACTGGCAGAGGTT-TAGCAGTGGTTCCAGAGG ACTTAATAGACAGAAAGGTGTTAAGAG-GAGCTGGCTTGCTCATTGTGGCTGAACAT GACTTGCGGAGTACTGTGGATG-GAATAGGCAGGTTGGGTCGGATCTTAGTCTGTGT GGAAGTTGTCACAACAGGCATC-CAAGGGCTGGTATGTGCAACAACAGTTTTCCCAG AGAGCTTGATTTTGA-TAGGCTTTGCCTTCCCAGCTTCAGTTTTGC-CATCCTCTTTGT CCTTAC-TACTTTCTAGAATCTCTTCTTTAGAGATACTTGGGGT-CACCAATGAACTTTT CTCCTCTTCTTTTTCTGGCTTCTTCCAGCTGAAT-TTCCCAAAAGAAGATGATGTTGG TGATTCCTTCTT-TACCTCTTCTTTTAACTGGAGTTT-GATGCCAGTGTTCCTTTTATTTT CAGCTTTTTCAGGGGAGTTCC-TACCCTCAGAGAGTTGGTCTTCTAATTTCTCAGAGA CCTTGTCATCCTCCTTTACTTCTTT-CACAGCCTTTGCCTTTTTTTCTTTCTTCTCCTCC TTTGGTTTCTCACTAAGTTTGCGCTTTAGCT-CACTCTGCCGTCGCCGTTCTGTCTCT AGGAC-CACAGCCAAGCCAGCTTGGCGGTCCAGAT-TCCGCCGCTCCTCATATAATG GGTTTTCATCCACATATTTCTGGGAAGAAAAAAG (SEQ ID NO:64; >chr6:43304881-43308255), or a fragment thereof at least 8, 10, 12, 14, 16, 18, or 20 nucleotides in length.

Therefore, in some embodiments, the capture probe has the nucleic acid sequence: ACTACAAAGAC-CAACCTTGTATTTCTCATTGTGTTGGTGACCCTTCA-CATGTTGCTC CCCAGAAATTGGATCCCCCAAAAAT-TCCTCACAGAGCTGGCAATAAAATCCACTGAT GGGAACCAGAAACTCAGAGCCTG-GAAGAAGTAGAA (SEQ ID NO:65; >chr6:43308513-43308661), or a fragment thereof at least 8, 10, 12, 14, 16, 18, or 20 nucleotides in length.

Therefore, in some embodiments, the capture probe has the nucleic acid sequence: AAAAAGGAAACAT-ACCTTTTGCAGGAACAGT-TATCTTGTCAGTGCGCTTTATGGCAT CTTGCTTGGCCTCACTCTGGGTCTTTGAAGCC-CAAGGTCTGTTGTAGGGATCCAGT GTCTAT-TTGTAAGAGGC (SEQ ID NO:66; >chr6:43309835-43309964), or a fragment thereof at least 8, 10, 12, 14, 16, 18, or 20 nucleotides in length.

Therefore, in some embodiments, the capture probe has the nucleic acid sequence: GAGTAGGATAC-CAACCTGTGTGTGCTTCTTATTGTGCATATGAGT-GAAGAAATCAAA CATGGTCCCACA-GATGGTGTTGCAGTCTTTGCACCAGTGATTGCCA-GCATCATAAT ACTCATAAGCAGCAGTGGGCTGATC-CAACTGCTTAGTGGCTGACTGGGGGCTTTC GGCAGGCTTGGGGCTCTTAGTACGAAACTTCTCAT-TGTTTACTTTTGATTCCTAGAG GGGAAAAAT (SEQ ID NO:67; >chr6:43310399-43310632), or a fragment thereof at least 8, 10, 12, 14, 16, 18, or 20 nucleotides in length.

Therefore, in some embodiments, the capture probe has the nucleic acid sequence: AAATTGAGTTGT-TACCTTGTTGGAGGAGGAGTTTGAGAAC-GATGACACTTTTTCTGG GCTCTTAGAT-TTTCTGCTTTCCCAGGCTTCTCTGTAGGCTCTC-TACTGTCACTTAAA GACTTCTGGGATTTATCGAA-GATGTTAATTCCCAAGATCTGAGC-CACTTTGTCCAGT TCAGAT-TGCTTCTTTTCTGCCTCTTCTGCCTCTTGCCGTA-GCTCTGCAATGTCCTTC ATAATGTTATCCT-GAAGCCGACTCACCTCCACCAAGAGAG-GATCTTTGTGGCCATC CTTCTCCCTTCGTTTCTTGCGCAGCATTTCTCCT-GAGCAATCAAATG (SEQ ID NO:68; >chr6:43316047-43316378), or a fragment thereof at least 8, 10, 12, 14, 16, 18, or 20 nucleotides in length.

Therefore, in some embodiments, the capture probe has the nucleic acid sequence: CAAAGCAGCTGA-TACCTTGTTGTTTAT-GAAGCCGCTCTAACTCGGTCCTAAGATAGT ACATCTTCTTCTGGCGGGCTTCCCGGTCATTCTT-TAGTTTTTCCCTCTCTTCAATAAC CTGCAAAATA-CAAAG (SEQ ID NO:69; >chr6:43320100-43320229), or a fragment thereof at least 8, 10, 12, 14, 16, 18, or 20 nucleotides in length.

Therefore, in some embodiments, the capture probe has the nucleic acid sequence: AAAGCTAATATT-CACCTTTTGCTTCTGGGAAGCACGGTTCTTCT-CATCAGAGATCTT CTCTGGATTATATCTTATGAGT-GATGGAATGGACACCTGGACAGGCACTTGGGCCG CAGGAATTGAGCCTCGCAGAGACTCTTTCTGCT-TAGGCTTATCAGGAGTCACAGTG GGGAT-CACACGAAGATTGGGACGGC-TACGAGTAGCTTGTTTGGTTATTGGCATTAT CCTGTGTGGTTCAGGTACAGGGTGGTTTGACGGTT-GAGAGGTGGGATACATGGGC CATCTGGAGGCTG-CATATGCCATGTAGTGCCTATAGGCAT-CAAAAGAGGCAGGGG GAATGGCAGGTCCCTGGTAGTTCG-GAGGTATCCGAGCTGCAGCAAACTGAGAGGC CCTTGGCATGTGAAACTGAGA-TAAAGCAGCAGTGTGTGGAAGTCTAATTGGGGCAG ATGGGGCTGATGGCAA-CATGCACCTGACTGCAACAGATGACTGAAACC- CACTACCA ACCACCTCTGGTCCTGAAATATGACC-CACTGGATGGTCAGACTTTAGGAATGGAGG GCTGTTTTTTGTGAGCAGGTAAGGATCCACAG-GAGAAGGTGGGTGTGGATGGGAC ACCTCTG-GAGAGTGGGTATTGCTAT-GATGTGCCTCCCTGCTCTCTAGTCTGTGGGG ATCTGAGGAACGTCGATCAGCT-GAGAAGCAGTGGTCAACTGAGGAACAGCGGTCA GCTGAGAAGCGGTGGTCAACTGAG-GAACAGTGGTCAGCTGAAAAGTATCGGTCAA CTGAGGAACGGCGGTCAGCTGAGGAGCGTAAT-GATGGCTTCTTGCCATGAAGTCG TTCCTGGGTGCGTGCAGCCAAT-TGACTAATCTCTGCTACTCCAATATCCAGCCCTAT TGTCTTGAGCAAGTCATGGATCTTCGCATATTCTG-GATTGGTCTCTTCTAGTGATTC TAGCTTTACAGCTG-GAGCTGAAGACGGCAGGGAGCTTGCCTTCTGCCT-CATAACTT CACTCTCAGAGCTCCCAAGGGGCTTTGGTACGGAT-TCTGCCTTTAAATCCTCTTCTT CATCCCCAT-AGAGAAATTTCTCCTCATCTTCAATGTCGG-GAAAGCTACGTCGCCTTT TTTCCTGTGTACTGGTAGAATCAGCCAA-CATGCTCAGAATGCGGGAAAAACCACTG CCATCCTGGCTAGCTCTCTCATGGGGCAGCAG-GAAGTCTGTGTGTCGCTCAGGTC CCTCAGCCTT-CAAATCCAAATTATCCTTGTGGCATAGAAAACTTC-CAAATTTTTCTCT GAGAGGACTGTTGTCTTTGGGAATCCCAG-GAAGGGGACCCCATTGGTAGAGGTTG CCCT-GAGGTTCCTTCAAGGCAGTCTCTACCAT-AGTCCCCTTGTTTTCAATCTCTGAG GCAAAAGCAGCAATAGCACCACTTAGTGGAAGG-GATGGGTGCCCAGAGTAGAGAG GGT-GATCCTGGCTGGAGCTGGTACTGCTG-GAAAAACTCTCAAGCTGCAAAGACAAA CA (SEQ ID NO:70; >chr6:43322387-43323898), or a fragment thereof at least 8, 10, 12, 14, 16, 18, or 20 nucleotides in length.

Therefore, in some embodiments, the capture probe has the nucleic acid sequence: AAATGCAGCAGAGACCTG-CATGGAGGGCTCCATTATGTCCACCT-CAATCCGCTTCT TCAAAATGGATTTCTTGGGCAT-CACAGATACTTCCTCAGGCCGATGCAAAGAATATC CTGGCTCCGATGCTGT-TAGGACACCTGACAATCCAGGGATG-GAACAGCCAGTACC ACCACCATCAACTC-CAACCAGCTCCTGACTCAAGCTCCTACTTCGCTC-CTCCTCTTC CTCTCGCTTTCGTCTGGCAA-GATCCAGTTCTCGAAACTCAGGGTCGAGAAACC-TAG GACTTGGGCTTCTTCTACGCTGTCGA-TAGTTGCGAGTTCCTGATGTAAAACTTGGG TGATCCCCTCCCATGCTGTTTATCTTCACTGTGT-CATCATAACGGGGTCTTTTGGCC TCCCGGCTCCTTTCTTCAGATCGTATG-GAGTAGCCTTTGAGTTTTTCTCGATTCCGT TCTGTTCCCCGCAACAGCTCATCATGACAACTGA-TATGGGGACTATAATCAGATCG ATGCAG-GAAAGTTTCTTTTGTTCGGTAGTCCTCAT-CAAGTTGTCCCAAGAAGGGACT GAGAGGCCCTTCCTCCTGGGAAATATATCGCTCAA-GACCCCGAGAGCACTGGGAG CTTCGAGTGAA-GACAGAATCATCAGTCAGGTCATCCCTGAG-GAAAAAGAGA (SEQ ID NO:71; >chr6:43324849-43325518), or a fragment thereof at least 8, 10, 12, 14, 16, 18, or 20 nucleotides in length.

Therefore, in some embodiments, the capture probe has the nucleic acid sequence: TTAGGTGATGCCTACCTGTC-CATGTCTTCCAGATTATCCACTGGTGACCCCAGCCG ATCACTAAGCCGTCGCCGTTCTGGTGTGCTAA-CACAGAAGTGGTCATTGCCAACAG TGATCCT-TAAGCTCTTTTCCAAAGAGTCAGAACACA-GACCAGGAGAGCGTCTCTAC AAAAGTAAAGG (SEQ ID NO:72; >chr6:43333015-43333193), or a fragment thereof at least 8, 10, 12, 14, 16, 18, or 20 nucleotides in length.

Therefore, in some embodiments, the capture probe has the nucleic acid sequence: GAGGGGTGGGAT-TACCCGGCTGCCGCTGTCGCCTG-GATGGTCTCCGCGGCCGTC CCGGGCAT-AGTCGGCGCGGGACTCCCCCCGGCTGCTGCCTC-TGAAGCCGGCCGG GCCCGGCGG-GAAGAGTCGTCGGCCCCGCGGTGGCGACGGG-GAGCCGCGACGGG CCCGAGGCGGGGACGGGGA-GACGCGACGACCCCGTGGCGGGGACGGCGAGGCC CGGCGGCCGCGGTGCCCT-GAGGGCGAGCGGGGTCGGCGAGCCGGGGTCC-GCGA CGAGGAGCCGGAGGGCGGAGGCGGCGGT-GAGCTGCGGCGAGCCGGGCCTGAGG AGGAGCCAGAGCTGCGGCCGCTGCGCGGGCC-GCCCCCGCCGTCGTCTTTAGGCC GGTGGGAAGA-GACGGAGGAGCGAGCGCTGCTGCGGTA-CATGGTTCTTGCAGCGG C (SEQ ID NO:73; >chr6:43336690-43337118), or a fragment thereof at least 8, 10, 12, 14, 16, 18, or 20 nucleotides in length.

Therefore, in some embodiments, the capture probe has the nucleic acid sequence: CTTTGTACTTTTTTTTTTCCT-TAGTCTTTCTTTGAAGCAGCAAGTATGAT-GAGCAAGC TTTCTCACAAGCATTTGGTTTTAAAT-TATGGAGTATGTGTCTGTGGAGACGAGAGTA AGTAAAACTACAGGCTTTCTAA (SEQ ID NO:74; >chr9:5073674-5073810), or a fragment thereof at least 8, 10, 12, 14, 16, 18, or 20 nucleotides in length. Therefore, in some embodiments, the capture probe has the nucleic acid sequence: CTTTCTCTTAAAGGCATG-GAGAGTAGAAAACTGATTTCTGCTACAGACAT-TCAGTAC TCTGGCAGTCTGCTGAACTCCTTGAAT-GAGCAACGTGGCCATGGACTCTTCTGTGA TGTTACCGTTATTGTGGAAGACCGAAAAT-TCCGGGCTCACAAGAATATTCTTTCAGC TTCTAGTACCTACTTC-CATCAGCTCTTCTCTGTTGCTGGGCAAGTTGTT-GAACTGAG CTT-TATAAGAGCAGAGATCTTTGCAGAAATTCTCAA-TTATATCTATAGTTCTAAAATT GTTCGTGTTA-GATCAGATTTGCTTGATGAGTTAAT-TAAATCAGGGCAGTTATTAGGA GTGAAATT-TATAGCAGAGCTTGGTGTCCCATTGTCACAGGT-TAAAAGCATCTCAGGT ACAGCGCAG-GATGGTAATACTGAGCCTTTACCTCCTGAT-TCTGGTGACAAGAACCT TGTAATACAGAAAT-CAAAAGATGAAGCCCAAGATAATGGGGCTACTA-TAATGCCTAT TATAACAGAGTCTTTTTCAT-TATCTGCCGAAGATTATGAAATGAAAAAGATCAT-TGTT ACCGATTCTGATGATGATGATGATGATGTCAT-TTTTTGCTCCGAGATTCTGCCCACA AAGGA-GACTTTGCCGAGTAATAACACAGTGGCACAGGTC-CAATCTAACCCAGGCCC TGTTGCTATTTCA-GATGTTGCACCTAGTGCTAGCAATAACTCGCC-CCCTTTAACAAA TATCACACC-TACTCAGAAACTTCCTACTCCTGT-GAATCAGGCAACTTTGAGCCAAAC ACAAGGAAGT-GAAAAATTGTTGGTATCTTCAGCTCCAACACATC-TGACTCCCAATAT TATTTTGTTAAATCAGACAC- CACTTTCTACACCACCAAATGTCAGTTCTTCACTTCCA AATCATATGCCCTCTTCAATCAATTTACTTGTGCAGAATCAGCAGACACCAAACAGT GCTATTTTAACAGGAAACAAGGCCAATGAAGAGGAGGAGGAGGAAATAATAGATGA TGATGATGACACTATTAGCTCCAGTCCTGACTCGGCCGTCAGTAATACATCTTTGGT CCCACAGGCTGATACCTCCCAAAATACCAGTTTTGATGGATCATTAATACAGAAGAT GCAGATTCCTACACTTCTTCAAGAACCACTTTCCAATTCCTTAAAAATTTCAGATATA ATTACTAGAAATACTAATGATCCAGGCGTAGGATCAAAACATCTAATGGAGGGTCAG AAGATCATTACTTTAGATACAGCTACTGAAATTGAAGGCTTATCGACTGGTTGCAAG GTTTATGCAAATATCGGTGAAGATACTTATGATATAGTGATCCCTGTCAAAGATGAC CCTGATGAAGGGGAGGCCAGACTTGAGAATGAAATACCAAAAACGTCTGGCAGCG AGATGGCAAACAAACGTATGAAAGTAAAACATGATGATCACTATGAGTTAATAGTAG ATGGAAGGGTCTATTATATCTGTATTGTATGCAAAAGGTCATATGTCTGTCTGACAA GCTTGCGGAGACATTTTAACATTCATTCTTGGGAGAAGAAGTATCCGTGCCGTTACT GTGAGAAGGTATTTCCTCTTGCAGAATATCGCACAAAGCATGAAATTCATCACACAG GGGAGCGAAGGTATCAGTGTTTGGCCTGTGGCAAATCTTTCATCAACTATCAGTTTA TGTCTTCACATATAAAGTCAGTTCATAGTCAAGATCCTTCTGGGGACTCAAAGCTTT ATCGTTTACATCCATGCAGGTCTTTACAAATCAGACAATATGCATATCTTTCCGATAG ATCAAGCACTATTCCTGCAATGAAGGATGATGGTATTGGGTATAAGGTTGACACTG GAAAAGAACCTCCAGTAGGGACCACTACATCTACTCAGAACAAGCCAATGACCTGG GAAGATATTTTTATTCAGCAGGAAAATGATTCAATTTTTAAACAAAATGTAACAGATG GCAGTACTGAGTTTGAATTTATAATACCAGAGTCTTACTAAACTCCTTTGAAATAC (SEQ ID NO:75; >chrX: 119387256-119389304), or a fragment thereof at least 8, 10, 12, 14, 16, 18, or 20 nucleotides in length.

Therefore, in some embodiments, the capture probe has the nucleic acid sequence: TCGGGCCAAGATGGCGGTGCAGGTGGTGCAGGCGGTGCAGGCGGTTCATCTCGA GTCTGACGCTTTCCTCGTTTGTCTCAACCACGCTCTGAGCACAGAGAAGGAGGAAG TAATGGGGCTGTGCATAGGGGAGGTGAGTAGGT (SEQ ID NO:76; >chrX:154299793-154299935), or a fragment thereof at least 8, 10, 12, 14, 16, 18, or 20 nucleotides in length.

Therefore, in some embodiments, the capture probe has the nucleic acid sequence: CCCACTCTAGTTGAACGATGATACAAGGTAAGACTGT (SEQ ID NO:77; >chrX: 154300592-154300628), or a fragment thereof at least 8, 10, 12, 14, 16, 18, or 20 nucleotides in length.

Therefore, in some embodiments, the capture probe has the nucleic acid sequence: TTCCCAGTAGGAGTGACTCCAAATTTGCATATACTGGAACTGAAATGCGCACAGTT GCTGAAAAGGTATGTGTGC (SEQ ID NO:78; >chrX:154301642-154301716), or a fragment thereof at least 8, 10, 12, 14, 16, 18, or 20 nucleotides in length.

Therefore, in some embodiments, the capture probe has the nucleic acid sequence: TTTCCTTTAGGTTGATGCCGTCAGAATTGTTCACATTCATTCTGTCATCATCTTACGA CGTTCTGATAAGAGGAAGGACCGAGTAGAAATTTCTCCAGAGCAGCTGTCTGCAGC TTCAACAGAGGCAGAGATATCCTTAC (SEQ ID NO:79; >chrX:154305435-154305574), or a fragment thereof at least 8, 10, 12, 14, 16, 18, or 20 nucleotides in length.

Therefore, in some embodiments, the capture probe has the nucleic acid sequence: ACAGACACACAGGTTGGCTGAACTGACAGGCCGCCCCATGAGAGTTGTGGGCTGG TATCATTCCCATCCTCATATAACTGTTTGGCCTTCACATGTTGGTAAGTATCA (SEQ ID NO:80; >chrX:154306881-154306988), or a fragment thereof at least 8, 10, 12, 14, 16, 18, or 20 nucleotides in length.

Therefore, in some embodiments, the capture probe has the nucleic acid sequence: TTATTTTCAGATGTTCGCACACAAGCCATGTACCAGATGATGGATCAAGGCTTTGTA GGACTTATTTTTTCCTGTTTCATAGAAGATAAGAACACAAAGGTATTGTGTG (SEQ ID NO:81; >chrX:154317528-154317636), or a fragment thereof at least 8, 10, 12, 14, 16, 18, or 20 nucleotides in length.

Therefore, in some embodiments, the capture probe has the nucleic acid sequence: CCTTTGATAGACTGGCCGGGTACTCTACACTTGCTTCCAATCCATACAGGCCCAAA AGAGTTCAGAGTAAGTATGA (SEQ ID NO:82; >chrX:154319049-154319124), or a fragment thereof at least 8, 10, 12, 14, 16, 18, or 20 nucleotides in length.

Therefore, in some embodiments, the capture probe has the nucleic acid sequence: CCATCCTAAGGTCCCTTCATGGTCCACGAGACTTCTGGAGCTCCAGCCAGCACATC TCCATTGAGGGCCAGAAGGAAGAGGAAAGGTAGGAGGGC (SEQ ID NO:83; >chrX:154327580-154327674), or a fragment thereof at least 8, 10, 12, 14, 16, 18, or 20 nucleotides in length.

Therefore, in some embodiments, the capture probe has the nucleic acid sequence: TGCCTCACAGGTATGAGAGAATCGAAATCCCAATCCATATTGTACCTCATGTCACTA TCGGGAAAGTGTGCCTTGAATCAGCAGTAGAGCTGCCCAAGATCCTGTGCCAGGA GGAGCAGGATGCGTATAGGAGGATCCACAGGTAGAGACCC (SEQ ID NO:84; >chrX: 154344322-154344473), or a fragment thereof at least 8, 10, 12, 14, 16, 18, or 20 nucleotides in length.

Therefore, in some embodiments, the capture probe has the nucleic acid sequence: TATTCTTTAGCCTTACACATCTGGACTCAGTAACCAAGATCCATAATGGCTCAGGTA AGAATTG (SEQ ID NO:85; >chrX: 154344976-154345039), or a fragment thereof at least 8, 10, 12, 14, 16, 18, or 20 nucleotides in length.

Therefore, in some embodiments, the capture probe has the nucleic acid sequence: TTTTTTTAATCAAAGGAACAATATGAATTATACTGTGAGATGGGCTCCACATTCCAAC TATGTAAAATATGTGCTGAAAATGATAAGGATGTAAAGATTGAGCCCTGTGGACACC TCATGTGCACATCCTGTCTTACATCCTGGCAGGTACGGATCTAAACA (SEQ ID NO:86; >chr11:119148861-119149022), or a fragment thereof at least 8, 10, 12, 14, 16, 18, or 20 nucleotides in length.

Therefore, in some embodiments, the capture probe has the nucleic acid sequence: TTGCTTCTTCTGCAG- GAATCAGAAGGTCAGGGCTGTCCTTTCTGCC-GATGTGAAAT TAAAGGTACTGAACCCATCGTGGTA-GATCCGTTTGATCCTAGAGGGAGTGGCAGCC TGTTGAGGCAAGGAGCAGAGGGAGCTCCCTCCC-CAAATTATGATGATGATGATGAT GAACGAGCTGAT-GATACTCTCTTCATGATGAAGGAATTGGCTGGTGC-CAAGGTAAG ATGGCAGTTT (SEQ ID NO:87; >chr11: 119149205-119149438), or a fragment thereof at least 8, 10, 12, 14, 16, 18, or 20 nucleotides in length.

Therefore, in some embodiments, the capture probe has the nucleic acid sequence: GTGGGATGTTTTTGCAGAT-GATGGGCTCCCGGAAGACAGTCCCCCCCAG-GATGTT CCGGATAGTTCCATTGGGACTTTTCCA-CATCTTCTTCAGCTTGAACTCTGTGAGGAC AGAGATAATAG (SEQ ID NO:88; >chr15:90631878-90632000), or a fragment thereof at least 8, 10, 12, 14, 16, 18, or 20 nucleotides in length.

Therefore, in some embodiments, the capture probe has the nucleic acid sequence: AAGAAGTG-GAGAATGTCAGTCTGAGTCAGGCCCTTCTGTCTT-GAACATGAGTTTTT ATGGCGGGAGGTA-GACTGACCCTTTTTGGACTTCAGGTGGCTGTAGG-AGACAGAA (SEQ ID NO:89; >chr17:7572912-7573023), or a fragment thereof at least 8, 10, 12, 14, 16, 18, or 20 nucleotides in length.

Therefore, in some embodiments, the capture probe has the nucleic acid sequence:

```
                                    (SEQ ID NO: 90; >chr17: 7573912-7574048)
GCTGAGGTCACTCACCTGGAGTGAGCCCTGCTCCCCCCTG

GCTCCTTCCCAGCCTGGGCATCCTTGAGTTCCAAGGCCTC

ATTCAGCTCTCGGAACATCTCGAAGCGCTCACGCCCACGG

ATCTGCAGCAACAGAGG,
```

or a fragment thereof at least 8, 10, 12, 14, 16, 18, or 20 nucleotides in length.

Therefore, in some embodiments, the capture probe has the nucleic acid sequence: TACAATATTTTCAACT-TACGACGAGTTTATCAGGAAGTAACAC-CATCGTAAGTCAAG TAGCATCTGTATCAGGCAAAG (SEQ ID NO:91; >chr17:7576522-7576599), or a fragment thereof at least 8, 10, 12, 14, 16, 18, or 20 nucleotides in length.

Therefore, in some embodiments, the capture probe has the nucleic acid sequence: ATTTTCATGCTCTCTT-TAACAATTTTCTTTTTGAAAGCTGGTCTGGTCCTT-TAAAATAT ATAT (SEQ ID NO:92; >chr17:7576610-7576672), or a fragment thereof at least 8, 10, 12, 14, 16, 18, or 20 nucleotides in length.

Therefore, in some embodiments, the capture probe has the nucleic acid sequence: CCCAAGACTTAGTACCT-GAAGGGTGAAATATTCTC-CATCCAGTGGTTTCTTCTTTGG CTGGGGAGAG-GAGCTGGTGTTGTTGGGCAGTGCTAGGAAAGA-GGCAA (SEQ ID NO:93; >chr17:7576838-7576941), or a fragment thereof at least 8, 10, 12, 14, 16, 18, or 20 nucleotides in length.

Therefore, in some embodiments, the capture probe has the nucleic acid sequence: GTCCTGCTTGCT-TACCTCGCT-TAGTGCTCCCTGGGGGCAGCTCGTGGTGAGGCTC CCCTTTCTTGCGGAGAT-TCTCTTCCTCTGTGCGCCGGTCTCTCCCAGGAC-AGGCAC AAACACGCACCT-CAAAGCTGTTCCGTCCCAGTAGATTACCAC-TACTCAGGATAGGA (SEQ ID NO:94; >chr17:7577004-7577170), or a fragment thereof at least 8, 10, 12, 14, 16, 18, or 20 nucleotides in length.

Therefore, in some embodiments, the capture probe has the nucleic acid sequence: CAAGTGGCTCCTGACCTG-GAGTCTTCCAGTGTGATGATGGTGAG-GATGGGCCTCC GGTTCATGCCGCCCATGCAG-GAACTGTTACACATGTAGTTGTAGTGGATGGTGGTA CAGTCAGAGCCAACCTAGGAGATAACACA (SEQ ID NO:95; >chr17:7577484-7577623), or a fragment thereof at least 8, 10, 12, 14, 16, 18, or 20 nucleotides in length.

Therefore, in some embodiments, the capture probe has the nucleic acid sequence: CACTGACAACCACCCT-TAACCCCTCCTCCCAGA-GACCCCAGTTGCAAACCAGACCT CAGGCGGCT-CATAGGGCACCACCACACTATGTCGAAAAGTGT-TTCTGTCATCCAAA TACTCCACACGCAAAT-TTCCTTCCACTCGGATAAGATGCTGAG-GAGGGGCCAGACC TAAGAGCAATCAGT (SEQ ID NO:96; >chr17:7578123-7578304), or a fragment thereof at least 8, 10, 12, 14, 16, 18, or 20 nucleotides in length.

Therefore, in some embodiments, the capture probe has the nucleic acid sequence: GCCCCAGCTGCTCAC-CATCGCTATCTGAGCAGCGCT-CATGGTGGGGGCAGCGCCT CACAACCTCCGT-CATGTGCTGTGACTGCTTGTAGATGGCCATGGCG-CGGACGCGG GTGCCGGGCGGGGGTGTGGAAT-CAACCCACAGCTGCACAGGGCAGGTCTTGGCC AGTTGGCAAAACATCTTGTTGAGGGCAGGG-GAGTACTGTAGGAAGAGGAAGG (SEQ ID NO:97; >chr17:7578356-7578571), or a fragment thereof at least 8, 10, 12, 14, 16, 18, or 20 nucleotides in length.

Therefore, in some embodiments, the capture probe has the nucleic acid sequence: CTCAGGGCAACTGACCGTGCAAGTCACA-GACTTGGCTGTCCCAGAATGCAAGAAG CCCA-GACG-GAAACCGTAGCTGCCCTGGTAGGTTTTCTGGG-AAGGGACAGAAGATG ACAGGGGCCAG-GAGGGGGCTGGTGCAGGGGCCGCCGGTGTAG-GAGCTGCTGGT GCAGGGGCCACGGGGG-GAGCAGCCTCTGGCATTCTGGGAGCTTCATCTG-GACCT GGGTCTTCAGTGAACCATTGTT-CAATATCGTCCGGGGACAGCATCAAATCATCCATT GCTTGGGACGGCAAGGGGGACTGTAGATGGGT-GAA (SEQ ID NO:98; >chr17:7579297-7579605), or a fragment thereof at least 8, 10, 12, 14, 16, 18, or 20 nucleotides in length.

Therefore, in some embodiments, the capture probe has the nucleic acid sequence: AACCCTTGTCCT-TACCAGAACGTTGTTTTCAGGAAGTCTGAAA-GACAAGAGC(SEQ ID NO:99; >chr17:7579685-7579736), or a fragment thereof at least 8, 10, 12, 14, 16, 18, or 20 nucleotides in length.

Therefore, in some embodiments, the capture probe has the nucleic acid sequence: AATGGATCCACT-CACAGTTTCCATAGGTCT-GAAAATGTTTCCTGACTCAGAGGGGG CTCGACGCTAGGATCTGACTGCGGCTCCTC-CATGGCAGTGACCCGGAAGGCAGTC TGGCTGCTGCAAGAGGAAAAG (SEQ ID NO:100; >chr17:7579824-7579955), or a fragment thereof at least 8, 10, 12, 14, 16, 18, or 20 nucleotides in length.

Therefore, in some embodiments, the capture probe has the nucleic acid sequence: TTCTTTTGAATACAGGGT-GAGCATGGACAATCTTGTGCCAAAATGCTTGT- GAATCGA GCATTGGGCCGCTG-GAGGCAGCGTATGCTCCGAGCAGATAACACTAG-TGCCATAG TAATCTG-CATCTCTCCAGAAGTGGACAATCAGGGAAACTT-TACCAATGAAGATGAGT TATACCT-GAACCTGACTGACAGCCCTTCCTATAATAGTC-AAGAAACCTGTGTGATGA CTCCTTCCCCATGTTC-TACACCACCAGTCAAGGTATATAGTTCCATA (SEQ ID NO:101; >chr17:58733945-58734217), or a fragment thereof at least 8, 10, 12, 14, 16, 18, or 20 nucleotides in length.

Therefore, in some embodiments, the capture probe has the nucleic acid sequence: CTTCTTATTTTTCAGT-CACTGGAGGAGGATCCATGGCCAAGGGTGAAT-TCTAAGGA CCATATACCTGCCCTGGTTCGTAGCAATGCCTT-CTCAGAGAATTTTTTAGAGGTTTC AGCTGAGA-TAGCTCGAGAGAATGTCCAAGGTGTAGTCAT-ACCCTCAAAAGATCCAG AACCACTTGAAGAAAAT-TGCGCTAAAGCCCTGACTTTAAGGATACATGAT-TCTTTGA ATAATAGCCTTCCAATTGGCCTTGTGCC-TACTAATTCAACAAACACTGTCATGGACC AAAAAAATTTGAAGATGTCAACTCCTGGCCAAAT-GAAAGCCCAAGAAATTGAAAGAA CCCCTC-CAACAAACTTTAAAAGGACATTAGAAGAGTC-CAATTCTGGCCCCCTGATG AAGAAGCATAGACGAAATGGCT-TAAGTCGAAGTAGTGGTGCTCAGCCTGCAAGTCT CCCCACAACCTCACAGCGAAAGAACTCTGT-TAAACTCACCATGCGACGCAGACTTA GGGGCCAGAAGAAAATTGGAAATCCTTTACTTCAT-CAACACAGGAAAACTGTTTGTG TTTGCTGAAATG-CATCTGGGAAA (SEQ ID NO:102; >chr17:58740341-58740928), or a fragment thereof at least 8, 10, 12, 14, 16, 18, or 20 nucleotides in length.

Therefore, in some embodiments, the capture probe has the nucleic acid sequence: GCGGTCCCCTCAGCCCCGTT-TACCTGCGGCTCCGGCGTCCGTAGCCACCGCCCC CGTACCTGCGGGGTGGCGGTCCCCGGCGGCTG-TGGTGTGAGTCCGGGGGGCGG CCGTAGCGCGC-CAT-TTGCACCCGCAGCTCGCGGCCGTCCAGCACGG-CCCCGTCC ATGGCATCCAT-AGCGTCCTCAGCGTCGCGCTTGTCGT-GAAAGCGAACGAAGGCGA AG (SEQ ID NO:103; >chr17:74732858-74733075), or a fragment thereof at least 8, 10, 12, 14, 16, 18, or 20 nucleotides in length.

Therefore, in some embodiments, the capture probe has the nucleic acid sequence: CCGCCGGGGAGAAGGAT-GAAGGACAAACAGAAGAAGAAGAAGGAGCGC-ACGTGG GCCGAGGCCGCGCGCCTGGT-GAGGCGGACAGCC (SEQ ID NO:104; >chr20:30946564-30946650), or a fragment thereof at least 8, 10, 12, 14, 16, 18, or 20 nucleotides in length.

Therefore, in some embodiments, the capture probe has the nucleic acid sequence: CGTCTCGTTCAACC-GATGGGGGTTGTGAAT-TTTGTGTTCAGAGCGTCAGAGGACTT GCAGGT-GAAATAGCTTCCT (SEQ ID NO:105; >chr20:30947535-30947609), or a fragment thereof at least 8, 10, 12, 14, 16, 18, or 20 nucleotides in length.

Therefore, in some embodiments, the capture probe has the nucleic acid sequence: TTTATATTTCTTCAGGTATT-AGAAAACTACTCGGATGCTCCAATGACAC-CAAAACAG ATTCTGCAGGTCAT-AGAGGCAGAAGGACTAAAGGAAATGAGGTTTG-TATTGTTCTT G (SEQ ID NO:106; >chr20:30954172-30954285), or a fragment thereof at least 8, 10, 12, 14, 16, 18, or 20 nucleotides in length.

Therefore, in some embodiments, the capture probe has the nucleic acid sequence: TCTTTTGTGGTTTTA-CAGTGGGACTTCCCCTCTCGCATGCCTCAATGC-TATGCTACA TTCCAATTCAAGAGGAG-GAGAGGGGTTGTTTTATAAACTGCCTGGCCGAA-TCAGCC TTTTCACGCTCAAGGTAAGTGATATGAAC (SEQ ID NO:107; >chr20:30956800-30956941), or a fragment thereof at least 8, 10, 12, 14, 16, 18, or 20 nucleotides in length.

Therefore, in some embodiments, the capture probe has the nucleic acid sequence: ACCTTGCTGT-CACAGAAGGATGCCCTGCAGTGGTCTCGC-CATCCAGCTACAGTGG AGGGAGAG-GAGCCAGAGGACACGGCTGATGTGGAGAGCT-GTGGGTCTAATGAAG CCAGCACTGTGAGTGGT-GAAAACGATGGTAAGGACCCTTTAA (SEQ ID NO:108; >chr20:31015916-31016066), or a fragment thereof at least 8, 10, 12, 14, 16, 18, or 20 nucleotides in length.

Therefore, in some embodiments, the capture probe has the nucleic acid sequence: TTTCCTCTCTTCCAGTATCTCTTGATGAAA-CATCTTCGAACGCATCCTGTTCTACAGA ATCTCAGAGTCGACCTCTTTC-CAATCCCAGGGACAGCTACAGAGCTTCCTCACAGG TAAGGAAGAGGTAG (SEQ ID NO:109; >chr20:31016113-31016240), or a fragment thereof at least 8, 10, 12, 14, 16, 18, or 20 nucleotides in length.

Therefore, in some embodiments, the capture probe has the nucleic acid sequence: TCTCTTG-GAACGCAGGCGAACAAACAAAAGAAAAA-GACTGGGGTGATGCTGCCTC GAGTTGTCCTGACTCCTCT-GAAGGTAAACGGGGCCCACGTGGAATCTG-CATCAGG TATGTGTAAACTCA (SEQ ID NO:110; >chr20:31017126-31017249), or a fragment thereof at least 8, 10, 12, 14, 16, 18, or 20 nucleotides in length.

Therefore, in some embodiments, the capture probe has the nucleic acid sequence: ATGCTGTGCCTTCAGGGTTCTCGGGCTGCCACGCC-GATGGCGAGAGCGGCAGCC CGTCCAGCAGCAGCAGCGGCTCTCTGGCCCTGG-GCAGCGCTGCTATTCGTGGCCA GGCCGAGGT-CACCCAGGACCCTGCCCCGCTCCT-GAGAGGCTTCCGGAAGCCAGC CACAGGT-GAGTGGCGTGGCA (SEQ ID NO:111; >chr20:31017689-31017871), or a fragment thereof at least 8, 10, 12, 14, 16, 18, or 20 nucleotides in length.

Therefore, in some embodiments, the capture probe has the nucleic acid sequence: CTTCAAAAATCATAGGT-CAAATGAAGCGCAACAGAGGGGAAGAAATAGAT-TTTGAG ACACCTGGGTCCATTCTTGTCAACAC-CAACCTCCGTGCCCTGATCAACTCTCGGAC CTTCCATGCCTTACCAT-CACACTTCCAGCAGCAGCTCCTCTTCCTCCTGCCT-GAAGT AGACAGACAGGTGCACATGGGCAGC (SEQ ID NO:112; >chr20:31019109-31019302), or a fragment thereof at least 8, 10, 12, 14, 16, 18, or 20 nucleotides in length.

Therefore, in some embodiments, the capture probe has the nucleic acid sequence: CCTT-GATCCTTCTAGGTGGGGACG-GATGGCCTGTTGCGTCTCAGCAGCAGTGCAC TAAATAACGAGTTTTTACC- CATGCGGCTCAGAGCTGGCGGGAGCGCCTGGCT-GAT GGTATGTAGACTTGGT (SEQ ID NO:113; >chr20:31019371-31019497), or a fragment thereof at least 8, 10, 12, 14, 16, 18, or 20 nucleotides in length.

Therefore, in some embodiments, the capture probe has the nucleic acid sequence: TTTATTTCTCCCTAGGT-GAATTTACTCATGAGATGCAAGTCAGGA-TACGACAGGAAA TGGAGAAGGAAAAGAAGGTG-GAACAATGGAAAGAAAAGTTCTTTGAAGACTACTAT GGACAGAAGTAAGGCAGTTGGAG (SEQ ID NO:114; >chr20:31020668-31020803), or a fragment thereof at least 8, 10, 12, 14, 16, 18, or 20 nucleotides in length.

Therefore, in some embodiments, the capture probe has the nucleic acid sequence: GATTTTGAT-TTGCAGGCTGGGTTTGACCAAAGAAGAGTCAT-TGCAGCAGAACGTGG GCCAGGAGGAGGCT-GAAATCAAAAGTGGCTTGTGTGTCCCAGGAGA-ATCAGTGCG TATACAGCGTGGTCCAGC-CACCCGACAGCGAGATGGGCATTT-TAAGAAACGCTCTC GGCCA-GATCTCCGAACCAGAGCCAGAAGGAATCTGTA-CAAAAAAACAGGAGTCAGA ACAAGCAGGGGTTGCTAAGGATGCAAAATCTG-TGGCCTCAGATGTTCCCCTCTACA AGGATGGG-GAGGCTAAGACTGACCCAGCAGGGCT-GAGCAGTCCCCATCTGCCAG GCA-CATCCTCTGCAGCACCCGACCTGGAGGGTCCCGAAT-TCCCAGTTGAGTCTGT GGCTTCTCGGATCCAGGCTGAGCCA-GACAACTTGGCACGTGCCTCTGCATCTCCA GACAGAATTCCTAGCCTGCCTCAGGAAACTGTG-GATCAGGAACCCAAGGATCAGAA GAG-GAAATCCTTTGAGCAGGCGGCCTCTG-CATCCTTTCCCGAAAAGAAGCCCCGG CTTGAAGATCGTCAGTCCTTTCGTAACACAATT-GAAAGTGTTCACACCGAAAAGCCA CAGCC-CACTAAAGAGGAGCCCAAAGTCCCGCC-CATCCGGGTAGGAGACTGTTTG (SEQ ID NO: 115; >chr20:31021072-31021735), or a fragment thereof at least 8, 10, 12, 14, 16, 18, or 20 nucleotides in length.

Therefore, in some embodiments, the capture probe has the nucleic acid sequence: ATTCTTTTTTGCAGATT-CAACTTTCACGTATCAAACCACCCTGGGTGGT-TAAAGGT CAGCCCACTTACCAGATATGCCCCCG-GATCATCCCCACCACGGAGTCCTCCTGCC GGGGTTGGACTGGCGCCAGGACCCTCGCAGACAT-TAAAGCCCGTGCTCTGCAGGT CCGAGGGGCGAGAGGTCACCACTGCCAT-AGAGAGGCGGCCACCACTGCCATCGG AGGGGGGGGTGGCCCGGGTG-GAGGTGGCGGCGGGGCCACCGATGAGGGAGGTG GCAGAGGCAGCAGCAGTGGTGATGGTGGT-GAGGCCTGTGGCCACCCTGAGCCCA GGG-GAGGCCCGAGCACCCCTGGAAAGTGTACGTCA-GATCTACAGCGAACACAACT ACTGCCGCCTTATCCTCTAAATGGGGAGCAT-ACCCAGGCCGGAACTGCCATGTCCA GAGCTAG-GAGAGAGGACCTGCCTTCTCTGAGAAAGGAG-GAAAGCTGCCTACTACA GAGGGCTACAGTTGGACTCACAGATGGGCTAG-GAGATGCCTCCCAACTCCCCGTT GCTCC-CACTGGGGACCAGCCATGCCAGGCCTTGCCCC-TACTGTCCTCCCAAACCT CAGTAGCTGAGAGATTAGTG-GAGCAGCCTCAGTTGCATCCGGATGTTAGAACT-GAA TGTGAGTCTGGCACCACTTCCTGGGAAAGT-GATGATGAGGAGCAAGGACCCACCG TTCCTGCAGACAATGGTCCCAT-TCTGTCTCTAGTGGGAGATGATACATTAGAGAAA GGAACTGGCCAAGCTCTTGACAGTCATCCCACTAT-GAAGGATCCTGTAAATGTGAC CCCCAGTTC-CACACCTGAATCCTCACCGACTGAT-TGCCTGCAGAACAGAGCATTTG ATGACGAATTAGGGCTTGGTGGCTCATGCCCTCC-TATGAGGGAAAGTGATACTAGA CAAGAAAACTT-GAAAACCAAGGCTCTCGTTTCTAACAGTTCTTTG-CATTGGATACCC ATCCCATCGAATGATGAGGTAGTGAAACAGCC-CAAACCAGAATCCAGAGAACACAT ACCATCTGTT-GAGCCCCAGGTTGGAGAGGAGTGG-GAGAAAGCTGCTCCCACCCCT CCTGCATTGCCTGGGGATTTGACAGCTGAG-GAGGGTCTAGATCCTCTTGACAGCCT TACTT-CACTCTGGACTGTGCCATCTCGAG-GAGGCAGTGACAGCAATGGCAGTTACT GTCAACAGGTGGACATTGAAAAGCTGAAAAT-CAACGGAGACTCTGAAGCACTGAGT CCTCACGGT-GAGTCCACGGATACAGCCTCTGACTTTGAAGGT-CACCTCACGGAGG ACAGCAGT-GAGGCTGACACTAGAGAAGCTGCAGTGACAAAGG-GATCTTCGGTGGA CAAGGATGAGAAACCCAATTG-GAACCAATCTGCCCCCACTGTCCAAGGTGAATGGTG ACATGCGTCTGGTTACAAGGACAGATGG-GATGGTTGCTCCTCAGAGCTGGGTGTCT CGAGTATGTGCGGTCCGCCAAAAGATCCCAGAT-TCCCTACTGCTGGCCAGTACTGA GTACCAGC-CAAGAGCCGTGTGCCTGTC-CATGCCTGGGTCCTCAGTGGAGGCCACT AACCCACTTGT-GATGCAGTTGCTGCAGGGTAGCTTGCCCCTA-GAGAAGGTTCTTCC ACCAGCCCACGATGACAG-CATGTCAGAATCCCCACAAGTACCACTTACAAAA-GACC AGAGCCATGGCTCGCTACGCATGGGATCTT-TACATGGTCTTGGAAAAAACAGTGGC ATGGTTGATGGAAGCAGCCCCAGTTCTT-TAAGGGCTTTGAAGGAGCCTCTTCTGCC AGA-TAGCTGTGAAACAGGCACTGGTCTTGCCAGGATT-GAGGCCACCCAGGCTCCT GGAGCACCCCAAAAGAATTGCAAGGCAGTCC-CAAGTTTTGACTCCCTCCATCCAGT GACAAATCC-CATTACATCCTCTAGGAAACTGGAAGAAATGGAT-TCCAAAGAGCAGTT CTCTTCCTTTAGTTGTGAA-GATCAGAAGGAAGTCCGTGCTATGT-CACAGGACAGTA ATTCAAATGCTGCTCCAG-GAAAGAGCCCAGGAGATCTTACTACCTCGAGA-ACACCT CGTTTCTCATCTCCAAATGT-GATCTCCTTTGGTCCAGAGCA-GACAGGTCGGGCCCT GGGTGATCAGAGCAATGT-TACAGGCCAAGGGAAGAAGCTTTTTGGCTCTG-GGAAT GTGGCTGCAACCCTTCAGCGCCCCAGG-CCTGCGGACCCGATGCCTCTTCCTGCTG AGATCCCTCCAGTTTTTCCCAGTGG-GAAGTTGGGACCAAGCACAAACTCCATGTCT GGTGGGGTACAGACTCCAAGGGAAGACTGGGCTC-CAAAGCCACATGCCTTTGTTG GCAGCGT-CAAGAATGAGAAGACTTTTGTGGGGGGTCCTCT-TAAGGCAAATGCCGA GAACAGGAAAGCTACTGGGCATAGTCCCCTG-GAACTGGTGGGTCACTTGGAAGGG ATGCCCTTTGTCATGGACTTGCCCTTCTGGAAAT-TACCCCGAGAGCCAGGGAAGGG GCTCAGT-GAGCCTCTGGAGCCTTCTTCTCTCCCCTCC- CAACTCAGCATCAAGCAGG CATTTTATGGGAAGCTTTCTAAACTCCAACT- GAGTTCCACCAGCTTTAATTATTCCTC TAGCTCTCC- CACCTTTCCCAAAGGCCTTGCTG- GAAGTGTGGTGCAGCTGAGCCACA AAGCAAACTTTGGTGCGAGCCACAGTGCAT- CACTTTCCTTGCAAATGTTCACTGACA GCAGCACGGTG- GAAAGCATCTCGCTCCAGTGTGCGTGCAGCCT- GAAAGCCATGAT CATGTGC- CAAGGCTGCGGTGCGTTCTGTCACGATGACTGT- ATTGGACCCTCAAAGC TCTGTGTAT- TGTGCCTTGTGGTGAGATAATAAATTATGGCCATG (SEQ ID NO: 116; >chr20:31022220-31025156), or a fragment thereof at least 8, 10, 12, 14, 16, 18, or 20 nucleotides in length.

Therefore, in some embodiments, the capture probe has the nucleic acid sequence: TCAAT- TTTGTTTCAGGACCTGCTTCGCTGCCGTGTCCT- GACTTCTGGAATCTTTGAG ACCAAGTTCCAGGTGGACAAAGT- CAACTTCCAGTAAGCCAACTGTTA (SEQ ID NO: 117; >chr20:57484390-57484493), or a fragment thereof at least 8, 10, 12, 14, 16, 18, or 20 nucleotides in length.

Therefore, in some embodiments, the capture probe has the nucleic acid sequence: CCTCCTCCCCACCAG- CATGTTTGACGTGGGTGGCCAGCGCGAT- GAACGCCGCAAG TGGATCCAGTGCTT- CAACGGTAGGATGCTGTGGG (SEQ ID NO:118; >chr20:57484561-57484649), or a fragment thereof at least 8, 10, 12, 14, 16, 18, or 20 nucleotides in length.

Therefore, in some embodiments, the capture probe has the nucleic acid sequence: CTCTCTTTGGTTAA- GATGTGACTGCCAT- CATCTTCGTGGTGGCCAGCAGCAGCTAC AACATGGTCATCCGGGAGGACAACCAGAC- CAACCGCCTGCAGGAGGCTCTGAACC TCTT- CAAGAGCATCTGGAACAACAGGTTTGTG- GAGTGACC (SEQ ID NO:119; >chr20:57484724-57484874), or a fragment thereof at least 8, 10, 12, 14, 16, 18, or 20 nucleotides in length.

Therefore, in some embodiments, the capture probe has the nucleic acid sequence: CCTCCCTTCTTGTA- GATGGCTGCGCACCATCTCTGTGATCCTGTTCCT- CAACAAGC AAGATCTGCTCGCT- GAGAAAGTCCTTGCTGGGAAATCGAAGATTGAG- GACTACTTT CCAGAATTTGCTCGCTACAC- TACTCCTGAGGATGGTGTGTATGGCTTCC (SEQ ID NO:120; >chr20:57484991-57485151), or a fragment thereof at least 8, 10, 12, 14, 16, 18, or 20 nucleotides in length.

Therefore, in some embodiments, the capture probe has the nucleic acid sequence: TCCCTTTTTATATAGC- TACTCCCGAGCCCGGAGAGGACC- CACGCGTGACCCGGGC CAAGTACTTCAT- TCGAGATGAGTTTCTGGTGAGTCGAGCCTGT (SEQ ID NO:121; >chr20:57485374-57485471), or a fragment thereof at least 8, 10, 12, 14, 16, 18, or 20 nucleotides in length.

Therefore, in some embodiments, the capture probe has the nucleic acid sequence: TGTTTGTGCCCGCAGAG- GATCAGCACTGCCAGTGGAGATGGGCGTCAC- TACTGCT ACCCTCATTT- CACCTGCGCTGTGGACACTGAGAACATCCGCC- GTGTGTTCAACGAC TGCCGTGACATCATTCAGCG- CATGCACCTTCGTCAGTACGAGCTGCTCTAAGAAGG GAACCCCCAA (SEQ ID NO:122; >chr20:57485723-57485899), or a fragment thereof at least 8, 10, 12, 14, 16, 18, or 20 nucleotides in length.

Therefore, in some embodiments, the capture probe has the nucleic acid sequence: TAAAAATGG- CATGGCTCAGAATCGCCCAGATCTTTCAC- GATCTCTCGACCGCCTCC TGT- CACGCTCCCGTCCGCCGCCACCTCCACCAC- CGCCACCGCCACCGCCACGACC ACGGTCTCTA- GACCGAGAACGACGCTCCCGGGATCGGGATCTT- GATCTATGCCTG CAACCAAGGAAA (SEQ ID NO:123; >chr21:44513197-44513374), or a fragment thereof at least 8, 10, 12, 14, 16, 18, or 20 nucleotides in length.

Therefore, in some embodiments, the capture probe has the nucleic acid sequence: CGGGCACAGGAATACT- CACTTCTTGCGACGGCGGCCATA- CAGCTCCCGCCGCAGC TCTCTGGAAATGGGCTT- CAAATGCATGAAGTTGCAGAAGCCGCCTCGTGT- GCATTC TCTGTGGGTGGGTTGG (SEQ ID NO:124; >chr21:44514562-44514688), or a fragment thereof at least 8, 10, 12, 14, 16, 18, or 20 nucleotides in length.

Therefore, in some embodiments, the capture probe has the nucleic acid sequence: CCACTCCTCACTCACCC- CATCTCATACTGACGGCAGCAGGCTTCTCT- GAAGTCCGT CACGGGTGACAGCTCGGCGTG- GATCGGCTGTCCATTAAACCAACGGTTATTCAAGT CAATCACAGCCTTTTCCGCATCTTCCT- CACGGCGAAACTGAAAAGACAAAAA (SEQ ID NO:125; >chr21:44514750-44514913), or a fragment thereof at least 8, 10, 12, 14, 16, 18, or 20 nucleotides in length.

Therefore, in some embodiments, the capture probe has the nucleic acid sequence: CGCCCTGGCTCC- TACCTTGACGTACACGTTCCC- CACCAGGTGGTCTCCCAGGTTGT CACAGACGTT- CATCTCCTCTACTTCCCCATACTTCTCCTCCATT- TCTGTAAAAACCTC CTGAAGGGAGACCAC (SEQ ID NO:126; >chr21:44515533-44515661), or a fragment thereof at least 8, 10, 12, 14, 16, 18, or 20 nucleotides in length.

Therefore, in some embodiments, the capture probe has the nucleic acid sequence: GTTCAGTTCTCTCACCT- CAAAAAACTCATCATAGTGTTCCTGCATCTCCA- CATCGCT CACGGCACCTGCAAACAACAGAA (SEQ ID NO:127; >chr21:44515789-44515868), or a fragment thereof at least 8, 10, 12, 14, 16, 18, or 20 nucleotides in length.

Therefore, in some embodiments, the capture probe has the nucleic acid sequence: CTTGTATGAACTTA- CAGCGCAAACCGTCAGCAGACTGGGAAGAGTTTT- GAGGGTTA CGGTAAATGTT- CAAGAGGGCAATGGTCTGAAATACAAAACG (SEQ ID NO:128; >chr21:44520548-44520644), or a fragment thereof at least 8, 10, 12, 14, 16, 18, or 20 nucleotides in length.

Therefore, in some embodiments, the capture probe has the nucleic acid sequence: CTC- TATGTCAGCAGCTCAGAAGCCAACATTATTTGTCT- CAATTAAGAGTGGGCTCTT TAACACCATTGTTT- TAAAAAAATTTCTCCAACTGTGGGACTTACAG- TGTGAGCCGTC AGCCGTCTGTGCACTGTTTTGGG- GATTACGATAGATGTTTTGAATCAAGATGGTCTG CGGGGAAAAAAA (SEQ ID NO:129; >chr21:44521375-44521557), or a fragment thereof at least 8, 10, 12, 14, 16, 18, or 20 nucleotides in length.

Therefore, in some embodiments, the capture probe has the nucleic acid sequence: AAAAGGCAAACAAACCTGGCTAAACGTCGGTTT- ATTGTGCAACCGAGAGCACCTGT CTCCATGACGA-CATGCTCCAATTTTGAAATAAAAT-GAACAGTTGACTCTGTAAGGGA AAATG (SEQ ID NO:130; >chr21:44524410-44524527), or a fragment thereof at least 8, 10, 12, 14, 16, 18, or 20 nucleotides in length.

Therefore, in some embodiments, the capture probe has the nucleic acid sequence: GGGGCTCCCACT-CACTTGTCTTTCTCGGTGCCGAAGATGGAGGCCA-GATACTCCG CCATTTCCCACCCGCCGCC (SEQ ID NO:131; >chr21:44527546-44527619), or a fragment thereof at least 8, 10, 12, 14, 16, 18, or 20 nucleotides in length.

A number of embodiments of the invention have been described. Nevertheless, it will be understood that various modifications may be made without departing from the spirit and scope of the invention. Accordingly, other embodiments are within the scope of the following claims.

EXAMPLES

Example 1: Inexpensive and Scalable Multiplex Sequencing Assay Enables Identification and Treatment of Individuals with Somatic Mutations Clonal Hematopoiesis (CH)

Aging is associated with the accumulation of somatic mutations across cells. Similar to other stem cells, hematopoietic stem cells (HSCs) accumulate mutations leading to increasing genetic diversity across an individual's lifetime. Individual HSCs are estimated to acquire 200 mutations per decade genome-wide, with 1 mutation per decade occurring within an exonic region. While the vast majority of such mutations do not have substantive impacts on cellular fitness, occasionally one such mutation may promote vitality and proliferation termed clonal hematopoiesis (CH).

CH has long been hypothesized as a key precursor in a sequential model of leukemogenesis. Age-related HSC clonal abnormalities in asymptomatic individuals was first recognized three decades ago through the analyses of non-random X-inactivation patterns derived from peripheral leukocytes of women. Population-based next-generation sequencing over the last decade has shown that CH is surprisingly common with approximately 1 in 10 asymptomatic adults older than 70 years affected. Using whole exome sequences of blood DNA originally aimed to discover rare germline disruptive coding alleles contributing to risk for common complex diseases, investigators employed methods to detect acquired mutations. 'Clonal hematopoiesis of indeterminate potential' (CHIP) is the presence of a hematologic malignancy driver mutation (typically in DNMT3A, TET2, ASXL1, JAK2) with high variant allele frequency in blood (i.e., >2%) indicative of clonality. While CHIP is a strong risk factor for hematologic malignancy, risk is not absolute with ~0.5%/year progression from CHIP to hematologic malignancy.

A more surprising finding related to CHIP is that its implications for coronary artery disease may be a more important than hematologic malignancy. In several datasets, CHIP is associated with a 1.6-1.9-fold risk for coronary artery disease (CAD), and thus larger absolute risk increase for CAD compared to hematologic malignancy. Among asymptomatic individuals, individuals with CHIP have a greater burden of subclinical coronary atherosclerosis compared to those without. Consistent with the human observations, irradiated mice transplanted with $Tet2^{-/-}$ bone marrow versus transplanted with wild type bone marrow have a greater burden of supravalvular and descending aortic atherosclerosis. Both humans and mice with CHIP mutations in hematopoietic stem cells have greater concentrations of circulating inflammatory cytokines. Inhibition of the NLRP3 inflammasome mitigates atherosclerosis to a greater degree in irradiated mice transplanted with Tet2−/− bone marrow versus transplanted with wild type bone marrow. Similarly, genetic deficiency of IL6-receptor, in the NLRP3 pathway, through the presence of a common IL6R missense mutation in humans is associated with a greater reduction in cardiovascular disease risk among those with CHIP versus without. These data imply that for patients with CHIP, a tailored anti-inflammatory approach may be highly effective at addressing CHIP-associated cardiovascular disease risk. The increasingly robust therapeutic hypothesis is ripe for testing in placebo-controlled clinical trials.

Additional forms of CH have also been detected from the analysis of blood DNA. Larger chromosomal rearrangements, often term mosaic chromosomal alterations (mCAs) or clonal somatic copy number alterations, have been identified from large-scale blood DNA-derived genome-wide genotyping. While CHIP is strongly associated with myeloid malignancies, mCAs are strongly associated with lymphoid malignancies. Unlike CHIP, mCAs are not associated with CAD. Additionally, mCAs may represent more widespread immunologic dysfunction as they predict diverse incident cancers and infections.

Existing Methods to Detect Clonal Hematopoiesis and Other Premalignant Somatic Mutations Currently to detect CHIP requires either a whole genome/whole exome sequence or a selective amplification of DNA followed by sequencing (e.g. the Illumina TruSight Oncology test). Current approaches that accomplish this range in cost from about $250-$1000. The assay disclosed herein to detect CHIP is significantly more cost effective (e.g. about $10) and scalable than comparable approaches that are currently in use.

TABLE 1

| Technology | Depth | Variant Allele Fraction detection threshold | Cost (approx.) |
|---|---|---|---|
| Whole genome | 30x | >10% | $750 |
| Whole exome | 50x | >5% | $250 |
| Illumina TruSight Myeloid | 500x | >1% | $200 |
| Custom Hybrid Capture | 500x | >1% | $100 |
| Amplicon Sequencing | 500x | >1% | $50 |
| ArcherDx Error Corrected Myeloid panel | 5000x | >0.1% | $400 |

Highly Scalable Method to Detect Clonal Hematopoiesis and Other Premalignant Somatic Mutations Disclosed herein is a highly scalable and cost-effective method to identify individuals with clonal hematopoiesis of indeterminate potential (CHIP).

An analysis of 127,000 individuals in the general population was first performed to detect CHIP in the Trans-Omics for Precision Medicine (TOPMed) Program. 5,682 individuals with CHIP were identified. The distribution of genes was then analyzed revealing that CHIP has a skewed distribution with an overwhelming majority of the mutations that were detected in just a small handful of genes (FIG. 1). Within those genes, the distribution of CHIP mutations was non-uniform, such that a specific subset of the genes contained the majority of the signal.

Building on this analysis, a specific set of DNA regions was identified that include just about 45 kb of DNA but encompass >95% of all CHIP observed in the general population. The genes include: ASXL1, ASXL2, BRCC3, CBL, DNMT3A, ETNK1, GNAS, GNB1, IDH1, IDH2, JAK2, KIT, KRAS, MPL, NRAS, PPM1D, SETBP1, SF3B1, SRSF2, TET2, TP53, U2AF1, ZBTB33, ZNF318. This enables the disclosed assay to be highly specific in the DNA amplified which enables both the subsequent chemical reactions that perform the DNA extraction and enrichment to be executed with smaller quantities of input material and smaller quantities of enzymes which reduces cost and increases scalability as well as reducing the subsequent cost of sequencing at >500× depth.

Second, hybrid capture oligonucleotide probes were designed to selectively amplify this set of genomic intervals (using the Twist Bioscience hybrid capture technology). Alternative hybrid capture reagents or reagents that selectively amplify DNA regions are equally effective for this step.

Third, two highly cost effective and scalable genomic library preparation methods were developed that are compatible with the hybrid capture system to enable efficient processing of genomic DNA from multiple individuals at the same time through library preparation and DNA barcoding.

Figure 2:
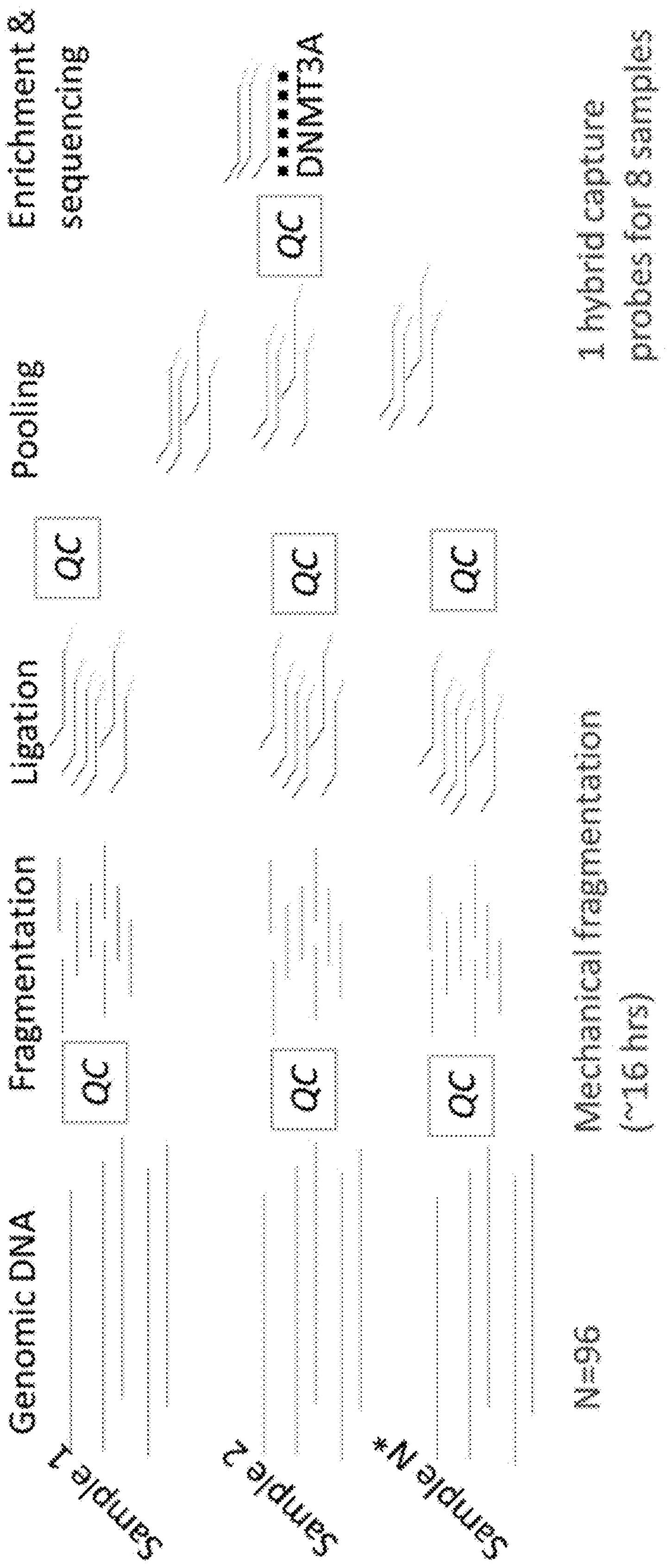
FIG. 2 illustrates standard library preparation workflow with mechanical fragmentation.
Figure 3:
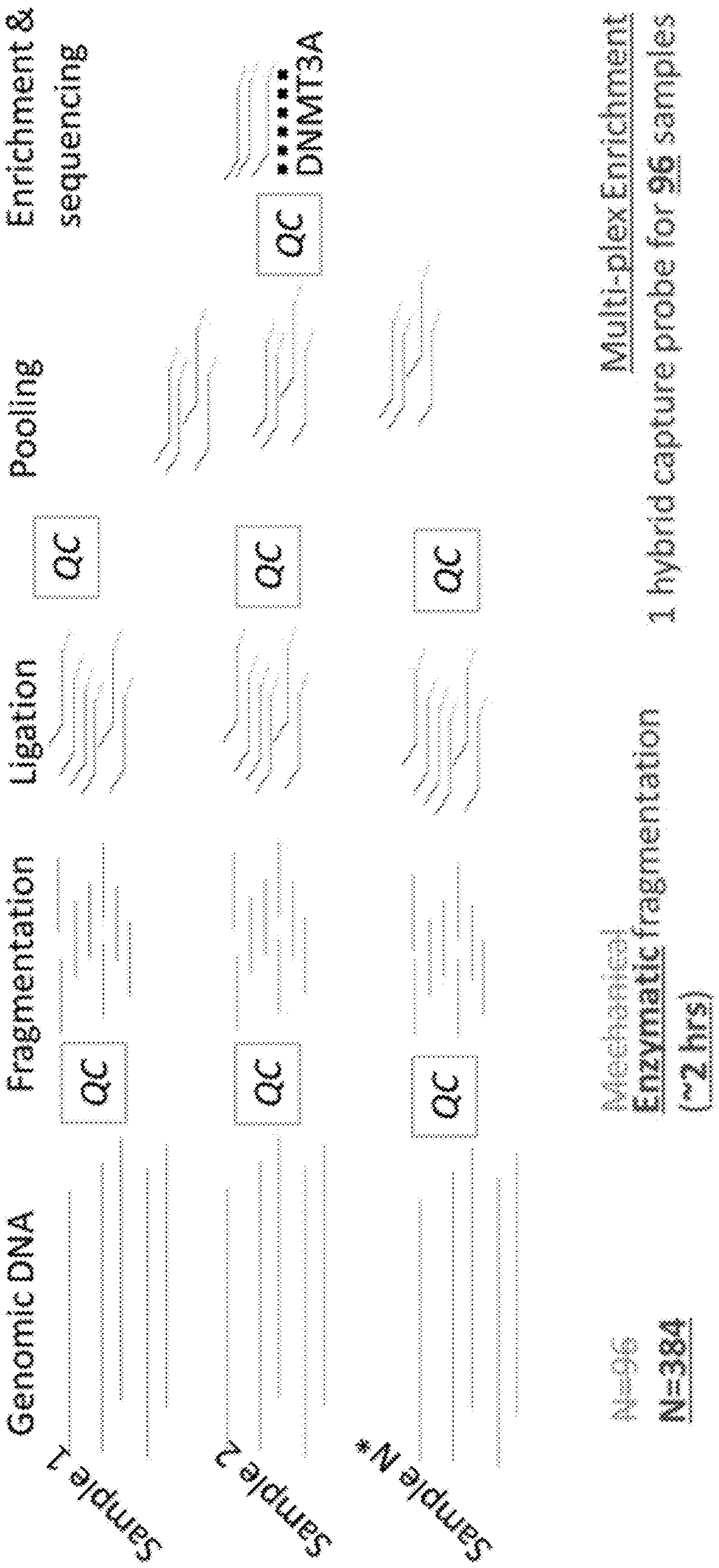
FIG. 3 illustrates a multiplex enrichment protocol with enzymatic fragmentation.
Figure 4:
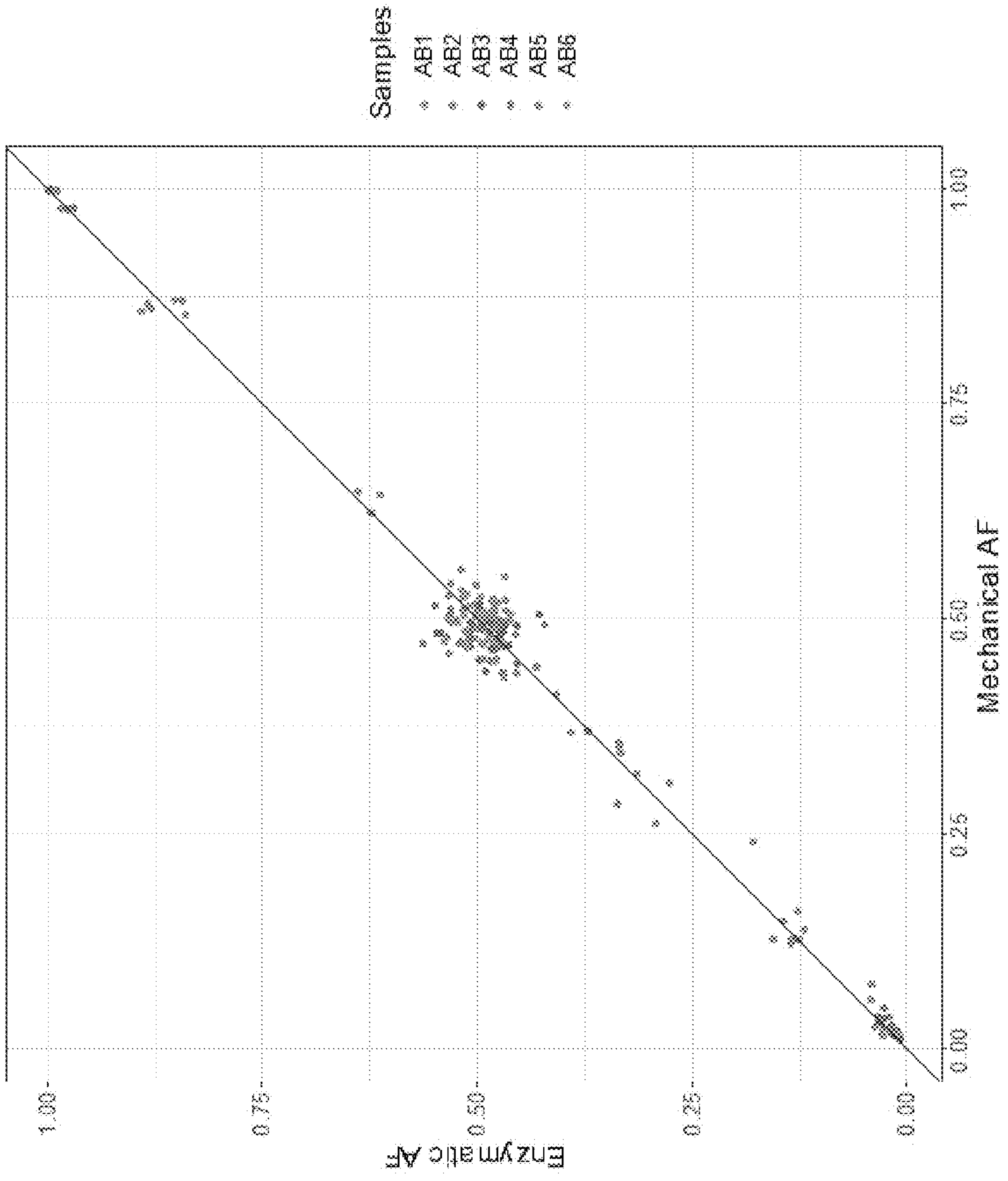
FIG. 4 is a comparison of standard mechanical fragmentation and 1 hybrid capture probe for 8 sample library preparation demonstrated highly concordant results with enzymatic fragmentation, 96 sample multi-plex enrichment.

The first one is based on the Twist Bioscience NGS library preparation kit where a specific stoichiometry of the input DNA and enzymatic reactions were shown to enable "miniaturization" of the existing library preparation method and enable performing 5× more reactions than with the manufacturer's protocol. The protocol was compatible with both mechanical (FIG. 2) and enzymatic (FIG. 3) library techniques. FIG. 4 shows a comparison of standard mechanical fragmentation and 1 hybrid capture probe for 8 sample library preparation that demonstrated highly concordant results with enzymatic fragmentation, 96 sample multi-plex enrichment.

This method however still required extensive quantification, quality control and normalization of the input DNA material.

Figure 5:
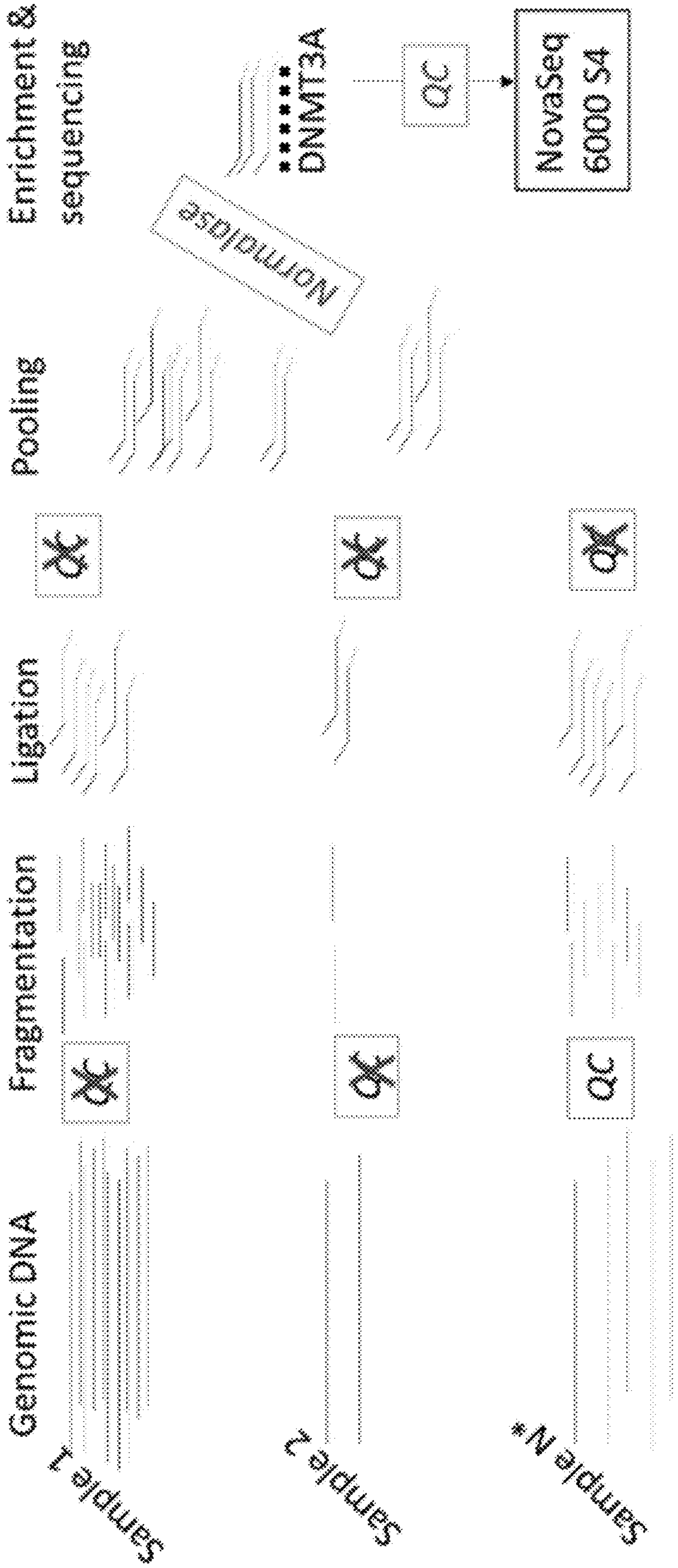
FIG. 5 illustrates use of normalase in the library preparation workflow.
Figure 6:
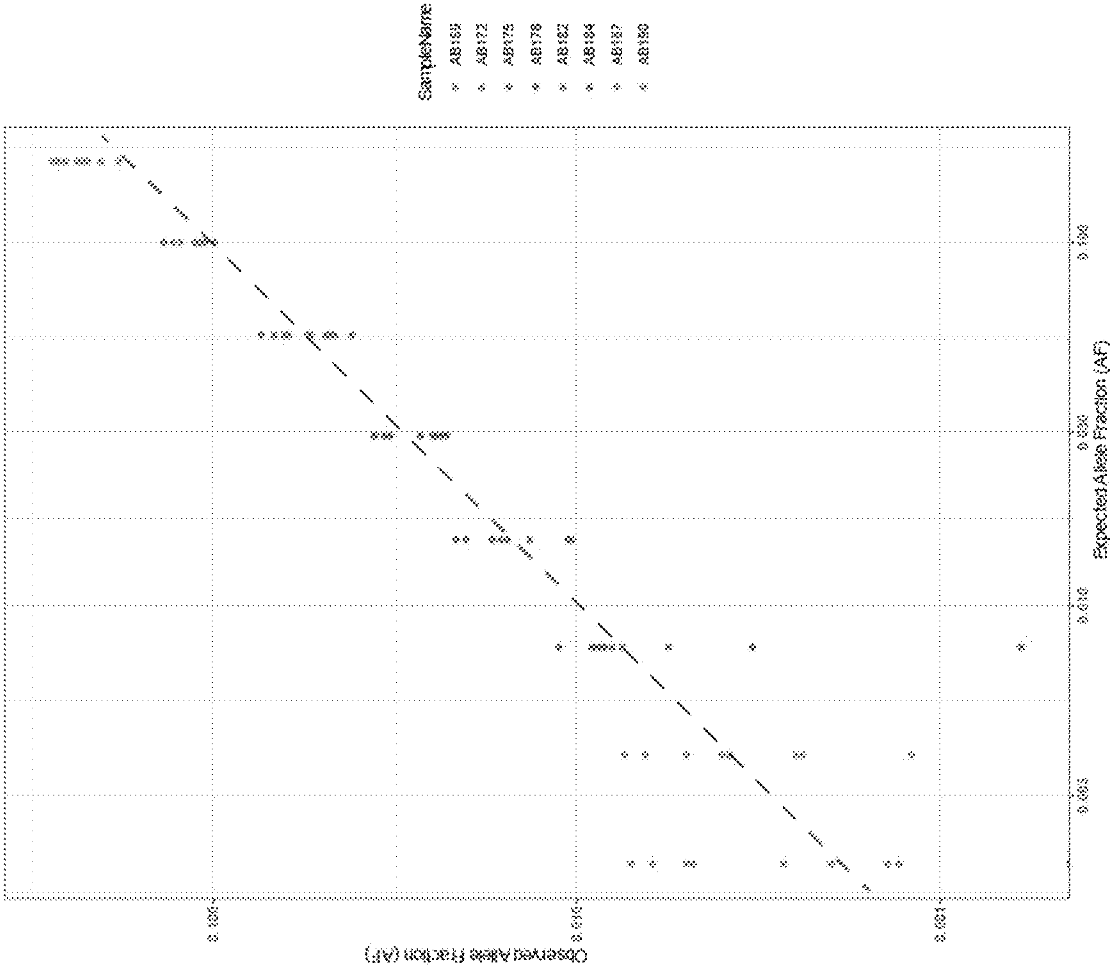
FIG. 6 shows observed allele fraction (AF) compared to expected AF in a limiting dilution experiment where DNA samples with known genotypes were combined at serial fixed ratios with a second sample of known genotype.

A second technology was therefore incorporated, referred to herein as "normalase", Normalase is an enzymatic process that ensures equimolar combinations of DNA in library preparation methods. By using the normalase in the genomic DNA system, the library preparation workflow was further simplified (eliminating the input quality control and normalization steps) and thereby reducing the cost of the process and increase the throughput further (FIG. 5).

Fourth, the hybrid capture oligonucleotide technology was combined with the scalable genomic library preparation method to detect CHIP. It was demonstrated that by combining the "miniaturized" enzymatic library preparation technique with the custom designed hybrid oligonucleotide probes 12 times the number of hybridization reactions could be performed as the Twist manufacturer's protocol (see Appendix Ill). The process was then setup on a standard liquid handling robot platform to enable preparation and sequencing (on a single liquid handling robot) of >5,000 samples/week.

Fifth, the barcoded DNA library was then sequenced on standard next-generation sequencing chemistry (Illumina NovoSeq 6000) and applied computational methods were performed for somatic mutation detection (e.g. GATK Mutect2, Varscan2) to the resulting output to detect CHIP.

Currently, the disclosed assay can be performed for approximately $5 per sample, which is about 50-fold less expensive than alternative technologies.

Method Performance

To quantify the limit of detection for the method a limiting dilution experiment was performed where a DNA sample with known genotype was combined at serial fixed ratios with a second sample of known genotype. These ratios were utilized to identify the expected allele fraction for a given variant. The disclosed method robustly detects variants present in >1% of DNA. Furthermore, beneath this 1% threshold, variants are detected down to about 0.1% allele fraction, albeit with less accuracy for the estimated allele fraction.

Use of this Assay to Identify and Treat Individuals at Increased Risk of Disease As studies detail new genotypic and phenotypic associations with CHIP, researchers and clinicians are confronted with the question of what preventative and therapeutic interventions could be taken to mitigate disease risk. Whole exome sequencing to detect CHIP is by no means a routine clinical test, though associations with CHIP are found with red-cell distribution width (RDW) and modest increases in total WBC count, tests that are clinically routine. Understanding which cohorts of patients could benefit from targeted CHIP testing could enable a precision-medicine approach to risk reduction. Additionally, many CHIP patients may be identified incidentally. Cell-free DNA analysis, intended to detect circulating tumor DNA to aid in early-cancer detection, is invariably confounded by the presence of CHIP, as the vast majority of cell-free DNA arises from hematopoietic cells.

An understanding of CHIP biology and its reciprocal relationship to a pro-inflammatory state presents numerous potential targets for therapy. As a genetic proxy of IL-6 inhibition, the presence of the inhibitory IL-6 receptor gene variant (IL6Rp.Asp358Ala) reduced the CVD risk in DNMT3A and TET2 CHIP carriers by about 50%, highlighting that inhibiting IL-6 signaling can decrease the risk of cardiovascular disease; of note, there was no effect seen in non-CHIP carriers. This is in keeping with studies which have found that IL-β blockade with canakinumab after MI reduced risk of death form cardiovascular disease, rates of nonfatal AMI and nonfatal stroke (CANTOS [Canakinumab Anti-inflammatory Thrombosis Outcomes Study]). Secondary analyses later demonstrated that a greater reduction was seen in those individuals who were TET2-CHIP carriers, or those with larger reductions in IL-6 or hsCRP. More broadly, colchicine, an FDA approved anti-gout medication that targets the NLRP3 inflammasome and IL-β activation has been shown in clinical trials (i.e. LoDoCo, LoDoCo2 and COLCOT) to reduce the risk of ischemic cardiovascular events.

Targeting individual mutations in CHIP could also represent a similar therapeutic strategy. Vitamin C metabolites activate TET2 and can mimic restoration of TET2 via enhancing 5-hydroxymethycytosine formation in TET2-deficient mice to reverse aberrant HSC self-renewal, presenting a potential preventive therapy for TET2-CHIP carriers. In JAK2 mutant CHIP, treatment with the approved JAK2 inhibitor ruxolitinib reduced abnormal neutrophil extracellular trap formation and deep vein thrombosis and JAK2 inhibition with fedratinib in Apoe−/− mice suppressed myelopoiesis and the development of atherosclerosis.

Use of this Assay to Identify and Treat Individuals at Increased Risk of Disease Due to Clonality Beyond the Hematopoietic System There is an increasing appreciation that clonal mosaicism is a common, yet underappreciated disease mechanism in many human tissues beyond blood including well documented examples in skin, esophagus, intestine, liver, lung, endometrium, and bladder (see table below). Similar to clonal hematopoiesis, a small set of genes makes up the preponderance of the observed mutational burden. Premalignant somatic mutations in these tissues also result in diverse diseases. Identification of these somatic mutations can be accomplished using the procedures outlined herein using DNA derived from these tissues. Similar to clonal hematopoiesis, the identification of clonality with this assay can enable specific therapeutic treatments to prevent/treat the associated disorders.

| Tissue | Illustrative Gene Sets with somatic mutations | Illustrative Diseases | Illustrative Treatments |
|---|---|---|---|
| Blood | DNMT3A, TET2, ASXL1, JAK2, GNAS, GNB, CBL, TP53, PPM1D, SF3B1, SRSF2, PIGA, BCOR, BCORL1, DNMT3A, ASXL1 | Hematologic neoplasms (Leukemia, Lymphoma, Myeloma, Aplastic Anemia, myeloproliferative neoplasms), Coronary artery disease, heart failure, COPD, Cirrhosis/NAFLD, osteoporosis | IL-6 inhibitor<br>IL-1Beta inhibitor<br>NLRP3 (inflammasome) modulator, JAK2 targeted inhibitor; spliceosome inhibitor; cardiovascular targeted therapy (statin, lipid lowering medication) |
| Skin | NOTCH1, NOTCH2, FAT1, TP53, NOTCH3, RBM10, BRAF, NF1, RASA2, CBL, MAP2K1, NRAS, ARID2, CDKN2A, PTEN, PPP6C, DDX3X | Skin cancer, psoriasis | NOTCH inhibitors,<br>TP53 modulating therapies |
| Esophagus | NOTCH1 > TP53 > FAT1, NOTCH2, NOTCH3, KMT2D, ZFP36L2, PPM1D, PIK3CA, CHEK2, PAX9, ARID1A, CUL3, AJUBA, ARID2, TP63, NFE2L2, CCND1 | Esophageal cancer, Barrett's esophagus | NOTCH targeted therapies, TP53 targeted therapies |
| Intestine | AXIN2, STAG2 NFKBIZ > ARID1A > PIGR > ZC3H12A, KRAS > FBXW7, TRAF3IP2, HNRNPF, ARID1B, BCOR, BCORL1, ETV6, RNF43, TP53 | Chron's Disease<br>Ulcerative colitis | Immune-modulators (IL-6, TNF-Alpha etc) |
| Liver | ALB, ACVR2A, ARID1A, ARID2, NCOR1, TP53, PKD1, KMT2D | Cirrhosis<br>Fatty Liver Disease | Immune system modulators |
| Lung | NOTCH1, FAT1, TP53, ARID1A, ARID2, FAT1, CHEK2, PTEN, CHEK2 | Lung cancer<br>COPD<br>Asthma<br>Idiopathic lung disease | Cell cycle inhibitors |
| Endometrium | PIK3CA, ARHGAP35, PIK3R1, FBXW7, ZFHX3, FOXA2, ERBB2, CHD4, KRAS, SPOP, PPP2R1A, ERBB3 | Endometriosis<br>Endometrial Cancer,<br>Ovarian cancer | PI3-Kinase targeted agents |
| Bladder/<br>Urothelium | KMT2D, KDM6A, ARID1A, RBM10, EP300, STAG2, NOTCH2, CDKN2A, CREBBP, FOXQ1, RHOA, ERCC2, KLF5, ZFP36L1, ELF3, GNA13, PTEN, TP53 | Bladder cancer<br>Cystitis | GSK-J1, GSK-J4, IOX1 |

Example 2

A cost-effective targeted sequencing assay that incorporates a combination of both unique molecular identifiers and unique dual indexes is employed as part of the library preparation. This enables bioinformatic removal of PCR duplicates and other sequencing artifacts. This assay also uses Twist Bioscience hybrid capture technology to selectively sequence up to ~10,000 loci of interest. With recent advances in the manufacturing process, the hybrid capture probes can be produced and put into production within 2 weeks. Samples are pooled and sequenced on the Illumina Novaseq 6000 platform at ~8M paired end reads/sample which translates to a depth of ~4000× after unique molecular index consensus calling, which is ample for detecting variants to ~0.1% VAF. Sequencing data will be analyzed through the DRAGEN pipeline as described above. This process is highly scalable. This enables identification of CHIP mutations present in collected and cryopreserved plasma of previously collected clinical cohorts.

This targeted sequencing assay enables an orthogonal technology to validate somatic SNVs/Indels that are identified. As it will have considerably greater sequencing depth and is more than an order of magnitude more sensitive than primary discovery technology, it can detect the true presence of mosaicism in tissues that a mosaic variant was not identified in and thereby overcome the small clone size limitation. More importantly, a 'gold standard' truth set will be extremely useful in evaluating the sensitivity and specificity of various computational somatic mutation detection algorithms.

Example 3: Deep Error-Corrected Sequencing Permits Ascertainment of Full Spectrum of CH Standard next generation DNA sequencing technologies (exome or genome) are unable to reliably identify genetic mutations present in <2% of the DNA due to the error rate associated with these technologies. To overcome this limitation, error-corrected sequencing methods use single molecule tagging with unique molecular identifiers to permit the robust detection of CH variants at an order of magnitude below the error rate of next generation sequencing (Young, A. L., et al. Nat. Commun. 2016 7:12484; Young, A. L., et al. Haematologica 2019 104:2410-2417). For somatic mutation studies, error-corrected sequencing has become the gold-standard in the field. This technology has led to a new appreciation of the prevalence of low- or medium-sized CH clones in various populations. For example, with standard DNA sequencing, CH is rarely detected in individuals <40 years old, but is present in ~20% of individuals over age 70.

In contrast, error-corrected sequencing detects CH in ~5% of individuals by age 30, ~50% of individuals by age 50 and >90% of individuals over 70 (Watson, C. J. et al. Science 2020 367:1449-1454). Importantly, to date, no study has applied error-corrected sequencing to identify the full spectrum of CH in patients with SCD. Moreover, the significance of low- or medium-sized CH clones is unknown.

Figure 7:
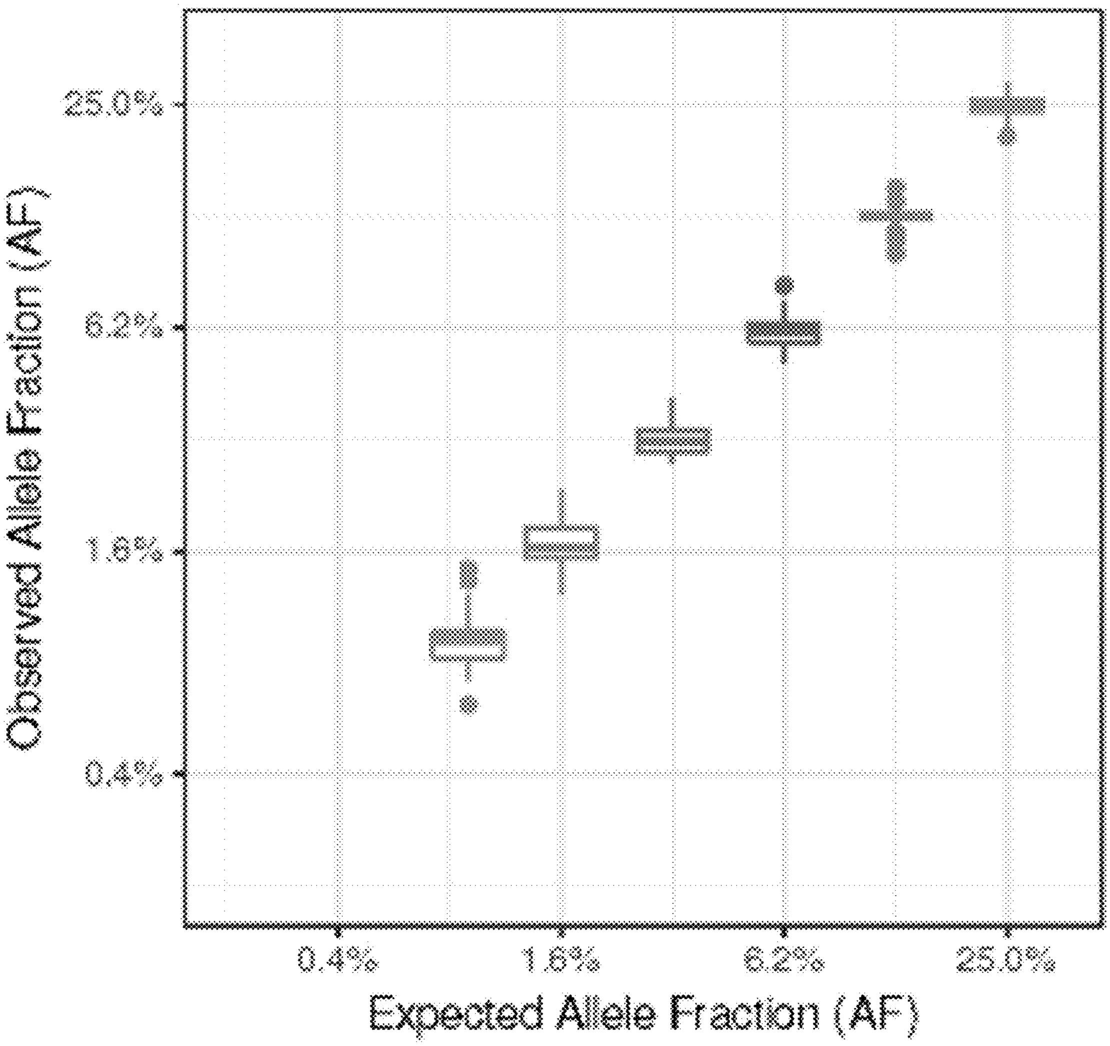
FIG. 7 shows robust correlation between observed vs expected variant allele fraction with novel CH assay across range of simulated CH clone sizes.

Assay Validation. To demonstrate the robustness of the CH UMI assay, a limiting dilution experiment was performed where a DNA sample with known genotype was combined at serial fixed ratios with a second sample of known genotype. These ratios were used to identify the expected allele fraction for a given variant (targeting a range of dilutions from 25% to 0.8%). This method robustly detected variants present to 0.8% of DNA. This experiment was performed in triplicate and representative data from one series of samples is shown (FIG. 7)

Figure 8:
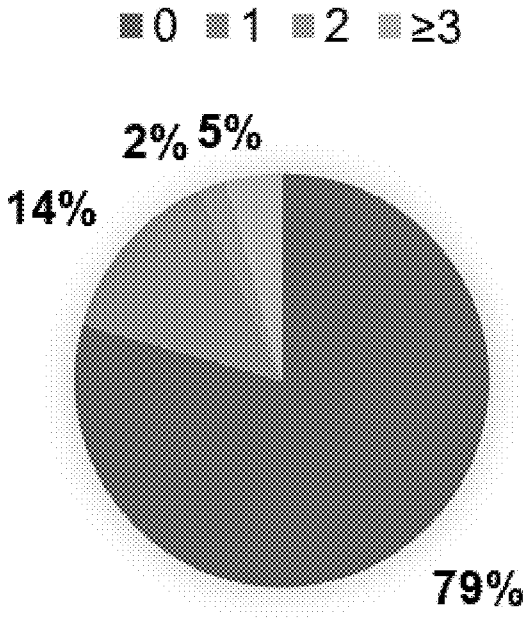
FIG. 8 shows number of CH Mutations detected per person in St Jude Sickle Cell Disease SCCRIP Young Adult Cohort Pilot Sample Set (N=92).
Figure 9:
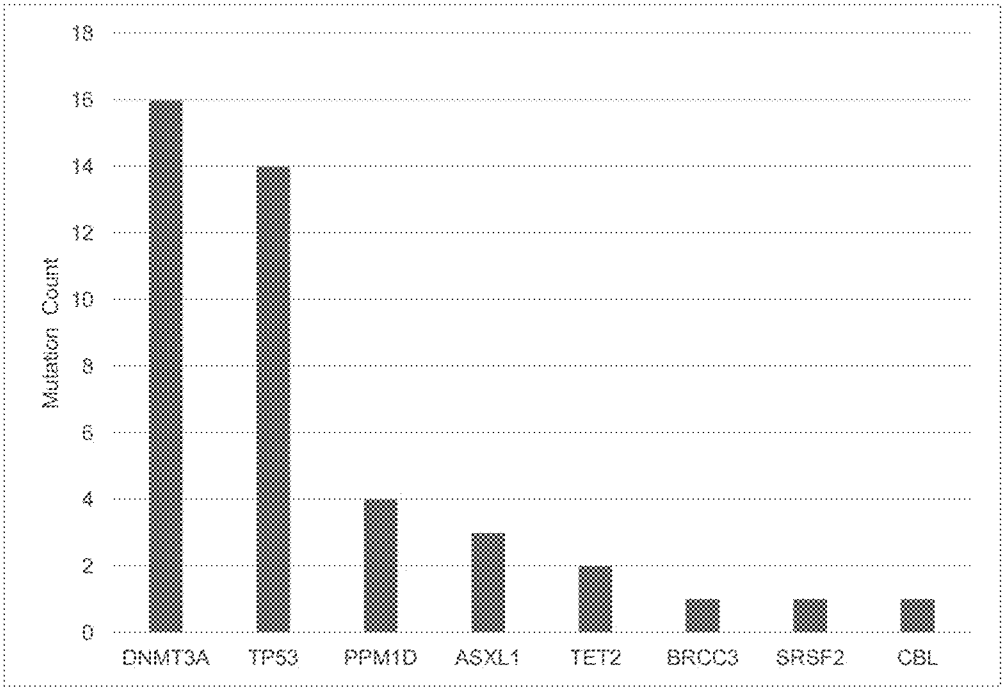
FIG. 9 shows distribution of CH driver genes identified higher than expected proportion of DNA damage repair gene mutations.
Figure 10:
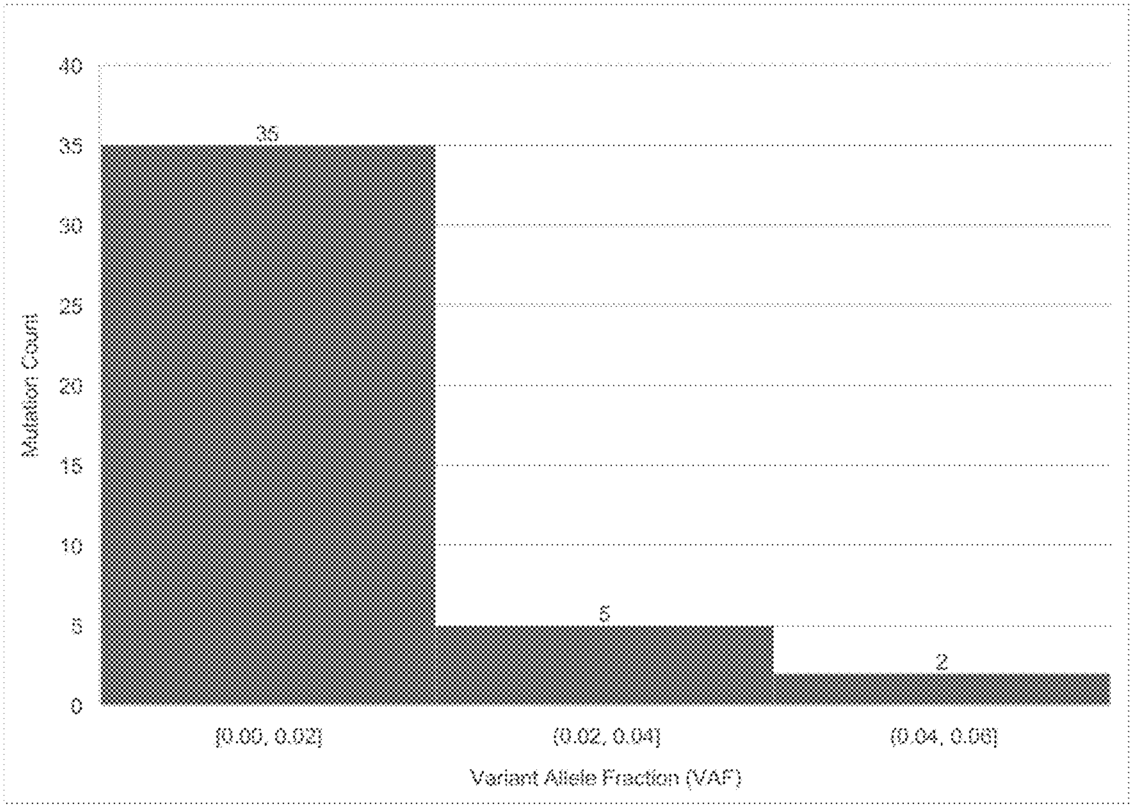
FIG. 10 shows CH Mutation Size distribution. The majority of CH clones detected could not be observed without error corrected sequencing platform (eg VAF<2%).

Example 3: Detection of CH in St Jude Young Adult SCD Samples with Error-Corrected Sequencing 92 young adult samples were assayed from the St Jude Sickle Cell Disease SCCRIP cohort (Median age 24, interquartilie range: 22-31) on the CH assay to demonstrate the utility of the platform. 19 of the 92 samples (21%) had detectable CH with a known driver mutation. 13 of these 19 individuals had a single CH mutation. 6 individuals had more than one CH driver mutation (FIG. 8). Out of the 42 CH driver mutations identified, mutations in DNMT3A were the most common. Interestingly DNA damage repair genes (TP53 and PPM1 D) were the next most common mutations, in contrast to most studies in the general population which typically find that TET2 and ASXL1 mutations are more frequent than TP53 and PPM1 D (FIG. 9). As expected smaller CH clones were more frequently observed than lager clones. Notably 35/42 mutations (83%) fell in a clone size range that could only be detected with error corrected sequencing. (FIG. 10).

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A scalable multiplex method for amplifying a plurality of target DNA regions collectively 1 kb to 100 kb in size in a plurality of samples, wherein each sample of the plurality comprises the plurality of target DNA regions, the method comprising (a) pooling a plurality of barcoded samples containing input DNA;

(b) performing mechanical or enzymatic DNA fragmentation, end repair, and dA-tailing of the input DNA to produce dA-tailed DNA fragments;

(c) ligating universal adapters to the dA-tailed DNA fragments to generate a barcoded DNA library;

(d) normalizing the barcoded DNA library by a method comprising (1) PCR amplifying the DNA library using normalase unique dual index (UDI) primers, (2) enzymatic selection of library fractions using Normalase I, (3) bead purification to purify and select for target DNA region size, (4) pooling the library fractions, and enzymatic normalization of the pooled library fractions with Normalase II to produce a normalized barcoded-DNA library; and (e) hybridization capturing dA-tailed DNA fragments in the plurality of target DNA regions from the normalized barcoded-DNA library by a method comprising:

(1) hybridization capture of the dA-tailed DNA fragments with capture probes, (2) washing and amplification of the captured dA-tailed DNA fragments using primers specific for the universal adapter, and (3) quantification of the amplified DNA.

2. The method of claim 1, further comprising sequencing the amplified DNA.

3. A scalable multiplex method for identifying a subject with increased risk of developing a cardiometabolic disease or a hematological cancer, comprising the steps of:

(a) amplifying and sequencing the plurality of target DNA regions corresponding to the genes DNMT3A, TET2, JAK2, GNAS, GNB, CBL, TP53, PPM1D, SF3B1, SRSF2, PIGA, BCOR, BCORL1, DNMT3A, and ASXL1 from a plurality of DNA samples according to the method of claim 2;

(b) identifying from said sequencing one or more mutations in one or more of the genes, wherein presence of said mutation(s) indicates an increased risk of developing a cardiometabolic disease and/or a hematological cancer.

4. The method according to claim 3, wherein the cardiometabolic disease is atherosclerosis, coronary heart disease (CHD) or ischemic stroke (IS).

5. The method according to claim 3, wherein the hematological cancer is a leukemia, a lymphoma, a myeloma or a blood syndrome.

6. The method according to claim 5, wherein the leukemia is acute myeloid leukemia (AML) or chronic myelogenous leukemia (CML).

7. The method according to claim 5, wherein the blood syndrome is myelodysplastic syndrome (MDS).

8. The method according to claim 3, wherein the plurality of DNA samples is obtained from one or more cells in blood samples comprising hematopoietic stem cells (HSCs), committed myeloid progenitor cells having long term self-renewal capacity, or mature lymphoid cells having long term self-renewal capacity.

9. The method according to claim 3, wherein the subject exhibits one or more risk factors of being a smoker, having a high level of total cholesterol or having high level of high-density lipoprotein (HDL).

10. The method according to claim 3, wherein the one or more mutations are frameshift mutations, nonsense mutations, missense mutations or splice-site variant mutations.

* * * * *

SEQUENCE LISTING

```
Sequence total quantity: 131
SEQ ID NO: 1            moltype = DNA  length = 94
FEATURE                 Location/Qualifiers
source                  1..94
                        mol_type = other DNA
                        organism = synthetic construct
SEQUENCE: 1
tcctccagtc cctaccttgt tggtggtgta gctgtcccag atgataagtt taccatcctg  60
cgaggcactg acgagaagcc tggagggaca gaca                               94

SEQ ID NO: 2            moltype = DNA  length = 137
FEATURE                 Location/Qualifiers
source                  1..137
                        mol_type = other DNA
                        organism = synthetic construct
SEQUENCE: 2
catgcccacg cctacctgga gtctgtgccc cagtgcatgg cgtagatctt ggccaggtgc  60
ccccgcagtg tcctcctcgt gcgcatttgg attcttccca ctgggtcgat gttgtttgtg  120
atcttgaaaa taaaaac                                                  137

SEQ ID NO: 3            moltype = DNA  length = 40
FEATURE                 Location/Qualifiers
source                  1..40
                        mol_type = other DNA
                        organism = synthetic construct
SEQUENCE: 3
tttttaacct agtgcaagat tcttcttcag taccactgcc                         40

SEQ ID NO: 4            moltype = DNA  length = 172
FEATURE                 Location/Qualifiers
source                  1..172
                        mol_type = other DNA
                        organism = synthetic construct
SEQUENCE: 4
ttgcccccat gtcccttaca cacacgcaaa atactccttc agcggagcga agaggtggcg  60
gatgactggc acgctccatg accggcccag cagtctctgc ctcgccaagc ggctcatgtt  120
ggagacgtca gtatagtgga ctgggaaacc aaataccctg ggggagaaaa gg           172

SEQ ID NO: 5            moltype = DNA  length = 149
FEATURE                 Location/Qualifiers
source                  1..149
                        mol_type = other DNA
                        organism = synthetic construct
SEQUENCE: 5
gcacaacccg ggtacctttc catttcagtg caccataaga tgtcctcttt ctcattcatg  60
aagacaggaa aatgctggtc tttgccctgc tttatggagt ttgacctcgt agtaatggtc  120
```

```
ctcactttgc tgaactagat gaagaggag                                149

SEQ ID NO: 6           moltype = DNA  length = 100
FEATURE                Location/Qualifiers
source                 1..100
                       mol_type = other DNA
                       organism = synthetic construct
SEQUENCE: 6
gacgctggag ctgaccttgg ctatcctgcc atgctccaga cactcctgca gctccagctt  60
atcattcaca gtggatgcca acggcctagg aggcagaaga                      100

SEQ ID NO: 7           moltype = DNA  length = 116
FEATURE                Location/Qualifiers
source                 1..116
                       mol_type = other DNA
                       organism = synthetic construct
SEQUENCE: 7
ggagctttca ccaacctgtt cataccggga aggttacccc agaagtagcg ggccctgtgt  60
gcagctgaca cttctttggc atcaatcatc acagggttgg actacaaaac aggaga      116

SEQ ID NO: 8           moltype = DNA  length = 54
FEATURE                Location/Qualifiers
source                 1..54
                       mol_type = other DNA
                       organism = synthetic construct
SEQUENCE: 8
gtggccacta gcccactagt acaggtggct attttgtacc taaaatgagg ccaa        54

SEQ ID NO: 9           moltype = DNA  length = 179
FEATURE                Location/Qualifiers
source                 1..179
                       mol_type = other DNA
                       organism = synthetic construct
SEQUENCE: 9
ggttgctggc tatacctcga gaaatcgcga gatgtccctc ttgtcactaa cgcccatggc  60
caccacattc tcaaagagcc agaagaaggg gcgatcatct ccctccttgg gccgcgcatc  120
atgcaggagg cggtagaact caaagaagag ccggccagtg ccctctgaga ggtcggaag   179

SEQ ID NO: 10          moltype = DNA  length = 121
FEATURE                Location/Qualifiers
source                 1..121
                       mol_type = other DNA
                       organism = synthetic construct
SEQUENCE: 10
caggatggta cctaccgtag aggcccttgc gagcagggtt gacgatggag aggtcattgc  60
agggactgcc cccaatcacc agatcgaatg ggccccactc ctggatctgg gaggataaag  120
g                                                                  121

SEQ ID NO: 11          moltype = DNA  length = 176
FEATURE                Location/Qualifiers
source                 1..176
                       mol_type = other DNA
                       organism = synthetic construct
SEQUENCE: 11
acagcatgga catacatgct tctgtgtgac gctgcggacg tccccgacgt acatgatctt  60
cccctggtgc cgcaccatgc ccaccgtgat ggagtcctca cacacctccg aggcaatgta  120
gcggtccacc tgaatgccca agtccttcag caccaggagc cctgcaccag ccagca      176

SEQ ID NO: 12          moltype = DNA  length = 115
FEATURE                Location/Qualifiers
source                 1..115
                       mol_type = other DNA
                       organism = synthetic construct
SEQUENCE: 12
gcctgcaccc ctcacctgta gcgattccat caaagagaga cagcacccgg atgggcttcc  60
tcttctcagc tgggacaggt gggtaaacct ttggagggtc ctaagcagtg agcac       115

SEQ ID NO: 13          moltype = DNA  length = 214
FEATURE                Location/Qualifiers
source                 1..214
                       mol_type = other DNA
                       organism = synthetic construct
SEQUENCE: 13
aggcccagca ctcacaaatt cctggtcgtg gttattagcg aagaacatct ggagccggga  60
gggccagtcc tctcgccgcc gcagcagccc gtaggtaccc ttgtgcccgc acatgtagca  120
gttccagggg tcttccttaa tggctgcctg ggcagccccc ggccccacca agaggtccac  180
acactccacg caaaagcacc tggaaggaga ccca                              214

SEQ ID NO: 14          moltype = DNA  length = 143
```

```
FEATURE                 Location/Qualifiers
source                  1..143
                        mol_type = other DNA
                        organism = synthetic construct
SEQUENCE: 14
ccacaacagc ctcacctgca gcagttgttg tttccgcaca tgagcacctc acggccccca  60
cagcagatgg tgcagtagga ctggtagccg tcgtcgtcgt actggtacgc acactccaga  120
aagcagttct agacagcagc ggg                                          143

SEQ ID NO: 15           moltype = DNA  length = 110
FEATURE                 Location/Qualifiers
source                  1..110
                        mol_type = other DNA
                        organism = synthetic construct
SEQUENCE: 15
tgggtgtgct cctaccttgc agttttggca cattcctcca acgaagaggg ggtgttccag  60
ggtaacattg aggctcccac aggagatgca gatgtctgga aagcagaggg             110

SEQ ID NO: 16           moltype = DNA  length = 75
FEATURE                 Location/Qualifiers
source                  1..75
                        mol_type = other DNA
                        organism = synthetic construct
SEQUENCE: 16
aggcaacaaa cttaccctca atgttccggc acttctgccg cacctcgtac accagccgct  60
ctgcaagggg aggag                                                   75

SEQ ID NO: 17           moltype = DNA  length = 180
FEATURE                 Location/Qualifiers
source                  1..180
                        mol_type = other DNA
                        organism = synthetic construct
SEQUENCE: 17
aagcaggcca actacctctt gtgcgctcat caataatctc cttgaccttg ggcttctccg  60
ctgtgctctt ccggggcttt ttggctggtg gaggtggtgc gtaggcagct gcctcaggtt  120
ccacccacat gtccgtgtac acttctttgt agggattctt ctcttctgga ggaggaaagc  180

SEQ ID NO: 18           moltype = DNA  length = 187
FEATURE                 Location/Qualifiers
source                  1..187
                        mol_type = other DNA
                        organism = synthetic construct
SEQUENCE: 18
ggtgccctca tttaccttct ggtggctcca ggcccttagg gccagaaggc tggaagcccc  60
ccagggccca ttcaatcatg ggcttgttct gcacctccac ggccttggca gtgtcactct  120
catcgctgtc gtggcacacc gggaacagct tccccgcgcg gctgctggcc acctggaggg  180
tgacacg                                                            187

SEQ ID NO: 19           moltype = DNA  length = 138
FEATURE                 Location/Qualifiers
source                  1..138
                        mol_type = other DNA
                        organism = synthetic construct
SEQUENCE: 19
agcagggaca ctcacctgca ggacctcgta gatggctttg cggtacatgg gctgcttgtt  60
gtacgtggcc tggtggaacg cactgcaaaa cgagctcagc ggcatcagct tctcaacaca  120
cacctggggg gacaagcc                                                138

SEQ ID NO: 20           moltype = DNA  length = 189
FEATURE                 Location/Qualifiers
source                  1..189
                        mol_type = other DNA
                        organism = synthetic construct
SEQUENCE: 20
aaccccacaa cttaccactg agaatttgcc gtctccgaac cacatgaccc agcgggtgcc  60
ttcagctgct cggctccggc ccgtcatcca ccaagacaca atgcggcctg gccaccagga  120
gaagccccgc agtttccccc acaccagctc cccaatgcca aagccccggc cgtcctggag  180
ccccaagga                                                          189

SEQ ID NO: 21           moltype = DNA  length = 246
FEATURE                 Location/Qualifiers
source                  1..246
                        mol_type = other DNA
                        organism = synthetic construct
SEQUENCE: 21
gaagaagccg ctcacctcgt actctggctc gtcatcgcct gctttggtgg cattcttgtc  60
cccagcatcg gaccccacgg gctcaggcgt ggtagccaca gtgggggatg cggggtcagt  120
gggctgctgc acagcaggag ggctggcctc ctccaccttc tgagactccc cgggcccctg  180
gttttcttcc acagcattca ttcctgcaat gaccttggct ttcttctcag cctggggaaa  240
```

```
caaaaa                                                            246

SEQ ID NO: 22          moltype = DNA  length = 98
FEATURE                Location/Qualifiers
source                 1..98
                       mol_type = other DNA
                       organism = synthetic construct
SEQUENCE: 22
cctccatcct ttcaccgtat cacactcgtc tttcaggcta cgatccacgc gcccattcct  60
tctcacaacc cgctccagga tccctacaaa ggagaatg                          98

SEQ ID NO: 23          moltype = DNA  length = 213
FEATURE                Location/Qualifiers
source                 1..213
                       mol_type = other DNA
                       organism = synthetic construct
SEQUENCE: 23
ccagcctgca gttaccactg cccgggctcc cggccggctg ctcttcctgt cccccgaggg  60
cgccaggtgc cactggagcc ctcgaggagt ggggccttgg ggctcgtggg caggaaggcg  120
gcgggccagc actaagtcag catctccaga actcgggcca ggccgggacg ccgcggctgc  180
tgcgggccgg ggaggcatac ttcactcttt tca                               213

SEQ ID NO: 24          moltype = DNA  length = 34
FEATURE                Location/Qualifiers
source                 1..34
                       mol_type = other DNA
                       organism = synthetic construct
SEQUENCE: 24
cgtccaggaa cctacccata aggccaggtg cagc                              34

SEQ ID NO: 25          moltype = DNA  length = 177
FEATURE                Location/Qualifiers
source                 1..177
                       mol_type = other DNA
                       organism = synthetic construct
SEQUENCE: 25
cagaaggcgc ctcacctccc ttttccagcg tgccagccac tcgtcccgct tgcgcttgct  60
gatgtagtag gggtcccccg cctggaaggt gagcctcggc atgggccgct gacggaggct  120
ggactcccag cccaagccac cccgcagccg gccccgggag ccctaggaca gagagac     177

SEQ ID NO: 26          moltype = DNA  length = 74
FEATURE                Location/Qualifiers
source                 1..74
                       mol_type = other DNA
                       organism = synthetic construct
SEQUENCE: 26
gggtggaaca cttgcctcca ttttcatgga ttcgatgttg gtctccttct gttctttgcc  60
tgtggagagg gaag                                                    74

SEQ ID NO: 27          moltype = DNA  length = 354
FEATURE                Location/Qualifiers
source                 1..354
                       mol_type = other DNA
                       organism = synthetic construct
SEQUENCE: 27
ccaagtccct gactctcagg gtatgctggt gggcccagaa gaggctgccc ctggtgctga  60
ggactcaccc gcttctgcag gggctcctcg gccctccttg ggggtgcagc agccattttc  120
cactgctctt gaggcttcag gcagggtctc agctgcaccc tctccctctg ctggggcccc  180
gcccttctgc cccccagcag ggctcccctc ctctggctgg ggctcactcc gcttctccaa  240
gtccccattg ggtaatagct ctgaggcgcc tgagtcctgg gccatggatg gggacttgga  300
gatcaccgca gggtcctttg gcgtgtcacc gctttccacc tgcaaatgta agaa        354

SEQ ID NO: 28          moltype = DNA  length = 102
FEATURE                Location/Qualifiers
source                 1..102
                       mol_type = other DNA
                       organism = synthetic construct
SEQUENCE: 28
gagcccgctg ctcacctttc ggtcctcctc ccgctccgca gcagagctgc tggtgtcccc  60
ggggccgctg gagggcatgg cgggcatctg ggcgccggga gg                     102

SEQ ID NO: 29          moltype = DNA  length = 142
FEATURE                Location/Qualifiers
source                 1..142
                       mol_type = other DNA
                       organism = synthetic construct
SEQUENCE: 29
cagcaaattc catacctatg acatttacaa tggccttcag tgctccaaga atgctgccca  60
atacttcagg gtactcttca cccaaatact catacaatac aacacccaag tgtcccatca  120
```

```
atttttccta taataaaaca aa                                          142

SEQ ID NO: 30          moltype = DNA  length = 213
FEATURE                Location/Qualifiers
source                 1..213
                       mol_type = other DNA
                       organism = synthetic construct
SEQUENCE: 30
gatgcaaaag tttacctctt gacaagtctt catgacaaca gcagttcgag aaatcaagtc  60
agctgcctgt tgcctaactt tagcagattt gttatttaaa cgccacaaaa ctgtaccaca  120
gatctgaggc aagtatggtt tgactcgttt gccaagagca ttaaccactg tgccaaagcc  180
gttcaacatt actgagtcct aaaaaataaa ttt                              213

SEQ ID NO: 31          moltype = DNA  length = 252
FEATURE                Location/Qualifiers
source                 1..252
                       mol_type = other DNA
                       organism = synthetic construct
SEQUENCE: 31
aatagttttc attacctctg tagtctgttc ttggaaagca taaagaatac catcaatcag  60
ttgttcttca agtttatgat caatatctgc tgctcccaaa ttacccataa ttttctcaat  120
tgtctccatc accattttc tgtactgttc ggcttcatct ttcagatcat ccacaatcct  180
ggatataatt tctgctgcac ctactttgtt tgccaactcc acagtagtat caactaacta  240
aaaagaacag aa                                                     252

SEQ ID NO: 32          moltype = DNA  length = 156
FEATURE                Location/Qualifiers
source                 1..156
                       mol_type = other DNA
                       organism = synthetic construct
SEQUENCE: 32
acaataaaag cttacctgtc ggtaatttct tctatccaaa gccatcctgt gctgccagaa  60
gtgtttaaaa aagggaggaa gaatctctgt tttaatgtag tttgcttcta caccatctgt  120
cccacaacac tgttttacca cctaaaaggt taagaa                           156

SEQ ID NO: 33          moltype = DNA  length = 177
FEATURE                Location/Qualifiers
source                 1..177
                       mol_type = other DNA
                       organism = synthetic construct
SEQUENCE: 33
atctggaata attaccttca gcacaatttt tttcatttcc tcatcaggag actggaattc  60
tcgaataagg attaacatca cttctctagt atagtagttg gcatattctg catccataag  120
aggaataaga tacccaatag ccttcaagaa agcagccaaa ccctattttt aaataaa    177

SEQ ID NO: 34          moltype = DNA  length = 176
FEATURE                Location/Qualifiers
source                 1..176
                       mol_type = other DNA
                       organism = synthetic construct
SEQUENCE: 34
aattggtgga tttacctttc ctctgtgttg gcggataccc ttccataaag gctttaacac  60
agaatcaaaa gattcgatac cataaggagt tgctgcttca gccaaggcag caatggccaa  120
agcactgatg gtccgaactt tctgctgctc atccacaaga cctacaaaac caaaca     176

SEQ ID NO: 35          moltype = DNA  length = 301
FEATURE                Location/Qualifiers
source                 1..301
                       mol_type = other DNA
                       organism = synthetic construct
SEQUENCE: 35
tacattacaa cttaccatgt tcaatgattt caactaaact tctaagatgt ggcaagatgg  60
cacagcccat aagaatagct atctgttgta caatcttaat accagtgtgt ctcgcttgcc  120
aggacttctt gcttttgcac acagctttta agaagggcaa taaagaagga atgcccaggg  180
cagaggctac aacagcaaaa gctctagctg ttgtgttacg gacatactca tccatgttat  240
ctatatcagg tctcatggta gagatcatag tagccagacc agcagcctaa aatgtaaaca  300
a                                                                 301

SEQ ID NO: 36          moltype = DNA  length = 117
FEATURE                Location/Qualifiers
source                 1..117
                       mol_type = other DNA
                       organism = synthetic construct
SEQUENCE: 36
attaaatgta aataccttg ccaaattaga aatgatctct cggccttcca ctctagcata  60
gtaatcttca tcaatcaata gcggttcaat gaccacgagg atctgaaaaa gagaaaa    117

SEQ ID NO: 37          moltype = DNA  length = 210
FEATURE                Location/Qualifiers
```

```
source                1..210
                      mol_type = other DNA
                      organism = synthetic construct
SEQUENCE: 37
ttaaggagaa caaaccttat gcacatatgg acgaactaag tcatcaagtt tgtacagtat  60
cctatcaata actttcacaa gtaaatgacg ctcttgatcc tcaagtgtag gagacatcag  120
cagaggaaga atctgattaa acaaaggacc agctccaaat tcacgagctt tatcagtaat  180
ctgacgcaat gcagcctggg aaaaagagca                                   210

SEQ ID NO: 38         moltype = DNA  length = 132
FEATURE               Location/Qualifiers
source                1..132
                      mol_type = other DNA
                      organism = synthetic construct
SEQUENCE: 38
caaactggga cttacctttc tcattggtgg tgttccattc ttaattttta aaagcaactt  60
cattattttt ctctcttttt gctcttctgg actaagtgtt gattcatcaa catcaaccta  120
tagtaaaaag aa                                                       132

SEQ ID NO: 39         moltype = DNA  length = 228
FEATURE               Location/Qualifiers
source                1..228
                      mol_type = other DNA
                      organism = synthetic construct
SEQUENCE: 39
gctagtatca cttaccaata gtttatcaaa gtattgaata tcatcaggtt ttaaaaatgg  60
aagatttcca gatggctggt cattaacact tttcatagtt cgatcttcag tttgcatgtg  120
gaaaccagtc ataccaccca aaggtgttgg agtagctgtc agctttcgag ctggagttcg  180
aataggaaca taaccagctg gaggaggaag tacctaataa aagttata               228

SEQ ID NO: 40         moltype = DNA  length = 152
FEATURE               Location/Qualifiers
source                1..152
                      mol_type = other DNA
                      organism = synthetic construct
SEQUENCE: 40
aatttgatgt actaccttat atccttctgg gaacatagca tctaattcct catcagaaag  60
tgggcgattt ctctcatcaa tttctctttc ccaccgccaa gcctgaagct gttcaggagt  120
catactcatt atgtgaccta ccaagaaaag ca                                 152

SEQ ID NO: 41         moltype = DNA  length = 243
FEATURE               Location/Qualifiers
source                1..243
                      mol_type = other DNA
                      organism = synthetic construct
SEQUENCE: 41
atgagacagt tctacctgga gtaggggtag ccatgttcat ggctggtgtg ccaattggtg  60
tctttccagg ggtcagaact ggagtgcttc cacccatctg actagctggt gtttcatccc  120
accgtgattt tcttttactg gctccaggag tcggtgtttc accaatagaa tctccacctc  180
gatctgttcg aggagtctca gcccatccac ttccatgccc aggagtatct ttaaaaagaa  240
aga                                                                 243

SEQ ID NO: 42         moltype = DNA  length = 268
FEATURE               Location/Qualifiers
source                1..268
                      mol_type = other DNA
                      organism = synthetic construct
SEQUENCE: 42
ctccactaga agtacctctc tctgttttgg gggtttcatc ccatctgttt ttacgagcac  60
tggaagttgc gcctccatgg cctggtgtcg catggcctgg tgtatcacct cgtccaggag  120
tagcagctcc cgctggtgtg tggctaggtg taggatccca tatttttgag cctggggttg  180
ctccaggagt ctcgcttccc tttgcacgac ctggtgtctc atcccatctt aaggaaggag  240
tatgcccagg ggtcttaaaa aagcaaaa                                     268

SEQ ID NO: 43         moltype = DNA  length = 201
FEATURE               Location/Qualifiers
source                1..201
                      mol_type = other DNA
                      organism = synthetic construct
SEQUENCE: 43
acaaaaagaa attacctctg cctgatccca acttgatagt tttttgggag tggcaccagg  60
agtctgatca gctgtttgat cccaacgccg ttttcgtttt gatggaggct gggacgctgc  120
tgctccattg acgactttta gttctccagc tttagctttt tctgctagct gttgcctaat  180
ttctcgctga aaaaaacagt g                                             201

SEQ ID NO: 44         moltype = DNA  length = 83
FEATURE               Location/Qualifiers
source                1..83
                      mol_type = other DNA
```

```
                        organism = synthetic construct
SEQUENCE: 44
ttattgccaa catgacttac ttgatcccca taagcatgac gacctatgat gataggtttt  60
acccatccac tcacaagccg ggg                                          83

SEQ ID NO: 45           moltype = DNA  length = 127
FEATURE                 Location/Qualifiers
source                  1..127
                        mol_type = other DNA
                        organism = synthetic construct
SEQUENCE: 45
tccattgtag agcaaatcca tccccacacc ctgttcactc ctttgctgat tggtttcgta  60
atcgtagctg gcatgatgtg cattattgtg atgattctga cctacaaata tttacaggta  120
accattt                                                            127

SEQ ID NO: 46           moltype = DNA  length = 147
FEATURE                 Location/Qualifiers
source                  1..147
                        mol_type = other DNA
                        organism = synthetic construct
SEQUENCE: 46
ctccccacag aaacccatgt atgaagtaca gtggaaggtt gttgaggaga taaatggaaa  60
caattatgtt tacatagacc caacacaact tccttatgat cacaaatggg agtttcccag  120
aaacaggctg agttttggtc agtatga                                      147

SEQ ID NO: 47           moltype = DNA  length = 125
FEATURE                 Location/Qualifiers
source                  1..125
                        mol_type = other DNA
                        organism = synthetic construct
SEQUENCE: 47
cttcctacag ggaaaaccct gggtgctgga gctttcggga aggttgttga ggcaactgct  60
tatggcttaa ttaagtcaga tgcggccatg actgtcgctg taaagatgct caagcgtaag  120
ttcct                                                              125

SEQ ID NO: 48           moltype = DNA  length = 131
FEATURE                 Location/Qualifiers
source                  1..131
                        mol_type = other DNA
                        organism = synthetic construct
SEQUENCE: 48
ccaattttag cgagtgccca tttgacagaa cgggaagccc tcatgtctga actcaaagtc  60
ctgagttacc ttggtaatca catgaatatt gtgaatctac ttggagcctg caccattgga  120
ggtaaagccg t                                                       131

SEQ ID NO: 49           moltype = DNA  length = 171
FEATURE                 Location/Qualifiers
source                  1..171
                        mol_type = other DNA
                        organism = synthetic construct
SEQUENCE: 49
gtgcttttag ggcccaccct ggtcattaca gaatattgtt gctatggtga tcttttgaat  60
tttttgagaa gaaaacgtga ttcatttatt tgttcaaagc aggaagatca tgcagaagct  120
gcactttata agaatcttct gcattcaaag gagtcttcct ggtaagactg a           171

SEQ ID NO: 50           moltype = DNA  length = 112
FEATURE                 Location/Qualifiers
source                  1..112
                        mol_type = other DNA
                        organism = synthetic construct
SEQUENCE: 50
tctctcccag cagcgatagt actaatgagt acatggacat gaaacctgga gtttcttatg  60
ttgtcccaac caaggccgac aaaaggagat ctgtgagaat aggtgagtac ct          112

SEQ ID NO: 51           moltype = DNA  length = 148
FEATURE                 Location/Qualifiers
source                  1..148
                        mol_type = other DNA
                        organism = synthetic construct
SEQUENCE: 51
ttcctcacag gctcatacat agaaagagat gtgactcccg ccatcatgga ggatgacgag  60
ttggccctag acttagaaga cttgctgagc ttttcttacc aggtggcaaa gggcatggct  120
ttcctcgcct ccaagaatgt aagtggga                                     148

SEQ ID NO: 52           moltype = DNA  length = 143
FEATURE                 Location/Qualifiers
source                  1..143
                        mol_type = other DNA
                        organism = synthetic construct
```

```
SEQUENCE: 52
aacctaatag tgtattcaca gagacttggc agccagaaat atcctcctta ctcatggtcg  60
gatcacaaag atttgtgatt ttggtctagc cagagacatc aagaatgatt ctaattatgt  120
ggttaaagga aacgtgagta ccc                                          143

SEQ ID NO: 53          moltype = DNA  length = 132
FEATURE                Location/Qualifiers
source                 1..132
                       mol_type = other DNA
                       organism = synthetic construct
SEQUENCE: 53
tctattacag gctcgactac ctgtgaagtg gatggcacct gaaagcattt tcaactgtgt  60
atacacgttt gaaagtgacg tctggtccta tgggattttt ctttgggagc tgttctcttt  120
aggtaaaatg at                                                      132

SEQ ID NO: 54          moltype = DNA  length = 3574
FEATURE                Location/Qualifiers
source                 1..3574
                       mol_type = other DNA
                       organism = synthetic construct
SEQUENCE: 54
ttccatgctc tttagaattc aactagaggg cagccttgtg gatggccccg aagcaagcct  60
gatggaacag gatagaacca accatgttga gggcaacaga ctaagtccat tcctgatacc  120
atcacctccc atttgccaga cagaacctct ggctacaaag ctccagaatg gaagcccact  180
gcctgagaga gctcatccag aagtaaatgg agacaccaag tggcactctt tcaaaagtta  240
ttatggaata ccctgtatga agggaagcca gaatagtcgt gtgagtcctg actttacaca  300
agaaagtaga gggtattcca agtgtttgca aaatggagga ataaaacgca cagttagtga  360
accttctctc tctgggctcc ttcagatcaa gaaattgaaa caagaccaaa aggctaatgg  420
agaaagacgt aacttcgggg taagccaaga aagaaatcca ggtgaaagca gtcaaccaaa  480
tgtctccgat ttgagtgata agaaagaatc tgtgagttct gtagcccaag aaaatgcagt  540
taaagatttc accagttttt caacacataa ctgcagtggg cctgaaaatc cagagcttca  600
gattctgaat gagcaggagg ggaaaagtgc taattaccat gacaagaaca ttgtattact  660
taaaaacaag gcagtgctaa tgcctaatgg tgctacagtt tctgcctctt ccgtggaaca  720
cacacatggt gaactcctgg aaaaaacact gtctcaatat tatccagatt gtgtttccat  780
tgcggtgcag aaaaccacat ctcacataaa tgccattaac agtcaggcta ctaatgagtt  840
gtcctgtgag atcactcacc catcgcatac ctcagggcag atcaattccg cacagacctc  900
taactctgag ctgcctccaa agccagctgc agtggtgagt gaggcctgtg atgctgatga  960
tgctgataat gccagtaaac tagctgcaat gctaaatacc tgttcctttc agaaaccaga  1020
acaactacaa caacaaaaat cagtttttga gatatgccca tctcctgcag aaaataacat  1080
ccagggaacc acaaagctag cgtctggtga agaattctgt tcaggttcca gcagcaattt  1140
gcaagctcct ggtggcagct ctgaacggta tttaaaacaa aatgaaatga atggtgctta  1200
cttcaagcaa agctcagtgt tcactaagga ttcctttttct gccactacca caccaccacc  1260
accatcacaa ttgcttcttt ctccccctcc tcctcttcca caggttcctc agcttccttc  1320
agaaggaaaa agcactctga atggtggagt tttagaagaa caccaccact accccaacca  1380
aagtaacaca acacttttaa gggaagtgaa aatagagggt aaacctgagg caccaccttc  1440
ccagagtcct aatccatcta cacatgtatg cagcccttct ccgatgcttt ctgaaaggcc  1500
tcagaataat tgtgtgaaca ggaatgacat acagactgca gggacaatga ctgttccatt  1560
gtgttctgag aaaacaagac caatgtcaga acacctcaag cataacccac caatttttgg  1620
tagcagtgga gagctacagg acaactgcca gcagttgatg agaaacaaag agcaagagat  1680
tctgaagggt cgagacaagg agcaaacacg agatcttgtg cccccaacac agcactatct  1740
gaaaccagga tggattgaat tgaaggcccc tcgttttcac caagcggaat cccatctaaa  1800
acgtaatgag gcatcactgc catcaattct tcagtatcaa cccaatctct ccaatcaaat  1860
gacctccaaa caatacactg gaaattccaa catgcctggg gggctcccaa ggcaagctta  1920
cacccagaaa acaacacagc tggagcacaa gtcacaaatg taccaagttg aaatgaatca  1980
agggcagtcc caaggtacag tggaccaaca tctccagttc caaaaaccct cacaccaggt  2040
gcacttctcc aaaacagacc atttaccaaa agctcatgtg cagtcactgt gtggcactag  2100
atttcatttt caacaaagag cagattccca aactgaaaaa cttatgtccc cagtgttgaa  2160
acagcacttg aatcaacagg cttcagagac tgagccattt tcaaactcac accttttgca  2220
acataagcct cataaacagg cagcacaaac acaaccatcc cagagttcac atctccctca  2280
aaaccagcaa cagcagcaaa aattacaaat aaagaataaa gaggaaatac tccagacttt  2340
tcctcacccc caaagcaaca atgatcagca aagagaagga tcattctttg gccagactaa  2400
agtggaagaa tgttttcatg gtgaaaatca gtattcaaaa tcaagcgagt tcgagactca  2460
taatgtccaa atgggactgg aggaagtaca gaatataaat cgtagaaatt ccccttatag  2520
tcagaccatg aaatcaagtg catgcaaaat acaggtttct tgttcaaaca atacacacct  2580
agtttcagag aataaagaac agactacaca tcctgaactt tttgcaggaa acaagaccca  2640
aaacttgcat cacatgcaat attttccaaa taatgtgatc ccaaagcaag atcttcttca  2700
caggtgcttt caagaacagg agcagaagtc acaacaagct tcagttctac agggatataa  2760
aaatagaaac caagatatgt ctggtcaaca agctgcgcaa cttgctcagc aaaggtactt  2820
gatacataac catgcaaatg tttttcctgt gcctgaccag ggaggaagtc acactcagac  2880
ccctcccccag aaggacactc aaaagcatgc tgctctaagg tggcatctct tacagaagca  2940
agaacagcag caaacacagc aaccccaaac tgagtcttgc catagtcaga tgcacaggcc  3000
aattaaggtg gaacctggat gcaagccaca tgcctgtatg cacacagcac caccagaaaa  3060
caaaacatgg aaaaaggtaa ctaagcaaga gaatccacct gcaagctgtg ataatgtgca  3120
gcaaaagagc atcattgaga ccatggagca gcatctgaag cagtttcacg ccaagtcgtt  3180
atttgaccat aaggctctta ctctcaaatc acagaagcaa gtaaaagttg aaatgtcagg  3240
gccagtcaca gttttgacta gacaaaccac tgctgcagaa cttgatagcc acaccccagc  3300
tttagagcag caaacaactt cttcagaaaa gacaccaacc aaaagaacag ctgcttctgt  3360
tctcaataat tttatagagt caccttccaa attactagat actcctataa aaaatttatt  3420
ggatacacct gtcaagactc aatatgattt cccatcttgc agatgtgtag gtaagtgcca  3480
```

```
gaaatgtact gagacacatg gcgtttatcc agaattagca aatttatctt cagatatggg  3540
attttccttc tttttttaaa tcttgagtct ggca                              3574

SEQ ID NO: 55          moltype = DNA  length = 125
FEATURE                Location/Qualifiers
source                 1..125
                       mol_type = other DNA
                       organism = synthetic construct
SEQUENCE: 55
ctattatctc aacagagcaa attattgaaa aagatgaagg tcctttttat acccatctag  60
gagcaggtcc taatgtggca gctattagag aaatcatgga agaaaggtaa ttaacgcaaa  120
ggcac                                                              125

SEQ ID NO: 56          moltype = DNA  length = 124
FEATURE                Location/Qualifiers
source                 1..124
                       mol_type = other DNA
                       organism = synthetic construct
SEQUENCE: 56
gtgggtttct ttaaggtttg gacagaaggg taaagctatt aggattgaaa gagtcatcta  60
tactggtaaa gaaggcaaaa gttctcaggg atgtcctatt gctaagtggg taagtgtgac  120
ttga                                                               124

SEQ ID NO: 57          moltype = DNA  length = 239
FEATURE                Location/Qualifiers
source                 1..239
                       mol_type = other DNA
                       organism = synthetic construct
SEQUENCE: 57
tggtgatcca cgcaggtggt tcgcagaagc agcagtgaag agaagctact gtgtttggtg  60
cgggagcgag ctggccacac ctgtgaggct gcagtgattg tgattctcat cctggtgtgg  120
gaaggaatcc cgctgtctct ggctgacaaa ctctactcgg agcttaccga gacgctgagg  180
aaatacggca cgctcaccaa tcgccggtgt gccttgaatg aagagtaagt gaagcccag   239

SEQ ID NO: 58          moltype = DNA  length = 181
FEATURE                Location/Qualifiers
source                 1..181
                       mol_type = other DNA
                       organism = synthetic construct
SEQUENCE: 58
cttttgattt ttcaggagaa cttgcgcctg tcaggggctg gatccagaaa cctgtggtgc  60
ctccttctct tttggttgtt catggagcat gtactacaat ggatgtaagt ttgccagaag  120
caagatccca aggaagttta agctgcttgg ggatgaccca aaagaggttt gtttacttcc  180
t                                                                  181

SEQ ID NO: 59          moltype = DNA  length = 120
FEATURE                Location/Qualifiers
source                 1..120
                       mol_type = other DNA
                       organism = synthetic construct
SEQUENCE: 59
attcacttta tacaggaaga gaaactggag tctcatttgc aaaacctgtc cactcttatg  60
gcaccaacat ataagaaact tgcacctgat gcatataata atcaggtaag tttaaataat  120

SEQ ID NO: 60          moltype = DNA  length = 168
FEATURE                Location/Qualifiers
source                 1..168
                       mol_type = other DNA
                       organism = synthetic construct
SEQUENCE: 60
acttttattt ttcagattga atatgaacac agagcaccag agtgccgtct gggtctgaag  60
gaaggccgtc cattctcagg ggtcactgca tgtttggact tctgtgctca tgcccacaga  120
gacttgcaca acatgcagaa tggcagcaca ttggtaagtt gggctgag               168

SEQ ID NO: 61          moltype = DNA  length = 385
FEATURE                Location/Qualifiers
source                 1..385
                       mol_type = other DNA
                       organism = synthetic construct
SEQUENCE: 61
ttacttccct accaggtatg cactctcact agagaagaca atcgagaatt tggaggaaaa  60
cctgaggatg agcagcttca cgttctgcct ttatacaaag tctctgacgt ggatgagttt  120
gggagtgtgg aagctcagga ggagaaaaaa cggagtggtg ccattcaggt actgagttct  180
tttcggcgaa aagtcaggat gttagcagag ccagtcaaga cttgccgaca aaggaaacta  240
gaagccaaga aagctgcagc tgaaaagctt tcctccctgg agaacagctc aaataaaaat  300
gaaaaggaaa agtcagcccc atcacgtaca aaacaaactg aaaacgcaag ccaggctaaa  360
cagttggcag gtaaatttaa tgtaa                                        385

SEQ ID NO: 62          moltype = DNA  length = 1502
```

```
FEATURE                Location/Qualifiers
source                 1..1502
                       mol_type = other DNA
                       organism = synthetic construct
SEQUENCE: 62
ttaccctgtc cacagaactt ttgcgacttt caggaccagt catgcagcag tcccagcagc  60
cccagcctct acagaagcag ccaccacagc cccagcagca gcagagaccc cagcagcagc  120
agccacatca ccctcagaca gagtctgtca actcttattc tgcttctgga tccaccaatc  180
catacatgag acggcccaat ccagttagtc cttatccaaa ctcttcacac acttcagata  240
tctatggaag caccagccct atgaacttct attccacctc atctcaagct gcaggttcat  300
atttgaattc ttctaatccc atgaaccctt accctgggct tttgaatcag aatacccaat  360
atccatcata tcaatgcaat ggaaacctat cagtggacaa ctgctcccca tatctgggtt  420
cctattctcc ccagtctcag ccgatggatc tgtataggta tccaagccaa gaccctctgt  480
ctaagctcag tctaccaccc atccatacac tttaccagcc aaggtttgga aatagccaga  540
gttttacatc taaatactta ggttatggaa accaaaatat gcagggagat ggtttcagca  600
gttgtaccat tagaccaaat gtacatcatg tagggaaatt gcctccttat cccactcatg  660
agatggatgg ccacttcatg ggagccacct ctagattacc acccaatctg agcaatccaa  720
acatggacta taaaaatggt gaacatcatt caccttctca cataatccat aactacagtg  780
cagctccggg catgttcaac agctctcttc atgccctgca tctccaaaac aaggagaatg  840
acatgctttc ccacacagct aatgggttat caaagatgct tccagctctt aaccatgata  900
gaactgcttg tgtccaagga ggcttacaca aattaagtga tgctaatggt caggaaaagc  960
agccattggc actagtccag ggtgtggctt ctggtgcaga ggacaacgat gaggtctggt  1020
cagacagcga gcagagcttt ctggatcctg acattggggg agtggccgtg gctccaactc  1080
atgggtcaat tctcattgag tgtgcaaagc gtgagctgca tgccacaacc cctttaaaga  1140
atcccaatag gaatcacccc accaggatct ccctcgtctt ttaccagcat aagagcatga  1200
atgagccaaa acatggcttg gctctttggg aagccaaaat ggctgaaaaa gcccgtgaga  1260
aagaggaaga gtgtgaaaag tatggcccag actatgtgcc tcagaaatcc catggcaaaa  1320
aagtgaaacg ggagcctgct gagccacatg aaacttcaga gcccacttac ctgcgtttca  1380
tcaagtctct tgccgaaagg accatgtccg tgaccacaga ctccacagta actacatctc  1440
catatgcctt cactcgggtc acagggcctt acaacagata tatatgatat cacccccttt  1500
tg                                                                1502

SEQ ID NO: 63          moltype = DNA  length = 108
FEATURE                Location/Qualifiers
source                 1..108
                       mol_type = other DNA
                       organism = synthetic construct
SEQUENCE: 63
tggcctctgt ggtttctatc cctgcctttc tgggggcaga aatgtctgct gcagtccttc  60
cttttggaaa tctgaagact tttggaattg cccctgaaaa gaaaggaa              108

SEQ ID NO: 64          moltype = DNA  length = 3375
FEATURE                Location/Qualifiers
source                 1..3375
                       mol_type = other DNA
                       organism = synthetic construct
SEQUENCE: 64
tctaggtatt tattcttagt tgtgaacact ggattctgtg tggtcctgga tggcaccaac  60
tgtagtttcc tgttcaggca ttccctgagg gaccatattg tcttcaatta cctgctccct  120
tggaggggac cttgacactg gagctttaac caaattcaga gggtcgccac tgtcatcatc  180
tacttgcaga attgccacct ctgtggtgga tgcattcgat atttctagct gtaatggccc  240
caactccagg gaactacatt tagaagggtc acctggctca gagagtggag aacacagttt  300
atctttttga actccagagg tccgtgtgac aaagtcaaca aggtctggaa ggcaaggaga  360
tggcccaagg cctgcagaat taattgtttt taattccaat ccgagtgact cttgtttgtc  420
taattgggaa gattctttta cttcctcagg catcattcct cctgctaaca ggtcaagggc  480
ctggtgtgtt ccctctaggc cccccaagcc acggtcaaca ttttctgtaa gtccagtttt  540
caaaatgtta ggagaaggga tcctaacact cctgggatta ggtgagtttc gttcaccctc  600
tgtctcaaag tcaagcacca aggttttggg agaatctaac ggaaacccag aaaaagatgg  660
gattggttcg aagtcagcgg gatcggagga attacaccct ataggtgata cagaattttc  720
ttcacacact ttctgacaca agacagttgg ggatctatgt gctgggctta cccgagtagt  780
gcagaaatca acaggcatat cccccagatt ccccagggca gtaagctcct ctacctttaa  840
gtctgtagct tcaaagtctt ctagggcctt gctttctatt gtcactgtta actctggatg  900
gacatcttgt agctccagtg cttctgtttt tggtttctct gggctctccc aggtctctgg  960
cctcttcttg ttttcatccc aaacagccaa ctcatagatc tttttaactt gaaagtcttt  1020
tgatctttct ctcttgagtt tgagacttct gtacctagaa gttctagaag ctgattctgg  1080
agctgaattc tctagcccct cctcactaac aactgaaact ccttgctctt gtggactacc  1140
tgttaaacac atagctgatc tggctgggga atgaagcagc aactctgggg cagaaatttt  1200
cacaggtgta tcttgtgggt tgagtaaaga cctagcttct gataaaaatg agtctaattt  1260
tgcctttgtg aaagagcaag cctgtggact caatttgatc actactttac ttggagtttc  1320
acttcctgtc atcaatttat tggactgttc agcctctttg tcaatcatta gcaagttggg  1380
ctgttttact tctccctccc acatgtatct gtttccatgg ttcaaattag aatcatctat  1440
gctgtggggt ccaatgctgg tacttactcc ctcatcaact atcccctcag acagctcctt  1500
taccctttct tttagttcag tgtttgtctc tatctcactt tctctacaat cctcagattt  1560
acggagctct tggctttcct tatcctggtt aacagattct ctgaggtgga tttctaccaa  1620
cttctgagat tctttgcact gtatatctaa cagttgagga ggtggttcta caccaggtgg  1680
tcctggctct cccaggtcaa gctcactctt ctctggagat atatccctac tagtgtcact  1740
ctggaaggaa ctagaggtcc atatggccaa agtgtctgtc tttggggtaa ttgtttcata  1800
aggcctgctt tggcacaacc ttgtcagagg ctgtaggaag ccataggtgc tgcctgtgct  1860
ttttgggcct acatgttcta caactgacca tttccctagg gccaccagag tttttgcaat  1920
```

```
gggcttttca gagttgctaa ctataggagc agcgaccaaa ccctcatctt gatgcaactc  1980
ctcttgggat gcactgctgt tcaaaggaga agtagaagag gtgtctgaac ttttggttct  2040
agagaggttg ctattttccc cattggccaa tggaccacca cttagcttag tctcaggggc  2100
cccccttagtc tcaggggccc cctttccacc actactatag aatatgtcat acaggtcctt  2160
agcattggct gtggctaagc atgaatttcg cttctctaat tttttggctt gttcactgaa  2220
cacacttgag aggggtggtg gaggacgtac taacacagag aacagggtct ggtctcggtc  2280
actctcactc accccaggag ctgtctcatc agaaggaatg gcagctggct gtgctgaggc  2340
catgatggct acaggcaaca ctgggttcaa aatgttagga cccacgaagc cagggctgag  2400
agtctgagat acaactgggt ttgattttac tggagccaag atagcatttg cttgagcagc  2460
agacggggca gctggatgag gtataacggg gggtggtgga ggtggtggag gtgggggtgg  2520
tggaggaggt ggtagtattt gttcaggtaa atgagatggc tcactctttt cagccaacac  2580
cactttttcc tctggagacc cttttagaat cacctcttcc cctccaaatg ctttggagat  2640
gatgtctgga ggtaagagga gatcagctga agactcttta accactggca gaggtttagc  2700
agtggttcca gaggacttaa tagacagaaa ggtgttaaga ggagctggct tgctcattgt  2760
ggctgaacat gacttgcgga gtactgtgga tggaataggc aggttgggtc ggatcttagt  2820
ctgtgtggaa gttgtcacaa caggcatcca agggctggta tgtgcaacaa cagttttccc  2880
agagagcttg attttgatag gctttgcctt cccagcttca gttttgccat cctctttgtc  2940
cttactactt tctagaatct cttctttaga gatacttggg gtcaccaatg aacttttctc  3000
ctcttctttt tctggcttct tccagctgaa tttcccaaaa gaagatgatg ttggtgattc  3060
cttctttacc tcttctttta actggagttt gatgccagtg ttccttttat tttcagcttt  3120
ttcaggggag ttcctaccct cagagagttg gtcttctaat ttctcagaga ccttgtcatc  3180
ctcctttact tctttcacag cctttgcctt tttttctttc ttctcctcct ttggtttctc  3240
actaagtttg cgctttagct cactctgccg tcgccgttct gtctctagga ccacagccaa  3300
gccagcttgg cggtccagat tccgccgctc ctcatataat gggttttcat ccacatattt  3360
ctgggaagaa aaaag                                                    3375
```

```
SEQ ID NO: 65          moltype = DNA  length = 149
FEATURE                Location/Qualifiers
source                 1..149
                       mol_type = other DNA
                       organism = synthetic construct
SEQUENCE: 65
actacaaaga ccaaccttgt atttctcatt gtgttggtga cccttcacat gttgctcccc  60
agaaattgga tcccccaaaa attcctcaca gagctggcaa taaaatccac tgatgggaac  120
cagaaactca gagcctggaa gaagtagaa                                   149
```

```
SEQ ID NO: 66          moltype = DNA  length = 130
FEATURE                Location/Qualifiers
source                 1..130
                       mol_type = other DNA
                       organism = synthetic construct
SEQUENCE: 66
aaaaaggaaa catacctttt gcaggaacag ttatcttgtc agtgcgcttt atggcatctt  60
gcttggcctc actctgggtc tttgaagccc aaggtctgtt gtagggatcc agtgtctatt  120
tgtaagaggc                                                        130
```

```
SEQ ID NO: 67          moltype = DNA  length = 234
FEATURE                Location/Qualifiers
source                 1..234
                       mol_type = other DNA
                       organism = synthetic construct
SEQUENCE: 67
gagtaggata ccaacctgtg tgtgcttctt attgtgcata tgagtgaaga aatcaaacat  60
ggtcccacag atggtgttgc agtctttgca ccagtgattg ccagcatcat aatactcata  120
agcagcagtg ggctgatcca actgcttagt ggctgactgg gggctttcgg caggcttggg  180
gctcttagta cgaaacttct cattgtttac ttttgattcc tagaggggaa aaat        234
```

```
SEQ ID NO: 68          moltype = DNA  length = 332
FEATURE                Location/Qualifiers
source                 1..332
                       mol_type = other DNA
                       organism = synthetic construct
SEQUENCE: 68
aaattgagtt gttaccttgt tggaggagga gtttgagaac gatgacactt tttctgggct  60
cttagatttt tctgctttcc caggcttctc tgtaggctct ctactgtcac ttaaagactt  120
ctgggattta tcgaagatgt taattcccaa gatctgagcc actttgtcca gttcagattg  180
cttcttttct gcctcttctg cctcttgccg tagctctgca atgtccttca taatgttatc  240
ctgaagccga ctcacctcca ccaagagagg atctttgtgg ccatccttct cccttcgttt  300
cttgcgcagc atttctcctg agcaatcaaa tg                                332
```

```
SEQ ID NO: 69          moltype = DNA  length = 130
FEATURE                Location/Qualifiers
source                 1..130
                       mol_type = other DNA
                       organism = synthetic construct
SEQUENCE: 69
caaagcagct gataccttgt tgtttatgaa gccgctctaa ctcggtccta agatagtaca  60
tcttcttctg gcgggcttcc cggtcattct ttagtttttc cctctcttca ataacctgca  120
aaatacaaag                                                        130
```

```
SEQ ID NO: 70          moltype = DNA  length = 1512
FEATURE                Location/Qualifiers
source                 1..1512
                       mol_type = other DNA
                       organism = synthetic construct
SEQUENCE: 70
aaagctaata ttcacctttt gcttctggga agcacggttc ttctcatcag agatcttctc  60
tggattatat cttatgagtg atggaatgga cacctggaca ggcacttggg ccgcaggaat  120
tgagcctcgc agagactctt tctgcttagg cttatcagga gtcacagtgg ggatcacacg  180
aagattggga cggctacgag tagcttgttt ggttattggc attatcctgt gtggttcagg  240
tacagggtgg tttgacggtt gagaggtggg atacatgggc catctggagg ctgcatatgc  300
catgtagtgc ctataggcat caaaagaggc agggggaatg gcaggtccct ggtagttcgg  360
aggtatccga gctgcagcaa actgagaggc ccttggcatg tgaaactgag ataaagcagc  420
agtgtgtgga agtctaattg gggcagatgg ggctgatggc aacatgcacc tgactgcaac  480
agatgactga aacccactac caaccacctc tggtcctgaa atatgaccca ctggatggtc  540
agactttagg aatggagggc tgttttttgt gagcaggtaa ggatccacag gagaaggtgg  600
gtgtggatgg gacacctctg gagagtgggt attgctatga tgtgcctccc tgctctctag  660
tctgtgggga tctgaggaac gtcgatcagc tgagaagcag tggtcaactg aggaacagcg  720
gtcagctgag aagcggtggt caactgagga acagtggtca gctgaaaagt atcggtcaac  780
tgaggaacgg cggtcagctg aggagcgtaa tgatggcttc ttgccatgaa gtcgttcctg  840
ggtgcgtgca gccaattgac taatctctgc tactccaata tccagcccta ttgtcttgag  900
caagtcatgg atcttcgcat attctggatt ggtctcttct agtgattcta gctttacagc  960
tggagctgaa gacggcaggg agcttgcctt ctgcctcata acttcactct cagagctccc  1020
aaggggcttt ggtacggatt ctgcctttaa atcctcttct tcatccccat agagaaattt  1080
ctcctcatct tcaatgtcgg gaaagctacg tcgccttttt tcctgtgtac tggtagaatc  1140
agccaacatg ctcagaatgc gggaaaaacc actgccatcc tggctagctc tctcatgggg  1200
cagcaggaag tctgtgtgtc gctcaggtcc ctcagccttc aaatccaaat tatccttgtg  1260
gcatagaaaa cttccaaatt tttctctgag aggactgttg tctttgggaa tcccaggaag  1320
gggaccccat tggtagaggt tgccctgagg ttccttcaag gcagtctcta ccatagtccc  1380
cttgttttca atctctgagg caaaagcagc aatagcacca cttagtggaa gggatgggtg  1440
cccagagtag agagggtgat cctggctgga gctggtactg ctggaaaaac tctcaagctg  1500
caaagacaaa ca                                                     1512

SEQ ID NO: 71          moltype = DNA  length = 670
FEATURE                Location/Qualifiers
source                 1..670
                       mol_type = other DNA
                       organism = synthetic construct
SEQUENCE: 71
aaatgcagca gagacctgca tggagggctc cattatgtcc acctcaatcc gcttcttcaa  60
aatggatttc ttgggcatca cagatacttc ctcaggccga tgcaaagaat atcctggctc  120
cgatgctgtt aggacacctg acaatccagg gatggaacag ccagtaccac caccatcaac  180
tccaaccagc tcctgactca agctcctact tcgctcctcc tcttcctctc gctttcgtct  240
ggcaagatcc agttctcgaa actcagggtc gagaaaccta ggacttgggc ttcttctacg  300
ctgtcgatag ttgcgagttc ctgatgtaaa acttgggtga tcccctccca tgctgtttat  360
cttcactgtg tcatcataac ggggtctttt ggcctcccgg ctcctttctt cagatcgtat  420
ggagtagcct ttgagttttt ctcgattccg ttctgttccc cgcaacagct catcatgaca  480
actgatatgg ggactataat cagatcgatg caggaaagtt tcttttgttc ggtagtcctc  540
atcaagttgt cccaagaagg gactgagagg cccttcctcc tgggaaatat atcgctcaag  600
accccgagag cactgggagc ttcgagtgaa gacagaatca tcagtcaggt catccctgag  660
gaaaaagaga                                                        670

SEQ ID NO: 72          moltype = DNA  length = 179
FEATURE                Location/Qualifiers
source                 1..179
                       mol_type = other DNA
                       organism = synthetic construct
SEQUENCE: 72
ttaggtgatg cctacctgtc catgtcttcc agattatcca ctggtgaccc cagccgatca  60
ctaagccgtc gccgttctgg tgtgctaaca cagaagtggt cattgccaac agtgatcctt  120
aagctctttt ccaaagagtc agaacacaga ccaggagagc gtctctacaa aagtaaagg   179

SEQ ID NO: 73          moltype = DNA  length = 429
FEATURE                Location/Qualifiers
source                 1..429
                       mol_type = other DNA
                       organism = synthetic construct
SEQUENCE: 73
gaggggtggg attacccggc tgccgctgtc gcctggatgg tctccgcggc cgtcccgggc  60
atagtcggcg cgggactccc cccggctgct gcctctgaag ccggccgggc ccggcgggaa  120
gagtcgtcgg ccccgcggtg gcgacgggga gccgcgacgg gcccgaggcg gggacgggga  180
gacgcgacga ccccgtggcg gggacggcga ggcccggcgg ccgcggtgcc ctgagggcga  240
gcggggtcgg cgagccgggg tccgcgacga ggagccggag ggcggaggcg gcggtgagct  300
gcggcgagcc gggcctgagg aggagccaga gctgcggccg ctgcgcgggc cgccccccgcc  360
gtcgtcttta ggccggtggg aagagacgga ggagcgagcg ctgctgcggt acatggttct  420
tgcagcggc                                                         429

SEQ ID NO: 74          moltype = DNA  length = 137
```

```
FEATURE                Location/Qualifiers
source                 1..137
                       mol_type = other DNA
                       organism = synthetic construct
SEQUENCE: 74
ctttgtactt ttttttttcc ttagtctttc tttgaagcag caagtatgat gagcaagctt  60
tctcacaagc atttggtttt aaattatgga gtatgtgtct gtggagacga gagtaagtaa  120
aactacaggc tttctaa                                                 137

SEQ ID NO: 75          moltype = DNA  length = 2049
FEATURE                Location/Qualifiers
source                 1..2049
                       mol_type = other DNA
                       organism = synthetic construct
SEQUENCE: 75
ctttctctta aaggcatgga gagtagaaaa ctgatttctg ctacagacat tcagtactct  60
ggcagtctgc tgaactcctt gaatgagcaa cgtggccatg gactcttctg tgatgttacc  120
gttattgtgg aagaccgaaa attccgggct cacaagaata ttctttcagc ttctagtacc  180
tacttccatc agctcttctc tgttgctggg caagttgttg aactgagctt tataagagca  240
gagatctttg cagaaattct caattatatc tatagttcta aaattgttcg tgttagatca  300
gatttgcttg atgagttaat taaatcaggg cagttattag gagtgaaatt tatagcagag  360
cttggtgtcc cattgtcaca ggttaaaagc atctcaggta cagcgcagga tggtaatact  420
gagcctttac ctcctgattc tggtgacaag aaccttgtaa tacagaaatc aaaagatgaa  480
gcccaagata atggggctac tataatgcct attataacag agtcttttc attatctgcc  540
gaagattatg aaatgaaaaa gatcattgtt accgattctg atgatgatga tgatgatgtc  600
attttttgct ccgagattct gcccacaaag gagactttgc cgagtaataa cacagtggca  660
caggtccaat ctaacccagg ccctgttgct atttcagatg ttgcacctag tgctagcaat  720
aactcgcccc ctttaacaaa tatcacacct actcagaaac ttcctactcc tgtgaatcag  780
gcaactttga gccaaacaca aggaagtgaa aaattgttgg tatcttcagc tccaacacat  840
ctgactccca atattatttt gttaaatcag acaccacttt ctacaccacc aaatgtcagt  900
tcttcacttc caaatcatat gccctcttca atcaatttac ttgtgcagaa tcagcagaca  960
ccaaacagtg ctattttaac aggaaacaag gccaatgaag aggaggagga ggaaataata  1020
gatgatgatg atgacactat tagctccagt cctgactcgg ccgtcagtaa tacatctttg  1080
gtcccacagg ctgatacctc ccaaaatacc agttttgatg gatcattaat acagaagatg  1140
cagattccta cacttcttca agaaccactt tccaattcct taaaaatttc agatataatt  1200
actagaaata ctaatgatcc aggcgtagga tcaaaacatc taatggaggg tcagaagatc  1260
attactttag atacagctac tgaaattgaa ggcttatcga ctggttgcaa ggtttatgca  1320
aatatcggtg aagatactta tgatatagtg atccctgtca aagatgaccc tgatgaaggg  1380
gaggccagac ttgagaatga aataccaaaa acgtctggca gcgagatggc aaacaaacgt  1440
atgaaagtaa aacatgatga tcactatgag ttaatagtag atggaagggt ctattatatc  1500
tgtattgtat gcaaaaggtc atatgtctgt ctgacaagct tgcggagaca ttttaacatt  1560
cattcttggg agaagaagta tccgtgccgt tactgtgaga aggtatttcc tcttgcagaa  1620
tatcgcacaa agcatgaaat tcatcacaca ggggagcgaa ggtatcagtg tttggcctgt  1680
ggcaaatctt tcatcaacta tcagtttatg tcttcacata taaagtcagt tcatagtcaa  1740
gatccttctg gggactcaaa gctttatcgt ttacatccat gcaggtcttt acaaatcaga  1800
caatatgcat atctttccga tagatcaagc actattcctg caatgaagga tgatggtatt  1860
gggtataagg ttgacactgg aaaagaacct ccagtaggga ccactacatc tactcagaac  1920
aagccaatga cctgggaaga tatttttatt cagcaggaaa atgattcaat ttttaaacaa  1980
aatgtaacag atggcagtac tgagtttgaa tttataaatac cagagtctta ctaaactcct  2040
ttgaaatac                                                          2049

SEQ ID NO: 76          moltype = DNA  length = 143
FEATURE                Location/Qualifiers
source                 1..143
                       mol_type = other DNA
                       organism = synthetic construct
SEQUENCE: 76
tcgggccaag atggcggtgc aggtggtgca ggcggtgcag gcggttcatc tcgagtctga  60
cgctttcctc gtttgtctca accacgctct gagcacagag aaggaggaag taatggggct  120
gtgcataggg gaggtgagta ggt                                          143

SEQ ID NO: 77          moltype = DNA  length = 37
FEATURE                Location/Qualifiers
source                 1..37
                       mol_type = other DNA
                       organism = synthetic construct
SEQUENCE: 77
cccactctag ttgaacgatg atacaaggta agactgt                           37

SEQ ID NO: 78          moltype = DNA  length = 75
FEATURE                Location/Qualifiers
source                 1..75
                       mol_type = other DNA
                       organism = synthetic construct
SEQUENCE: 78
ttcccagtag gagtgactcc aaatttgcat atactggaac tgaaatgcgc acagttgctg  60
aaaaggtatg tgtgc                                                   75

SEQ ID NO: 79          moltype = DNA  length = 140
```

```
FEATURE                 Location/Qualifiers
source                  1..140
                        mol_type = other DNA
                        organism = synthetic construct
SEQUENCE: 79
tttcctttag gttgatgccg tcagaattgt tcacattcat tctgtcatca tcttacgacg  60
ttctgataag aggaaggacc gagtagaaat ttctccagag cagctgtctg cagcttcaac  120
agaggcagag atatccttac                                               140

SEQ ID NO: 80           moltype = DNA  length = 108
FEATURE                 Location/Qualifiers
source                  1..108
                        mol_type = other DNA
                        organism = synthetic construct
SEQUENCE: 80
acagacacac aggttggctg aactgacagg ccgccccatg agagttgtgg gctggtatca  60
ttcccatcct catataactg tttggccttc acatgttggt aagtatca                108

SEQ ID NO: 81           moltype = DNA  length = 109
FEATURE                 Location/Qualifiers
source                  1..109
                        mol_type = other DNA
                        organism = synthetic construct
SEQUENCE: 81
ttattttcag atgttcgcac acaagccatg taccagatga tggatcaagg ctttgtagga  60
cttatttttt cctgtttcat agaagataag aacacaaagg tattgtgtg               109

SEQ ID NO: 82           moltype = DNA  length = 76
FEATURE                 Location/Qualifiers
source                  1..76
                        mol_type = other DNA
                        organism = synthetic construct
SEQUENCE: 82
cctttgatag actggccggg tactctacac ttgcttccaa tccatacagg cccaaaagag  60
ttcagagtaa gtatga                                                   76

SEQ ID NO: 83           moltype = DNA  length = 95
FEATURE                 Location/Qualifiers
source                  1..95
                        mol_type = other DNA
                        organism = synthetic construct
SEQUENCE: 83
ccatcctaag gtcccttcat ggtccacgag acttctggag ctccagccag cacatctcca  60
ttgagggcca gaaggaagag gaaaggtagg agggc                              95

SEQ ID NO: 84           moltype = DNA  length = 152
FEATURE                 Location/Qualifiers
source                  1..152
                        mol_type = other DNA
                        organism = synthetic construct
SEQUENCE: 84
tgcctcacag gtatgagaga atcgaaatcc caatccatat tgtacctcat gtcactatcg  60
ggaaagtgtg ccttgaatca gcagtagagc tgcccaagat cctgtgccag gaggagcagg  120
atgcgtatag gaggatccac aggtagagac cc                                 152

SEQ ID NO: 85           moltype = DNA  length = 64
FEATURE                 Location/Qualifiers
source                  1..64
                        mol_type = other DNA
                        organism = synthetic construct
SEQUENCE: 85
tattctttag ccttacacat ctggactcag taaccaagat ccataatggc tcaggtaaga  60
attg                                                                64

SEQ ID NO: 86           moltype = DNA  length = 162
FEATURE                 Location/Qualifiers
source                  1..162
                        mol_type = other DNA
                        organism = synthetic construct
SEQUENCE: 86
ttttttttaat caaaggaaca atatgaatta tactgtgaga tgggctccac attccaacta  60
tgtaaaatat gtgctgaaaa tgataaggat gtaaagattg agccctgtgg acacctcatg  120
tgcacatcct gtcttacatc ctggcaggta cggatctaaa ca                      162

SEQ ID NO: 87           moltype = DNA  length = 234
FEATURE                 Location/Qualifiers
source                  1..234
                        mol_type = other DNA
                        organism = synthetic construct
```

```
SEQUENCE: 87
ttgcttcttc tgcaggaatc agaaggtcag ggctgtcctt tctgccgatg tgaaattaaa  60
ggtactgaac ccatcgtggt agatccgttt gatcctagag ggagtggcag cctgttgagg  120
caaggagcag agggagctcc ctccccaaat tatgatgatg atgatgatga acgagctgat  180
gatactctct tcatgatgaa ggaattggct ggtgccaagg taagatggca gttt        234

SEQ ID NO: 88          moltype = DNA  length = 123
FEATURE                Location/Qualifiers
source                 1..123
                       mol_type = other DNA
                       organism = synthetic construct
SEQUENCE: 88
gtgggatgtt tttgcagatg atgggctccc ggaagacagt cccccccagg atgttccgga  60
tagttccatt gggacttttc cacatcttct tcagcttgaa ctctgtgagg acagagataa  120
tag                                                                123

SEQ ID NO: 89          moltype = DNA  length = 112
FEATURE                Location/Qualifiers
source                 1..112
                       mol_type = other DNA
                       organism = synthetic construct
SEQUENCE: 89
aagaagtgga gaatgtcagt ctgagtcagg cccttctgtc ttgaacatga gttttttatg  60
gcgggaggta gactgaccct ttttggactt caggtggctg taggagacag aa          112

SEQ ID NO: 90          moltype = DNA  length = 137
FEATURE                Location/Qualifiers
source                 1..137
                       mol_type = other DNA
                       organism = synthetic construct
SEQUENCE: 90
gctgaggtca ctcacctgga gtgagccctg ctcccccctg gctccttccc agcctgggca  60
tccttgagtt ccaaggcctc attcagctct cggaacatct cgaagcgctc acgcccacgg  120
atctgcagca acagagg                                                 137

SEQ ID NO: 91          moltype = DNA  length = 78
FEATURE                Location/Qualifiers
source                 1..78
                       mol_type = other DNA
                       organism = synthetic construct
SEQUENCE: 91
tacaatattt tcaacttacg acgagtttat caggaagtaa caccatcgta agtcaagtag  60
catctgtatc aggcaaag                                                78

SEQ ID NO: 92          moltype = DNA  length = 63
FEATURE                Location/Qualifiers
source                 1..63
                       mol_type = other DNA
                       organism = synthetic construct
SEQUENCE: 92
attttcatgc tctctttaac aattttcttt ttgaaagctg gtctggtcct ttaaaatata  60
tat                                                                63

SEQ ID NO: 93          moltype = DNA  length = 104
FEATURE                Location/Qualifiers
source                 1..104
                       mol_type = other DNA
                       organism = synthetic construct
SEQUENCE: 93
cccaagactt agtacctgaa gggtgaaata ttctccatcc agtggtttct tctttggctg  60
gggagaggag ctggtgttgt tgggcagtgc taggaaagag gcaa                   104

SEQ ID NO: 94          moltype = DNA  length = 167
FEATURE                Location/Qualifiers
source                 1..167
                       mol_type = other DNA
                       organism = synthetic construct
SEQUENCE: 94
gtcctgcttg cttacctcgc ttagtgctcc ctgggggcag ctcgtggtga ggctcccctt  60
tcttgcggag attctcttcc tctgtgcgcc ggtctctccc aggacaggca caaacacgca  120
cctcaaagct gttccgtccc agtagattac cactactcag gatagga                167

SEQ ID NO: 95          moltype = DNA  length = 140
FEATURE                Location/Qualifiers
source                 1..140
                       mol_type = other DNA
                       organism = synthetic construct
SEQUENCE: 95
caagtggctc ctgacctgga gtcttccagt gtgatgatgg tgaggatggg cctccggttc  60
```

```
atgccgccca tgcaggaact gttacacatg tagttgtagt ggatggtggt acagtcagag  120
ccaacctagg agataacaca                                              140

SEQ ID NO: 96          moltype = DNA  length = 182
FEATURE                Location/Qualifiers
source                 1..182
                       mol_type = other DNA
                       organism = synthetic construct
SEQUENCE: 96
cactgacaac cacccttaac ccctcctccc agagacccca gttgcaaacc agacctcagg  60
cggctcatag ggcaccacca cactatgtcg aaaagtgttt ctgtcatcca aatactccac  120
acgcaaattt ccttccactc ggataagatg ctgaggaggg gccagaccta agagcaatca  180
gt                                                                 182

SEQ ID NO: 97          moltype = DNA  length = 216
FEATURE                Location/Qualifiers
source                 1..216
                       mol_type = other DNA
                       organism = synthetic construct
SEQUENCE: 97
gccccagctg ctcaccatcg ctatctgagc agcgctcatg gtgggggcag cgcctcacaa  60
cctccgtcat gtgctgtgac tgcttgtaga tggccatggc gcggacgcgg gtgccgggcg  120
ggggtgtgga atcaacccac agctgcacag ggcaggtctt ggccagttgg caaaacatct  180
tgttgagggc aggggagtac tgtaggaaga ggaagg                            216

SEQ ID NO: 98          moltype = DNA  length = 309
FEATURE                Location/Qualifiers
source                 1..309
                       mol_type = other DNA
                       organism = synthetic construct
SEQUENCE: 98
ctcagggcaa ctgaccgtgc aagtcacaga cttggctgtc ccagaatgca agaagcccag  60
acggaaaccg tagctgccct ggtaggtttt ctgggaaggg acagaagatg acaggggcca  120
ggagggggct ggtgcagggg ccgccggtgt aggagctgct ggtgcagggg ccacgggggg  180
agcagcctct ggcattctgg gagcttcatc tggacctggg tcttcagtga accattgttc  240
aatatcgtcc ggggacagca tcaaatcatc cattgcttgg gacggcaagg gggactgtag  300
atgggtgaa                                                          309

SEQ ID NO: 99          moltype = DNA  length = 52
FEATURE                Location/Qualifiers
source                 1..52
                       mol_type = other DNA
                       organism = synthetic construct
SEQUENCE: 99
aacccttgtc cttaccagaa cgttgttttc aggaagtctg aaagacaaga gc          52

SEQ ID NO: 100         moltype = DNA  length = 132
FEATURE                Location/Qualifiers
source                 1..132
                       mol_type = other DNA
                       organism = synthetic construct
SEQUENCE: 100
aatggatcca ctcacagttt ccataggtct gaaaatgttt cctgactcag agggggctcg  60
acgctaggat ctgactgcgg ctcctccatg gcagtgaccc ggaaggcagt ctggctgctg  120
caagaggaaa ag                                                      132

SEQ ID NO: 101         moltype = DNA  length = 273
FEATURE                Location/Qualifiers
source                 1..273
                       mol_type = other DNA
                       organism = synthetic construct
SEQUENCE: 101
ttcttttgaa tacagggtga gcatggacaa tcttgtgcca aaatgcttgt gaatcgagca  60
ttgggccgct ggaggcagcg tatgctccga gcagataaca ctagtgccat agtaatctgc  120
atctctccag aagtggacaa tcagggaaac tttaccaatg aagatgagtt atacctgaac  180
ctgactgaca gcccttccta taatagtcaa gaaacctgtg tgatgactcc ttccccatgt  240
tctacaccac cagtcaaggt atatagttcc ata                               273

SEQ ID NO: 102         moltype = DNA  length = 588
FEATURE                Location/Qualifiers
source                 1..588
                       mol_type = other DNA
                       organism = synthetic construct
SEQUENCE: 102
cttcttattt ttcagtcact ggaggaggat ccatggccaa gggtgaattc taaggaccat  60
atacctgccc tggttcgtag caatgccttc tcagagaatt ttttagaggt ttcagctgag  120
atagctcgag agaatgtcca aggtgtagtc ataccctcaa aagatccaga accacttgaa  180
gaaaattgcg ctaaagccct gactttaagg atacatgatt ctttgaataa tagccttcca  240
attggccttg tgcctactaa ttcaacaaac actgtcatgg accaaaaaaa tttgaagatg  300
```

```
tcaactcctg gccaaatgaa agcccaagaa attgaaagaa cccctccaac aaactttaaa  360
aggacattag aagagtccaa ttctggcccc ctgatgaaga agcatagacg aaatggctta  420
agtcgaagta gtggtgctca gcctgcaagt ctccccacaa cctcacagcg aaagaactct  480
gttaaactca ccatgcgacg cagacttagg ggccagaaga aaattggaaa tcctttactt  540
catcaacaca ggaaaactgt ttgtgtttgc tgaaatgcat ctgggaaa               588

SEQ ID NO: 103          moltype = DNA  length = 218
FEATURE                 Location/Qualifiers
source                  1..218
                        mol_type = other DNA
                        organism = synthetic construct
SEQUENCE: 103
gcggtcccct cagccccgtt tacctgcggc tccggcgtcc gtagccaccg cccccgtacc  60
tgcggggtgg cggtccccgg cggctgtggt gtgagtccgg ggggcggccg tagcgcgcca  120
tttgcacccg cagctcgcgg ccgtccagca cggccccgtc catggcatcc atagcgtcct  180
cagcgtcgcg cttgtcgtga aagcgaacga aggcgaag                          218

SEQ ID NO: 104          moltype = DNA  length = 87
FEATURE                 Location/Qualifiers
source                  1..87
                        mol_type = other DNA
                        organism = synthetic construct
SEQUENCE: 104
ccgccgggga gaaggatgaa ggacaaacag aagaagaaga aggagcgcac gtgggccgag  60
gccgcgcgcc tggtgaggcg gacagcc                                      87

SEQ ID NO: 105          moltype = DNA  length = 75
FEATURE                 Location/Qualifiers
source                  1..75
                        mol_type = other DNA
                        organism = synthetic construct
SEQUENCE: 105
cgtctcgttc aaccgatggg ggttgtgaat tttgtgttca gagcgtcaga ggacttgcag  60
gtgaaatagc ttcct                                                   75

SEQ ID NO: 106          moltype = DNA  length = 114
FEATURE                 Location/Qualifiers
source                  1..114
                        mol_type = other DNA
                        organism = synthetic construct
SEQUENCE: 106
tttatatttc ttcaggtatt agaaaactac tcggatgctc caatgacacc aaaacagatt  60
ctgcaggtca tagaggcaga aggactaaag gaaatgaggt ttgtattgtt cttg        114

SEQ ID NO: 107          moltype = DNA  length = 142
FEATURE                 Location/Qualifiers
source                  1..142
                        mol_type = other DNA
                        organism = synthetic construct
SEQUENCE: 107
tcttttgtgg ttttacagtg ggacttcccc tctcgcatgc ctcaatgcta tgctacattc  60
caattcaaga ggaggagagg ggttgtttta taaactgcct ggccgaatca gccttttcac  120
gctcaaggta agtgatatga ac                                           142

SEQ ID NO: 108          moltype = DNA  length = 151
FEATURE                 Location/Qualifiers
source                  1..151
                        mol_type = other DNA
                        organism = synthetic construct
SEQUENCE: 108
accttgctgt cacagaagga tgccctgcag tggtctcgcc atccagctac agtggaggga  60
gaggagccag aggacacggc tgatgtggag agctgtgggt ctaatgaagc cagcactgtg  120
agtggtgaaa acgatggtaa ggaccctttta a                                 151

SEQ ID NO: 109          moltype = DNA  length = 128
FEATURE                 Location/Qualifiers
source                  1..128
                        mol_type = other DNA
                        organism = synthetic construct
SEQUENCE: 109
tttcctctct tccagtatct cttgatgaaa catcttcgaa cgcatcctgt tctacagaat  60
ctcagagtcg acctctttcc aatcccaggg acagctacag agcttcctca caggtaagga  120
agaggtag                                                           128

SEQ ID NO: 110          moltype = DNA  length = 124
FEATURE                 Location/Qualifiers
source                  1..124
                        mol_type = other DNA
                        organism = synthetic construct
```

```
SEQUENCE: 110
tctcttggaa cgcaggcgaa caaacaaaag aaaaagactg gggtgatgct gcctcgagtt  60
gtcctgactc ctctgaaggt aaacggggcc cacgtggaat ctgcatcagg tatgtgtaaa  120
ctca                                                               124

SEQ ID NO: 111         moltype = DNA  length = 183
FEATURE                Location/Qualifiers
source                 1..183
                       mol_type = other DNA
                       organism = synthetic construct
SEQUENCE: 111
atgctgtgcc ttcagggttc tcgggctgcc acgccgatgg cgagagcggc agcccgtcca  60
gcagcagcag cggctctctg gccctgggca gcgctgctat tcgtggccag gccgaggtca  120
cccaggaccc tgccccgctc ctgagaggct tccggaagcc agccacaggt gagtggcgtg  180
gca                                                                183

SEQ ID NO: 112         moltype = DNA  length = 194
FEATURE                Location/Qualifiers
source                 1..194
                       mol_type = other DNA
                       organism = synthetic construct
SEQUENCE: 112
cttcaaaaat cataggtcaa atgaagcgca acagagggga agaaatagat tttgagacac  60
ctgggtccat tcttgtcaac accaacctcc gtgccctgat caactctcgg accttccatg  120
ccttaccatc acacttccag cagcagctcc tcttcctcct gcctgaagta gacagacagg  180
tgcacatggg cagc                                                    194

SEQ ID NO: 113         moltype = DNA  length = 127
FEATURE                Location/Qualifiers
source                 1..127
                       mol_type = other DNA
                       organism = synthetic construct
SEQUENCE: 113
ccttgatcct tctaggtggg gacggatggc ctgttgcgtc tcagcagcag tgcactaaat  60
aacgagtttt ttacccatgc ggctcagagc tggcgggagc gcctggctga tggtatgtag  120
acttggt                                                            127

SEQ ID NO: 114         moltype = DNA  length = 136
FEATURE                Location/Qualifiers
source                 1..136
                       mol_type = other DNA
                       organism = synthetic construct
SEQUENCE: 114
tttatttctc cctaggtgaa tttactcatg agatgcaagt caggatacga caggaaatgg  60
agaaggaaaa gaaggtggaa caatggaaag aaaagttctt tgaagactac tatggacaga  120
agtaaggcag ttggag                                                  136

SEQ ID NO: 115         moltype = DNA  length = 664
FEATURE                Location/Qualifiers
source                 1..664
                       mol_type = other DNA
                       organism = synthetic construct
SEQUENCE: 115
gattttgatt tgcaggctgg gtttgaccaa agaagagtca ttgcagcaga acgtgggcca  60
ggaggaggct gaaatcaaaa gtggcttgtg tgtcccagga gaatcagtgc gtatacagcg  120
tggtccagcc acccgacagc gagatgggca ttttaagaaa cgctctcggc cagatctccg  180
aaccagagcc agaaggaatc tgtacaaaaa acaggagtca gaacaagcag gggttgctaa  240
ggatgcaaaa tctgtggcct cagatgttcc cctctacaag gatggggagg ctaagactga  300
cccagcaggg ctgagcagtc cccatctgcc aggcacatcc tctgcagcac ccgacctgga  360
gggtcccgaa ttcccagttg agtctgtggc ttctcggatc caggctgagc cagacaactt  420
ggcacgtgcc tctgcatctc cagacagaat tcctagcctg cctcaggaaa ctgtggatca  480
ggaacccaag gatcagaaga ggaaatcctt tgagcaggcg gcctctgcat cctttcccga  540
aaagaagccc cggcttgaag atcgtcagtc ctttcgtaac acaattgaaa gtgttcacac  600
cgaaaagcca cagcccacta aagaggagcc caaagtcccg cccatccggg taggagactg  660
tttg                                                               664

SEQ ID NO: 116         moltype = DNA  length = 2937
FEATURE                Location/Qualifiers
source                 1..2937
                       mol_type = other DNA
                       organism = synthetic construct
SEQUENCE: 116
attctttttt tgcagattca actttcacgt atcaaaccac cctgggtggt taaaggtcag  60
cccacttacc agatatgccc ccggatcatc cccaccacgg agtcctcctg ccggggttgg  120
actggcgcca ggaccctcgc agacattaaa gcccgtgctc tgcaggtccg aggggcgaga  180
ggtcaccact gccatagaga ggcggccacc actgccatcg gaggggggggg tggcccgggt  240
ggaggtggcg gcggggccac cgatgaggga ggtggcagag gcagcagcag tggtgatggt  300
ggtgaggcct gtggccaccc tgagcccagg ggaggcccga gcacccctgg aaagtgtacg  360
tcagatctac agcgaacaca actactgccg ccttatcctc taaatgggga gcatacccag  420
```

```
gccggaactg ccatgtccag agctaggaga gaggacctgc cttctctgag aaaggaggaa  480
agctgcctac tacagagggc tacagttgga ctcacagatg ggctaggaga tgcctcccaa  540
ctccccgttg ctcccactgg ggaccagcca tgccaggcct tgcccctact gtcctcccaa  600
acctcagtag ctgagagatt agtggagcag cctcagttgc atccggatgt tagaactgaa  660
tgtgagtctg gcaccacttc ctgggaaagt gatgatgagg agcaaggacc caccgttcct  720
gcagacaatg gtcccattct gtctctagtg ggagatgata cattagagaa aggaactggc  780
caagctcttg acagtcatcc cactatgaag gatcctgtaa atgtgacccc cagttccaca  840
cctgaatcct caccgactga ttgcctgcag aacagagcat ttgatgacga attagggctt  900
ggtggctcat gccctcctat gagggaaagt gatactagac aagaaaactt gaaaaccaag  960
gctctcgttt ctaacagttc tttgcattgg atacccatcc catcgaatga tgaggtagtg  1020
aaacagccca aaccagaatc cagagaacac ataccatctg ttgagcccca ggttggagag  1080
gagtgggaga aagctgctcc cacccctcct gcattgcctg gggatttgac agctgaggag  1140
ggtctagatc ctcttgacag ccttacttca ctctggactg tgccatctcg aggaggcagt  1200
gacagcaatg gcagttactg tcaacaggtg gacattgaaa agctgaaaat caacggagac  1260
tctgaagcac tgagtcctca cggtgagtcc acggatacag cctctgactt tgaaggtcac  1320
ctcacggagg acagcagtga ggctgacact agagaagctg cagtgacaaa gggatcttcg  1380
gtggacaagg atgagaaacc caattggaac caatctgccc cactgtccaa ggtgaatggt  1440
gacatgcgtc tggttacaag gacagatggg atggttgctc ctcagagctg ggtgtctcga  1500
gtatgtgcgg tccgccaaaa gatcccagat tccctactgc tggccagtac tgagtaccag  1560
ccaagagccg tgtgcctgtc catgcctggg tcctcagtgg aggccactaa cccacttgtg  1620
atgcagttgc tgcagggtag cttgccccta gagaaggttc ttccaccagc ccacgatgac  1680
agcatgtcag aatccccaca agtaccactt acaaaagacc agagccatgg ctcgctacgc  1740
atgggatctt tacatggtct tggaaaaaac agtggcatgg ttgatggaag cagccccagt  1800
tctttaaggg ctttgaagga gcctcttctg ccagatagct gtgaaacagg cactggtctt  1860
gccaggattg aggccaccca ggctcctgga gcaccccaaa agaattgcaa ggcagtccca  1920
agttttgact ccctccatcc agtgacaaat cccattacat cctctaggaa actggaagaa  1980
atggattcca aagagcagtt ctcttccttt agttgtgaag atcagaagga agtccgtgct  2040
atgtcacagg acagtaattc aaatgctgct ccaggaaaga gcccaggaga tcttactacc  2100
tcgagaacac ctcgtttctc atctccaaat gtgatctcct ttggtccaga gcagacaggt  2160
cgggccctgg gtgatcagag caatgttaca ggccaaggga agaagctttt tggctctggg  2220
aatgtggctg caacccttca gcgccccagg cctgcggacc cgatgcctct tcctgctgag  2280
atccctccag tttttcccag tgggaagttg ggaccaagca caaactccat gtctggtggg  2340
gtacagactc caagggaaga ctgggctcca aagccacatg cctttgttgg cagcgtcaag  2400
aatgagaaga cttttgtggg gggtcctctt aaggcaaatg ccgagaacag gaaagctact  2460
gggcatagtc ccctggaact ggtgggtcac ttggaaggga tgccctttgt catggacttg  2520
cccttctgga aattaccccg agagccaggg aaggggctca gtgagcctct ggagccttct  2580
tctctcccct cccaactcag catcaagcag gcattttatg ggaagctttc taaactccaa  2640
ctgagttcca ccagctttaa ttattcctct agctctccca cctttcccaa aggccttgct  2700
ggaagtgtgg tgcagctgag ccacaaagca aactttggtg cgagccacag tgcatcactt  2760
tccttgcaaa tgttcactga cagcagcacg gtggaaagca tctcgctcca gtgtgcgtgc  2820
agcctgaaag ccatgatcat gtgccaaggc tgcggtgcgt tctgtcacga tgactgtatt  2880
ggaccctcaa agctctgtgt attgtgcctt gtggtgagat aataaattat ggccatg     2937

SEQ ID NO: 117         moltype = DNA  length = 104
FEATURE                Location/Qualifiers
source                 1..104
                       mol_type = other DNA
                       organism = synthetic construct
SEQUENCE: 117
tcaattttgt ttcaggacct gcttcgctgc cgtgtcctga cttctggaat ctttgagacc  60
aagttccagg tggacaaagt caacttccag taagccaact gtta                  104

SEQ ID NO: 118         moltype = DNA  length = 89
FEATURE                Location/Qualifiers
source                 1..89
                       mol_type = other DNA
                       organism = synthetic construct
SEQUENCE: 118
cctcctcccc accagcatgt ttgacgtggg tggccagcgc gatgaacgcc gcaagtggat  60
ccagtgcttc aacggtagga tgctgtggg                                   89

SEQ ID NO: 119         moltype = DNA  length = 151
FEATURE                Location/Qualifiers
source                 1..151
                       mol_type = other DNA
                       organism = synthetic construct
SEQUENCE: 119
ctctctttgg ttaagatgtg actgccatca tcttcgtggt ggccagcagc agctacaaca  60
tggtcatccg ggaggacaac cagaccaacc gcctgcagga ggctctgaac ctcttcaaga  120
gcatctggaa caacaggttt gtggagtgac c                                151

SEQ ID NO: 120         moltype = DNA  length = 161
FEATURE                Location/Qualifiers
source                 1..161
                       mol_type = other DNA
                       organism = synthetic construct
SEQUENCE: 120
cctcccttct tgtagatggc tgcgcaccat ctctgtgatc ctgttcctca acaagcaaga  60
tctgctcgct gagaaagtcc ttgctgggaa atcgaagatt gaggactact ttccagaatt  120
```

```
tgctcgctac actactcctg aggatggtgt gtatggcttc c                    161

SEQ ID NO: 121         moltype = DNA  length = 98
FEATURE                Location/Qualifiers
source                 1..98
                       mol_type = other DNA
                       organism = synthetic construct
SEQUENCE: 121
tcccttttta tatagctact cccgagcccg gagaggaccc acgcgtgacc cgggccaagt  60
acttcattcg agatgagttt ctggtgagtc gagcctgt                         98

SEQ ID NO: 122         moltype = DNA  length = 177
FEATURE                Location/Qualifiers
source                 1..177
                       mol_type = other DNA
                       organism = synthetic construct
SEQUENCE: 122
tgtttgtgcc cgcagaggat cagcactgcc agtggagatg ggcgtcacta ctgctaccct  60
catttcacct gcgctgtgga cactgagaac atccgccgtg tgttcaacga ctgccgtgac  120
atcattcagc gcatgcacct tcgtcagtac gagctgctct aagaagggaa cccccaa     177

SEQ ID NO: 123         moltype = DNA  length = 178
FEATURE                Location/Qualifiers
source                 1..178
                       mol_type = other DNA
                       organism = synthetic construct
SEQUENCE: 123
taaaaatggc atggctcaga atcgcccaga tctttcacga tctctcgacc gcctcctgtc  60
acgctcccgt ccgccgccac ctccaccacc gccaccgcca ccgccacgac cacggtctct  120
agaccgagaa cgacgctccc gggatcggga tcttgatcta tgcctgcaac caaggaaa    178

SEQ ID NO: 124         moltype = DNA  length = 127
FEATURE                Location/Qualifiers
source                 1..127
                       mol_type = other DNA
                       organism = synthetic construct
SEQUENCE: 124
cgggcacagg aatactcact tcttgcgacg gcggccatac agctcccgcc gcagctctct  60
ggaaatgggc ttcaaatgca tgaagttgca gaagccgcct cgtgtgcatt ctctgtgggt  120
gggttgg                                                            127

SEQ ID NO: 125         moltype = DNA  length = 164
FEATURE                Location/Qualifiers
source                 1..164
                       mol_type = other DNA
                       organism = synthetic construct
SEQUENCE: 125
ccactcctca ctcaccccat ctcatactga cggcagcagg cttctctgaa gtccgtcacg  60
ggtgacagct cggcgtggat cggctgtcca ttaaaccaac ggttattcaa gtcaatcaca  120
gccttttccg catcttcctc acggcgaaac tgaaaagaca aaaa                   164

SEQ ID NO: 126         moltype = DNA  length = 129
FEATURE                Location/Qualifiers
source                 1..129
                       mol_type = other DNA
                       organism = synthetic construct
SEQUENCE: 126
cgccctggct cctaccttga cgtacacgtt ccccaccagg tggtctccca ggttgtcaca  60
gacgttcatc tcctctactt ccccatactt ctcctccatt tctgtaaaaa cctcctgaag  120
ggagaccac                                                          129

SEQ ID NO: 127         moltype = DNA  length = 80
FEATURE                Location/Qualifiers
source                 1..80
                       mol_type = other DNA
                       organism = synthetic construct
SEQUENCE: 127
gttcagttct ctcacctcaa aaaactcatc atagtgttcc tgcatctcca catcgctcac  60
ggcacctgca aacaacagaa                                             80

SEQ ID NO: 128         moltype = DNA  length = 97
FEATURE                Location/Qualifiers
source                 1..97
                       mol_type = other DNA
                       organism = synthetic construct
SEQUENCE: 128
cttgtatgaa cttacagcgc aaaccgtcag cagactggga agagttttga gggttacggt  60
aaatgttcaa gagggcaatg gtctgaaata caaaacg                          97
```

-continued

```
SEQ ID NO: 129          moltype = DNA  length = 183
FEATURE                 Location/Qualifiers
source                  1..183
                        mol_type = other DNA
                        organism = synthetic construct
SEQUENCE: 129
ctctatgtca gcagctcaga agccaacatt atttgtctca attaagagtg ggctctttaa  60
caccattgtt ttaaaaaaat ttctccaact gtgggactta cagtgtgagc cgtcagccgt  120
ctgtgcactg ttttggggat tacgatagat gttttgaatc aagatggtct gcggggaaaa  180
aaa                                                                183

SEQ ID NO: 130          moltype = DNA  length = 118
FEATURE                 Location/Qualifiers
source                  1..118
                        mol_type = other DNA
                        organism = synthetic construct
SEQUENCE: 130
aaaaggcaaa caaacctggc taaacgtcgg tttattgtgc aaccgagagc acctgtctcc  60
atgacgacat gctccaattt tgaaataaaa tgaacagttg actctgtaag ggaaaatg    118

SEQ ID NO: 131          moltype = DNA  length = 74
FEATURE                 Location/Qualifiers
source                  1..74
                        mol_type = other DNA
                        organism = synthetic construct
SEQUENCE: 131
ggggctccca ctcacttgtc tttctcggtg ccgaagatgg aggccagata ctccgccatt  60
tcccacccgc cgcc                                                    74
```